(12) United States Patent
Jiménez Cenzano et al.

(10) Patent No.: US 11,629,361 B2
(45) Date of Patent: Apr. 18, 2023

(54) ADENO-ASSOCIATED VIRAL (AAV) VECTORS USEFUL FOR TRANSDUCING ADIPOSE TISSUE

(71) Applicant: Universitat Autònoma de Barcelona, Bellaterra Barcelona (ES)

(72) Inventors: Verónica Jiménez Cenzano, Cerdanyola del Vallés (ES); Fátima Bosch Tubert, Cerdanyola del Vallés (ES)

(73) Assignee: Universitat Autònoma de Barcelona, Barcelona (ES)

( * ) Notice: Subject to any disclaimer, the term of this patent is extended or adjusted under 35 U.S.C. 154(b) by 525 days.

(21) Appl. No.: 16/816,320

(22) Filed: Mar. 12, 2020

(65) Prior Publication Data

US 2020/0270640 A1    Aug. 27, 2020

Related U.S. Application Data

(62) Division of application No. 14/909,008, filed as application No. PCT/EP2013/066271 on Aug. 2, 2013, now Pat. No. 10,711,281.

(51) Int. Cl.
| | | |
|---|---|---|
| *C12N 15/86* | (2006.01) |
| *A61K 38/18* | (2006.01) |
| *A61K 38/45* | (2006.01) |
| *A61K 48/00* | (2006.01) |
| *C12N 5/077* | (2010.01) |
| *C12N 7/00* | (2006.01) |

(52) U.S. Cl.
CPC .......... *C12N 15/86* (2013.01); *A61K 38/1866* (2013.01); *A61K 38/45* (2013.01); *A61K 48/0058* (2013.01); *C12N 5/0653* (2013.01); *C12N 7/00* (2013.01); *C12Y 207/01002* (2013.01); *C12N 2750/14141* (2013.01); *C12N 2750/14143* (2013.01); *C12N 2830/008* (2013.01); *C12N 2830/85* (2013.01)

(58) Field of Classification Search
CPC ................ C22B 47/0036; C12N 15/86; C12N 2750/14141; C12N 2750/14143; C12N 2830/008; C12N 2830/85; C12N 5/0653; C12N 7/00; C12Y 207/01002; A61K 38/1866; A61K 2121/00; A61K 48/00; A61K 38/17; A61K 38/162
See application file for complete search history.

(56) References Cited

U.S. PATENT DOCUMENTS

| | | |
|---|---|---|
| 5,139,941 A | 8/1992 | Muzyczka et al. |
| 5,436,146 A | 7/1995 | Shenk et al. |
| 5,446,143 A | 8/1995 | Simpson et al. |
| 5,464,758 A | 11/1995 | Gossen et al. |
| 5,478,745 A | 12/1995 | Samulski et al. |
| 5,741,683 A | 4/1998 | Zhou et al. |
| 6,001,650 A | 12/1999 | Colosi |
| 6,057,152 A | 5/2000 | Samulski et al. |
| 6,136,597 A | 10/2000 | Hope et al. |
| 6,156,303 A | 12/2000 | Russell et al. |
| 6,165,782 A | 12/2000 | Naldini et al. |
| 6,204,059 B1 | 3/2001 | Samulski et al. |
| 6,207,455 B1 | 3/2001 | Chang |
| 6,218,181 B1 | 4/2001 | Verma et al. |
| 6,268,213 B1 | 7/2001 | Samulski et al. |
| 6,277,633 B1 | 8/2001 | Olsen |
| 6,323,031 B1 | 11/2001 | Cichutek |
| 6,358,732 B1 | 3/2002 | Sedlacek et al. |
| 6,432,705 B1 | 8/2002 | Yee et al. |
| 6,491,907 B1 | 12/2002 | Rabinowitz et al. |
| 6,531,456 B1 | 3/2003 | Kurtzman et al. |
| 6,596,535 B1 | 7/2003 | Carter |
| 6,660,514 B1 | 12/2003 | Zolotukhin et al. |
| 6,951,753 B2 | 10/2005 | Shenk et al. |
| 7,056,502 B2 | 6/2006 | Hildinger et al. |
| 7,094,604 B2 | 8/2006 | Snyder et al. |
| 7,125,717 B2 | 10/2006 | Carter |
| 7,172,893 B2 | 2/2007 | Rabinowitz et al. |
| 7,198,951 B2 | 4/2007 | Gao et al. |
| 7,201,898 B2 | 4/2007 | Monahan et al. |
| 7,220,577 B2 | 5/2007 | Zolotukhin |
| 7,229,823 B2 | 6/2007 | Samulski et al. |
| 7,235,393 B2 | 6/2007 | Gao et al. |
| 7,282,199 B2 | 10/2007 | Gao et al. |
| 7,319,002 B2 | 1/2008 | Wilson et al. |
| 7,439,065 B2 | 10/2008 | Ferrari et al. |
| 7,456,683 B2 | 11/2008 | Takano et al. |

(Continued)

FOREIGN PATENT DOCUMENTS

| | | |
|---|---|---|
| EP | 2394667 A1 | 12/2011 |
| EP | 2492347 A1 | 8/2012 |

(Continued)

OTHER PUBLICATIONS

Monahan P et al, AAV vectors: is clinical success on the horizon?, Gene Therapy, vol. 7, pp. 24-30, Jan. 17, 2000.
Del Mar Gonzalez-Barroso M, et al., Transcriptional Activation of the Human ucp1 Gene in a Rodent Cell LineSynergism Of Retinoids, Isoproterenol, and Thiazolidinedione is Mediated By a Multipartite Response Element. J. Biol. Chem. vol. 275(41), pp. 31722-31732, 2000.
Ahi et al, Adenoviral Vector Immunity: Its implications and circumvention strategies. Curr. Gene Ther. vol. 11(4), pp. 307-320, Aug. 2011.

(Continued)

*Primary Examiner* — Bao Q Li
(74) *Attorney, Agent, or Firm* — N.V. Nederlandsch Octrooibureau

(57) ABSTRACT

The present invention relates to adeno-associated viral vector useful for transducing adipose tissue. The invention also relates to polynucleotides, plasmids, vectors and methods for the production of such adeno-associated viral vector. The invention also relates to gene therapy methods useful for the treatment of a disease that requires the regulation of the expression levels of a gene.

20 Claims, 19 Drawing Sheets
Specification includes a Sequence Listing.

(56) References Cited

U.S. PATENT DOCUMENTS

| | | | |
|---|---|---|---|
| 7,790,449 | B2 | 9/2010 | Gao et al. |
| 2002/0065239 | A1 | 5/2002 | Caplan et al. |
| 2003/0138772 | A1 | 7/2003 | Gao et al. |
| 2003/0148506 | A1 | 8/2003 | Kotin et al. |
| 2003/0219409 | A1 | 11/2003 | Coffin et al. |
| 2004/0055023 | A1 | 7/2004 | Gao et al. |
| 2005/0187154 | A1 | 8/2005 | Kahn et al. |
| 2008/0075740 | A1 | 3/2008 | Gao et al. |
| 2010/0216709 | A1 | 8/2010 | Scheule et al. |
| 2010/0240029 | A1 | 9/2010 | Guarente et al. |
| 2011/0166210 | A1 | 7/2011 | Felber et al. |
| 2012/0040401 | A1 | 2/2012 | Ellis et al. |

FOREIGN PATENT DOCUMENTS

| | | |
|---|---|---|
| EP | 3101125 A1 | 12/2016 |
| JP | 2000/514421 | 10/2000 |
| WO | 1996040954 A1 | 12/1996 |
| WO | 1997/49827 A2 | 12/1997 |
| WO | 1997049827 A2 | 12/1997 |
| WO | 1998009524 A1 | 3/1998 |
| WO | 1998011244 A2 | 3/1998 |
| WO | 1999061601 A2 | 12/1999 |
| WO | 2000028061 A2 | 5/2000 |
| WO | 2001083692 A2 | 11/2001 |
| WO | 2001091803 A2 | 12/2001 |
| WO | 2001094605 A2 | 12/2001 |
| WO | 2003014367 A1 | 2/2003 |
| WO | 2003042397 A3 | 5/2003 |
| WO | 2003052051 A2 | 6/2003 |
| WO | 2003052052 A2 | 6/2003 |
| WO | 2006110689 A2 | 10/2006 |
| WO | 2007127264 A2 | 11/2007 |
| WO | 2008/103755 A1 | 8/2008 |
| WO | 2010010887 A1 | 1/2010 |
| WO | WO2011/154520 A1 | 12/2011 |
| WO | 2012007458 A1 | 1/2012 |
| WO | 2013/063379 A1 | 5/2013 |
| WO | WO2015173308 A1 | 11/2015 |
| WO | WO2016193431 A1 | 12/2016 |
| WO | WO2018/060097 A1 | 4/2018 |

OTHER PUBLICATIONS

Donello J, et al., Woodchuck hepatitis virus contains a tripartite posttranscriptional regulatory element, J. Virol. 1998, vol. 72(6), pp. 5085-5092 ,Jun. 1998.
Al-Dossari Mohammad et al, Evaluation of viral and mammalian promoters for driving transgene expression in mouse liver. Biochemical and Biophysical Research Communications vol. 339(2), pp. 673-678, Jan. 13, 2006.
F-L Zhang et al, Celastrol enhances AAV1-mediated gene expression in mice adipose tissues. Gene Therapy vol. 18 (2), pp. 128-134, Feb. 1, 2011.
Gao et al, Clades of Adeno-associated viruses are widely disseminated in human tissues. J. Virol. vol. 78, pp. 6381-6388, 2004.
Graves R, et al., Analysis of a tissue-specific enhancer: ARF6 regulates adipogenic gene expression. Mol. Cell Biol. vol. 12(3), pp. 1202-1208, 1992.
Amado and Chen, Lentiviral Vectors—the Promise of Gene Therapy Within Reach?, Science vol. 285, pp. 674-676 ,1999.
Graves RA et al, Identification of a potent adipocyte-specific enhancer: involvement of an NF-1-like factor. Genes & Development vol. 5(3), pp. 428-437, Mar. 1, 1991.
Hiroaki Mizukami, Adipose tissue as a novel target for in vivo gene transfer by adeno-associated viral vectors. Human Gene Therapy vol. 17, pp. 921-928, Jan. 1, 2006.
Apparailly et al, Adeno-associated virus pseudotype 5 vector improves gene transfer in arthritic joints., Hum Gene Ther., vol. 16(4):426-34, May 4, 2005.
Ayuso E, et al, Production, purification and characterization of adeno-associated vectors, Curr. Gene Ther., vol. 10, pp. 423-436, Dec. 1, 2010.
Kitajima et al, Persistent liver expression of murine apoA-l using vectors based on adeno-associated viral vectors serotypes 5 and 1. Atherosclerosis vol. 186, pp. 65-73, 2006.
Kozak U, et al., An upstream enhancer regulating brown-fat-specific expression of the mitochondrial uncoupling protein gene,Mol. Cell Biol. vol. 14, pp. 59-67, 1994.
Lebherz C, et al.,Novel AAV serotypes for improved ocular gene transfer. J. Gene Med. vol. 10, pp. 375-382, 2008.
Lee et al, Optimizing regulatable gene expression using adenoviral vectors. Experimental Physiology vol. 90, pp. 33-37, 2004.
Liu et al, Promoter effects of adeno-associated viral vector for transgene expression in the cochlea in vivo. Experimental and Molecular Medicine vol. 39, pp. 170-175, 2007.
Lock et al, Characterization of a recombinant adeno-associated virus type 2 Reference Standard Material. Hum. Gene Ther. vol. 21, pp. 1273-1285, 2010.
Moris et al, Two novel adeno-associated viruses from cynomolgus monkey: pseudotyping characterization of capsid protein. Virology vol. 330, pp. 375-383, 2004.
Muise, E. S. et al, Adipose fibroblast growth factor 21 is up-regulated by peroxisome proliferator-activated receptor gamma and altered metabolic states., Mol. Pharmacol., vol. 74, pp. 403-412, May 8, 2008.
Okada T et al, Scalable purification of adeno-associated virus serotype 1 (AAV1) and AAV8 vectors, using dual ion-exchange adsorptive membranes., Hum. Gene Ther., vol. 20, pp. 1013-1021, Aug. 5, 2009.
Rabinowitz J et al, Cross-Packaging of a Single Adeno-Associated Virus (AAV) Type 2 Vector Genome into Multiple AAV Serotypes Enables Transduction with Broad Specificity, vol. 76(2), pp. 791-801, Jan. 2002.
Bish L, et al., Adeno-Associated Virus (AAV) Serotype 9 Provides Global Cardiac Gene Transfer Superior to AAV1, AAV6, AAV7, and AAV8 in the Mouse and Rat. Hum. Gene Ther. vol. 19(12), pp. 1359-1368, 2008.
Rival Y, et al., Human Adipocyte Fatty Acid-Binding Protein (aP2) Gene Promoter-Driven Reporter Assay Discriminates Nonlipogenic Peroxisome Proliferator-Activated Receptor γ Ligands. J. Pharmacol. Exp. Ther. vol. 311 (2), pp. 467-475, 2004.
Ross S, et al., A fat-specific enhancer is the primary determinant of gene expression for adipocyte P2 in vivo. Proc. Natl. Acad. Sci. USA vol. 87, pp. 9590-9594, 1990.
Seale P, et al., Prdm16 determines the thermogenic program of subcutaneous white adipose tissue in mice. J. Clin. Invest. vol. 121(1), pp. 96-105, 2011.
Boshart M, et al., Cell, 1985, A very strong enhancer is located upstream of an immediate early gene of human cytomegalovirus, vol. 41, pp. 521-530, Jun. 1, 1985.
Boulos et al, Assessment of CMV, RSV and SYN1 promoters and the woodchuck post-transcriptional regulatory element in adenovirus vectors for transgene expression in cortical neuronal cultures. Brain Research vol. 1102, pp. 27-38, 2006.
Boyer B, et al., The Mitochondrial Uncoupling Protein Gene in Brown Fat:Correlation between DNaseI Hypersensitivity and Expression In Transgenic Mice. Mol. Cell Biol. vol. 11, pp. 4147-4156, 1991.
Taymans J, et al., Comparative analysis of adeno-associated viral vector serotypes 1, 2, 5, 7, and 8 in mouse brain. Hum. Gene Ther. vol. 18, pp. 195-206, 2007.
Broekman M, et al., Adeno-associated virus vectors serotyped with AAV8 capsid are more efficient than AAV-1 or -2 serotypes for widespread gene delivery to the neonatal mouse brain. Neuroscience vol. 138(2), pp. 501-510, 2006.
Urabe et al, A novel dicistronic AAV vector using a short IRES segment derived from hepatitis C virus genome. Gene vol. 200, pp. 157-162, 1997.
Wang et al, Improved neuronal transgene expression from an AAV-2 vector with a hybrid CMV enhancer/PDGF-β promoter, J Gene Med., vol. 7, pp. 945-955, Mar. 9, 2005.
Wu Z, et al., Effect of Genome Size on AAV Vector Packaging. Mol. Ther. vol. 18(1), pp. 80-86, 2010.

(56) References Cited

OTHER PUBLICATIONS

Cao D, Adipose tissue angiogenesis as a therapeutic target for obesity and metabolic diseases. Nature Rev. vol. 9, pp. 107-115, 2010.
Zarrin et al, Comparison of CMV, RSV, SV40 viral and Vlambda1 cellular promoters in B and T lymphoid and non-lymphoid cell lines. Biochimica and Physica Acta vol. 1446, pp. 135-139, 1999.
Zhang F, et al., Celastrol enhances AAV1-mediated gene expression in mice adipose tissues. Gene Ther. vol. 18, pp. 128-134, 2011.
Zincarelli et al, Analysis of AAV serotypes 1-9 mediated gene expression and tropism in mice after systemic injection. Mol Ther vol. 16(6), pp. 1073-1080, 2008.
Zufferey R, et al.,Woodchuck hepatitis virus post transcriptional regulatory element enhances expression of transgenes delivered by retroviral vectors. J. Virol. vol. 73, pp. 2886-2892, 1999.
Cassard-Doulcier A, et al.,A 211-bp enhancer of the rat uncoupling protein-1 (UCP-1) gene controls specific and regulated expression in brown adipose tissue. Biochem. J. vol. 333, pp. 243-246, 1998.
Casteilla Louis et al, Virus-based gene transfer approaches and adipose tissue biology, Current Gene Therapy, vol. 8(2), pp. 79-87, Apr. 2008.
Ayuso et al., High AAV vector purity results in serotype- and tissue-independent enhancement of transduction efficiency. Gene Ther. vol. 17, pp. 503-510, 2010.
Chao et al, Several log increase in therapeutic transgene delivery by distinct adeno-associated viral serotype vectors. Molecular Therapy vol. 2(6):619-623, 2000.
Chlorini et al, Cloning of adeno-associated virus type 4 (AAV4) and generation of recombinant AAV4 particles. J. Vir. vol. 71, pp. 6823-6833, 1998.
Daya et al., Gene therapy using adeno-associated virus vectors, Clin Microbiol Rev vol. 21(4), pp. 583-593, 2008.
Dressman D., AAV-Mediated Gene Transfer to Models of Muscular Dystrophy: Insights into Assembly of Multi-Subunit Membrane Proteins. University of Pittsburgh, Graduate Faculty of the School of Medicine, Dept. of Biochemistry and Molecular Genetics in partial fulfillment of the requirements for the degree of Doctor of Philosophy. 183 pages,1997.
Elias I. et al, Elias et al. Adipose tissue overexpression of vascular endothelial growth factor protects against diet-induced obesity and insulin resistance. Diabetes; vol. 61, pp. 1801-1813, 2012.
Gustafson et al., Restricted Adipogenesis in hypertrophic obesity: The role of WISP2, WNT, and BMP4, Diabetes, vol. 62, No. 9, Aug. 22, 2013.
Harms and Seale, Brown and beige fat: development, function and therapeutic potential, Nature Medicine, vol. 19, Sep. 29, 2013.
Loeb et al, "Enhanced expression of transgenes from adeno-associated virus vectors with the woodchuck hepatitis virus post-transcriptional regulatory element: implications for gene therapy." Human gene therapy 10.14 (1999): 2295-2305.
Anguela, Xavier M., et al. "Nonviral-mediated hepatic expression of IGF-I increases Treg levels and suppresses autoimmune diabetes in mice." Diabetes 62.2 (2013): 551-560.
Hoffman et al., Increased BMP4 improves insulin sensitivity and increases beige/brown adipogenesis in adult mice. Diabetologica, vol. 57, Suppl 1, S1-S566, Sep. 26, 2013.
Ichimura A, et al., Dysfunction of lipid sensor GPR120 leads to obesity in both mouse and human. Nature vol. 483, pp. 350-354, 2012.
Jimenez et al, In vivo adeno-associated viral vectormediated genetic engineering of white and brown adipose tissue in adult mice. Diabetes vol. 62, pp. 4012-4022, 2013.
Kahn et al., Mechanisms linking obesity to insulin resistance and type 2 diabetes, Nature vol. 444, pp. 840-846, 2006.
Yee J, et al., Subcutaneous adipose tissue fatty acid desaturation in adults with and without rare adipose disorders. Lipids Health Dis. vol. 11, pp. 19-30, 2012.
Yu J. et al, Protein deacetylation by SIRT1: an emerging key post-translational modification in metabolic regulation . . . Pharmacol Res vol. 62(1), pp. 35-41, 2010.
Qiao et al., Liver-specific microRNA-122 target sequences incorporated in AAV vectors efficiently inhibits transgene expression in the liver. Gene Therapy, vol. 18, pp. 403-410, 2011.
Kelly et al., Attenuation of Vesicular Stomatitis Virus Encephalitis through MicroRNA Targeting. Journal of Virology, vol. 84(3), pp. 1550-1562, 2010.
Chen et al., The role of microRNA-1 and microRNA-133 in skeletal muscle proliferation and differentiation, Nat. Genet. vol. 38, pp. 228-233, 2006.
Zhang et al., Adipose Tissue Transduction Using AAV8-Based Vectors: Inadvertent Gene Transfer into Liver, Molecular Therapy vol. 11 supp 1, article 862, 2005.
Yan et al., Inverted terminal repeat sequences are important for intermolecular recombination and circularization of adeno-associated virus genomes. Journal of Virology, vol. 79, pp. 364-379, 2005.
Card et al., MicroRNA silencing improves the tumor specificity of adenoviral transgene expression, vol. 19, pp. 451-459, 2012.

SEQUENCE LISTING

```
<160> NUMBER OF SEQ ID NOS: 20

<210> SEQ ID NO 1
<211> LENGTH: 1644
<212> TYPE: DNA
<213> ORGANISM: Artificial Sequence
<220> FEATURE:
<223> OTHER INFORMATION: cytomegalovirus enhancer and chicken beta-actin
      constitutive promoter

<400> SEQUENCE: 1
tcgacattga ttattgacta gttattaata gtaatcaatt acggggtcat tagttcatag        60
cccatatatg gagttccgcg ttacataact tacggtaaat ggcccgcctg gctgaccgcc       120
```

| | |
|---|---|
| caacgacccc cgcccattga cgtcaataat gacgtatgtt cccatagtaa cgccaatagg | 180 |
| gactttccat tgacgtcaat gggtggagta tttacggtaa actgcccact tggcagtaca | 240 |
| tcaagtgtat catatgccaa gtacgccccc tattgacgtc aatgacggta aatggcccgc | 300 |
| ctggcattat gcccagtaca tgaccttatg gactttcct acttggcagt acatctacgt | 360 |
| attagtcatc gctattacca tggtcgaggt gagccccacg ttctgcttca ctctcccat | 420 |
| ctcccccccc tccccacccc caattttgta tttatttatt ttttaattat tttgtgcagc | 480 |
| gatggggcg gggggggggg ggggcgcgc gccaggcggg gcggggcggg gcgaggggcg | 540 |
| gggcggggcg aggcggagag gtgcggcggc agccaatcag agcggcgcgc tccgaaagtt | 600 |
| tccttttatg gcgaggcggc ggcggcggcg gccctataaa aagcgaagcg cgcggcgggc | 660 |
| gggagtcgct gcgttgcctt cgccccgtgc cccgctccgc gccgcctcgc gccgcccgcc | 720 |
| ccggctctga ctgaccgcgt tactcccaca ggtgagcggg cgggacggcc cttctcctcc | 780 |
| gggctgtaat tagcgcttgg tttaatgacg gcttgtttct tttctgtggc tgcgtgaaag | 840 |
| ccttgagggg ctccgggagg gccctttgtg cgggggagc ggctcggggg gtgcgtgcgt | 900 |
| gtgtgtgtgc gtggggagcg ccgcgtgcgg ctccgcgctg cccggcggct gtgagcgctg | 960 |
| cgggcgcggc gcggggcttt gtgcgctccg cagtgtgcgc gaggggagcg cggccggggg | 1020 |
| cggtgccccg cggtgcgggg ggctgcgagg ggaacaaagg ctgcgtgcgg ggtgtgtgcg | 1080 |
| tgggggggtg agcaggggt gtgggcgcgt cggtcgggct gcaaccccc ctgcaccccc | 1140 |
| ctccccgagt tgctgagcac ggcccggctt cgggtgcggg gctccgtacg gggcgtggcg | 1200 |
| cggggctcgc cgtgccgggc ggggggtggc ggcaggtggg ggtgccgggc ggggcggggc | 1260 |
| cgcctcgggc cggggagggc tcggggagg ggcgcggcgg ccccggagc gccggcggct | 1320 |
| gtcgaggcgc ggcgagccgc agccattgcc ttttatggta atcgtgcgag agggcgcagg | 1380 |
| gacttccttt gtcccaaatc tgtgcggagc cgaaatctgg gaggcgccgc cgcaccccct | 1440 |
| ctagcgggcg cggggcgaag cggtgcggcg ccggcaggaa ggaaatgggc gggagggcc | 1500 |
| ttcgtgcgtc gccgcgccgc cgtccccttc tccctctcca gcctcggggc tgtccgcggg | 1560 |
| gggacggctg ccttcggggg ggacggggca gggcggggtt cggcttctgg cgtgtgaccg | 1620 |
| gcggctctag agcctctgct aacc | 1644 |

<210> SEQ ID NO 2
<211> LENGTH: 600
<212> TYPE: DNA
<213> ORGANISM: Artificial Sequence
<220> FEATURE:
<223> OTHER INFORMATION: adipose-specific aP2 enhancer and basal murine
    aP2 promoter

<400> SEQUENCE: 2

| | |
|---|---|
| aattccagca ggaatcaggt agctggagaa tcgcacagag ccatgcgatt cttggcaagc | 60 |
| catgcgacaa aggcagaaat gcacatttca cccagagaga agggattgat gtcagcagga | 120 |
| agtcaccacc cagagagcaa atggagttcc cagatgcctg acatttgcct tcttactgga | 180 |
| tcagagttca ctagtggaag tgtcacagcc caaacactcc cccaaagctc agcccttcct | 240 |
| tgccttgtaa caatcaagcc gctcctggat gaactgctcc gccctctgtc tctttggcag | 300 |
| ggttggagcc cactgtggcc tgagcgactt ctatggctcc cttttctgtg attttcatgg | 360 |
| tttctgagct cttttccccc gctttatgat tttctctttt tgtctctctc ttgctaaacc | 420 |
| tccttcgtat atatgccctc tcaggtttca tttctgaatc atctactgtg aactattccc | 480 |

| | |
|---|---|
| attgtttgcc agaagccccc tggttcttcc ttctagacac caggcaaggg gcaggaggta | 540 |
| agaggcagga gtccataaaa cagccctgag agcctgctgg gtcagtgcct gctgtcagaa | 600 |

<210> SEQ ID NO 3
<211> LENGTH: 722
<212> TYPE: DNA
<213> ORGANISM: Artificial Sequence
<220> FEATURE:
<223> OTHER INFORMATION: adipose-specific UCP1 enhancer and basal rat
      UCP1 promoter

<400> SEQUENCE: 3

| | |
|---|---|
| gacgtcacag tgggtcagtc acccttgatc acactgcacc agtcttcacc tttccacgct | 60 |
| tcctgccaga gcatgaatca ggctctctgg ggataccggc ctcacccccta ctgaggcaaa | 120 |
| ctttctccca cttctcagag gctctgaggg cagcaaggtc agccctttct ttggaatcta | 180 |
| gaaccactcc ctgtcttgag ctgacatcac agggcaggca gatgcagcag ggaagggcct | 240 |
| gggactggga cgttcatcct acaagaaagc tgtggaactt ttcagcaaca tctcagaaat | 300 |
| cagatcgcac ttattcaaag gagccaggcc ctgctctgcg ccctggtgga ggctcctcat | 360 |
| gtgaagagtg acaaaaggca ccatgttgtg gatacggggc gaagcccctc cggtgtgtcc | 420 |
| tccaggcatc atcaggaact agtgccaaag cagaggtgct ggccagggct ttgggagtga | 480 |
| cgcgcgtctg ggaggcttgt gcgcccaggg cacgcccctg ccgattccca ctagcaggtc | 540 |
| ttgggggacc tgggccggct ctgccctcc tccagcaatc gggctataaa gctcttccaa | 600 |
| gtcagggcgc agaagtgccg ggcgatccgg gcttaaagag cgagaggaag ggacgctcac | 660 |
| ctttgagctc ctccacaaat agccctggtg gctgccacag aagttcgaag ttgagagttc | 720 |
| gg | 722 |

<210> SEQ ID NO 4
<211> LENGTH: 20
<212> TYPE: DNA
<213> ORGANISM: Artificial Sequence
<220> FEATURE:
<223> OTHER INFORMATION: RFP sense oligonucleotide

<400> SEQUENCE: 4

| | |
|---|---|
| gcggccacta cacctgcgac | 20 |

<210> SEQ ID NO 5
<211> LENGTH: 20
<212> TYPE: DNA
<213> ORGANISM: Artificial Sequence
<220> FEATURE:
<223> OTHER INFORMATION: RFP antisense oligonucleotide

<400> SEQUENCE: 5

| | |
|---|---|
| tcggcgtgct cgtactgctc | 20 |

<210> SEQ ID NO 6
<211> LENGTH: 20
<212> TYPE: DNA
<213> ORGANISM: Artificial Sequence
<220> FEATURE:
<223> OTHER INFORMATION: mHkII sense oligonucleotide

<400> SEQUENCE: 6

| | |
|---|---|
| gaagggcta ggagctacca | 20 |

<210> SEQ ID NO 7

```
<211> LENGTH: 19
<212> TYPE: DNA
<213> ORGANISM: Artificial Sequence
<220> FEATURE:
<223> OTHER INFORMATION: mHkII antisense oligonucleotide

<400> SEQUENCE: 7
ctcggagcac acggaagtt                                                    19

<210> SEQ ID NO 8
<211> LENGTH: 17
<212> TYPE: DNA
<213> ORGANISM: Artificial Sequence
<220> FEATURE:
<223> OTHER INFORMATION: hSEAP sense oligonucleotide

<400> SEQUENCE: 8
cggctgttgg gcactga                                                      17

<210> SEQ ID NO 9
<211> LENGTH: 19
<212> TYPE: DNA
<213> ORGANISM: Artificial Sequence
<220> FEATURE:
<223> OTHER INFORMATION: hSEAP antisense oligonucleotide

<400> SEQUENCE: 9
ggaaggtccg ctggattga                                                    19

<210> SEQ ID NO 10
<211> LENGTH: 24
<212> TYPE: DNA
<213> ORGANISM: Artificial Sequence
<220> FEATURE:
<223> OTHER INFORMATION: mVEGF164 sense oligonucleotide

<400> SEQUENCE: 10
agacagaaca aagccagaaa tcac                                              24

<210> SEQ ID NO 11
<211> LENGTH: 20
<212> TYPE: DNA
<213> ORGANISM: Artificial Sequence
<220> FEATURE:
<223> OTHER INFORMATION: mVEGF164 antisense oligonucleotide

<400> SEQUENCE: 11
cacgtctgcg gatcttggac                                                   20

<210> SEQ ID NO 12
<211> LENGTH: 20
<212> TYPE: DNA
<213> ORGANISM: Artificial Sequence
<220> FEATURE:
<223> OTHER INFORMATION: total mVEGF sense oligonucleotide

<400> SEQUENCE: 12
aaaaacgaaa gcgcaagaaa                                                   20

<210> SEQ ID NO 13
<211> LENGTH: 20
<212> TYPE: DNA
<213> ORGANISM: Artificial Sequence
<220> FEATURE:
<223> OTHER INFORMATION: total mVEGF antisense oligonucleotide

<400> SEQUENCE: 13
```

-continued

```
tttctccgct ctgaacaagg                                                20
```

<210> SEQ ID NO 14
<211> LENGTH: 21
<212> TYPE: DNA
<213> ORGANISM: Artificial Sequence
<220> FEATURE:
<223> OTHER INFORMATION: mPECAM1 sense oligonucleotide

<400> SEQUENCE: 14

```
ctggtgctct atgcaagcct c                                              21
```

<210> SEQ ID NO 15
<211> LENGTH: 19
<212> TYPE: DNA
<213> ORGANISM: Artificial Sequence
<220> FEATURE:
<223> OTHER INFORMATION: mPECAM1 antisense oligonucleotide

<400> SEQUENCE: 15

```
cggtgctgag acctgcttt                                                 19
```

<210> SEQ ID NO 16
<211> LENGTH: 19
<212> TYPE: DNA
<213> ORGANISM: Artificial Sequence
<220> FEATURE:
<223> OTHER INFORMATION: GFP sense oligonucleotide

<400> SEQUENCE: 16

```
aagttcatct gcaccaccg                                                 19
```

<210> SEQ ID NO 17
<211> LENGTH: 21
<212> TYPE: DNA
<213> ORGANISM: Artificial Sequence
<220> FEATURE:
<223> OTHER INFORMATION: GFP antisense oligonucleotide

<400> SEQUENCE: 17

```
tccttgaaga agatggtgcg c                                              21
```

<210> SEQ ID NO 18
<211> LENGTH: 2210
<212> TYPE: DNA
<213> ORGANISM: Artificial Sequence
<220> FEATURE:
<223> OTHER INFORMATION: VP1 from AAV9

<400> SEQUENCE: 18

```
atggctgccg atggttatct tccagattgg ctcgaggaca accttagtga aggaattcgc      60
agtggtgggc tttgaaacct ggagcccctc aacccaaggc aaatcaacaa catcaagaca     120
acgctcgagg tcttgtgctt ccgggttaca ataccttgg acccgcaac ggactcgaca       180 aggggagcc ggtcaacgca gcagacgcgg cggccctcga gcacgacaag gcctacgacc     240
agcagctcaa ggccggagac aacccgtacc tcaagtacaa ccacgccgac gccgagttcc     300
aggagcggct caaagaagat acgtcttttg ggggcaacct cgggcgagca gtcttccagg     360
ccaaaaagag gcttcttgaa cctcttggtc tggttgagga agcggctaag acggctcctg     420
gaaagaagag gcctgtagag cagtctcctc aggaaccgga ctcctccgcg ggtattggca     480
aatcgggtgc acagcccgct aaaaagagac tcaatttcgg tcagactggc gacacagagt     540
```

| | |
|---|---|
| cagtcccaga ccctcaacca atcggagaac ctcccgcagc cccctcaggt gtgggatctc | 600 |
| ttacaatggc ttcaggtggt ggcgcaccag tggcagacaa taacgaaggt gccgatggag | 660 |
| tgggtagttc ctcgggaaat tggcattgcg attcccaatg gctggggac agagtcatca | 720 |
| ccaccagcac ccgaacctgg gccctgccca cctacaacaa tcacctctac aagcaaatct | 780 |
| ccaacgcac atctggagga tcttcaaatg caacgccta cttcggctac agcaccccct | 840 |
| gggggtattt tgacttcaac agattccact gccacttctc accacgtgac tggcagcgac | 900 |
| tcatcaacaa caactgggga ttccggccta agcgactcaa cttcaagctc ttcaacattc | 960 |
| aggtcaaaga ggttacggac aacaatggag tcaagaccat cgccaataac cttaccagca | 1020 |
| cggtccaggt cttcacggac tcagactatc agctcccgta cgtgctcggg tcggctcacg | 1080 |
| agggctgcct cccgccgttc ccagcggacg ttttcatgat tcctcagtac gggtatctga | 1140 |
| cgcttaatga tggaagccag gccgtgggtc gttcgtcctt ttactgcctg aatatttcc | 1200 |
| cgtcgcaaat gctaagaacg ggtaacaact ccagttcag ctacgagttt gagaacgtac | 1260 |
| ctttccatag cagctacgct cacagccaaa gcctggaccg actaatgaat ccactcatcg | 1320 |
| accaatactt gtactatctc tcaaagacta ttaacggttc tggacagaat caacaaacgc | 1380 |
| taaaattcag tgtggccgga cccagcaaca tggctgtcca gggaagaaac tacatacctg | 1440 |
| gacccagcta ccgacaacaa cgtgtctcaa ccactgtgac tcaaaacaac aacagcgaat | 1500 |
| ttgcttggcc tggagcttct tcttgggctc tcaatggacg taatagcttg atgaatcctg | 1560 |
| gacctgctat ggccagccac aaagaaggag aggaccgttt ctttccttg tctggatctt | 1620 |
| taattttgg caaacaagga actggaagag acaacgtgga tgcggacaaa gtcatgataa | 1680 |
| ccaacgaaga agaaattaaa actactaacc cggtagcaac ggagtcctat ggacaagtgg | 1740 |
| ccacaaacca ccagagtgcc caagcacagg cgcagaccgg ctgggttcaa aaccaaggaa | 1800 |
| tacttccggg tatggtttgg caggacagag atgtgtacct gcaaggaccc atttgggcca | 1860 |
| aaattcctca cacggacggc aactttcacc cttctccgct gatgggaggg tttggaatga | 1920 |
| agcacccgcc tcctcagatc ctcatcaaaa acacacctgt acctgcggat cctccaacgg | 1980 |
| ccttcaacaa ggacaagctg aactcttca tcacccagta ttctactggc caagtcagcg | 2040 |
| tggagatcga gtgggagctg cagaaggaaa acagcaagcg ctggaacccg gagatccagt | 2100 |
| acacttccaa ctattacaag tctaataatg ttgaatttgc tgttaatact gaaggtgtat | 2160 |
| atagtgaacc ccgcccatt ggcaccagat acctgactcg taatctgtaa | 2210 |

<210> SEQ ID NO 19
<211> LENGTH: 22
<212> TYPE: DNA
<213> ORGANISM: Artificial Sequence
<220> FEATURE:
<223> OTHER INFORMATION: mirT122a

<400> SEQUENCE: 19
caaacaccat tgtcacactc ca                                          22

<210> SEQ ID NO 20
<211> LENGTH: 22
<212> TYPE: DNA
<213> ORGANISM: Artificial Sequence
<220> FEATURE:
<223> OTHER INFORMATION: mirT1

```
<400> SEQUENCE: 20
ttacatactt ctttacattc ca                                                    22
```

ADENO-ASSOCIATED VIRAL (AAV) VECTORS USEFUL FOR TRANSDUCING ADIPOSE TISSUE

REFERENCE TO AN ELECTRONIC SEQUENCE LISTING

The contents of the electronic sequence listing (sequence-listing.txt; Size: 11 Kb; and Date of Creation: May 7, 2020) is herein incorporated by reference in its entirety.

FIELD OF THE INVENTION

The present invention relates to adeno-associated viral (AAV) vectors useful for transducing adipose tissue. The vectors may transduce white or brown adipose tissue in a tissue-specific manner.

BACKGROUND OF THE INVENTION

Adipose tissue has been recognized recently as a major metabolic and endocrine organ, in addition to its already known role as a fat reservoir and modulator of energy homeostasis. It has been proposed that impaired white adipose tissue (WAT) function, as well as decreased brown adipose tissue (BAT) activity or BAT mass, are main contributors to the development of obesity. In this regard, adipocyte and WAT dysfunction have been described in humans. Moreover, an inverse correlation between BAT activity and body mass index (BMI) has also been reported. See Yee J, et al., Lipids Health Dis. 2012, 11:19-30, Ichimura A, et al., Nature 2012; 483: 350-354, Mazzatti D, et al., Arch. Physiol. Biochem. 2012; 118(3):112-120, Cypess A, et al., N. Engl. J. Med. 2009; 360:1509-1517, and van Marken Lichtenbelt W, et al., N. Engl. J. Med. 2009; 360:1500-1508.

The incidence of obesity has increased dramatically during the last decades to reach epidemic proportions. It is estimated that over 500 million individuals are obese. Obesity is a major public health problem today. See IASO, "Global Prevalence of Adult Obesity, Report IOTF 2008" (IASO, London, GB, 2009). Obesity per se increases the risk of mortality and has been long strongly associated with insulin resistance and type 2 diabetes. See Peeters A, et al., Ann. Intern. Med. 2003; 138:24-32 and Moller D, et al., N. Engl. J. Med. 1991; 325:938-948. In addition, adipocyte dysfunction and obesity are also significant risk factors for certain types of cancer and for many other serious illnesses such as heart disease, immune dysfunction, hypertension, arthritis, and neurodegenerative diseases. See Roberts D, et al., Annu. Rev. Med. 2010; 61:301-316, Spiegelman B, et al., J. Biol. Chem. 1993; 268(10):6823-6826, and Whitmer R, et al., Curr. Alzheimer Res. 2007; 4(2):117-122.

Diet and exercise are the mainstay treatments for obesity, but an increasing number of patients also require pharmacotherapeutic intervention to decrease and maintain body weight. However, pharmacotherapy does not induce involuntary nor substantial weight loss and, additionally, anti-obesity drugs often display important side effects due to their systemic actions. Hence, there is an urgent need for novel and safe approaches to prevent and combat the current obesity epidemic. In this regard, unraveling the pathological events underpinning obesity is crucial for the development of new anti-obesity therapies. In vivo gene transfer of candidate genes to white and brown adipose tissue may offer great potential to gain insight into the molecular mechanisms underlying the onset and development of obesity. In addition, gene therapy approaches targeting adipocytes may open up new opportunities for the future treatment of obesity and their associated disorders while minimizing systemic effects. To date, however, effective and specific gene transfer to white and brown adipose tissue remains elusive.

Recently, the AAV of serotype 1 (AAV1) has been shown to modestly infect mouse WAT in vivo when combined with a non-ionic surfactant or celastrol. See Mizukami H, et al., Hum. Gene Ther. 2006; 17:921-928 and Zhang F, et al., Gene Ther. 2011; 18:128-134. Other AAV serotypes such as AAV6, AAV7, AAV8 or AAV9 have been reported to be highly infectious but their adipose transduction efficiency is unclear. See Gao G, et al., Proc. Natl. Acad. Sci. USA 2002; 99:11854-11859, Nakai H, et al., J. Virol. 2005; 79:214-224, Pacak C, et al., Circ. Res. 2006; 99:e3-e9, Broekman M, et al., Neuroscience 2006; 138:501-510, Wang Z, et al., Diabetes 2006; 55:875-884, Taymans J, et al., Hum. Gene Ther. 2007; 18:195-206, Bish L, et al., Hum. Gene Ther. 2008; 19:1359-1368, and Lebherz C, et al., J. Gene Med. 2008; 10:375-382. Thus, there is a need in the art for the development of vectors that allow the specific transduction of adipose tissue and, moreover, the transduction of particular types of adipose cells.

SUMMARY OF THE INVENTION

The present invention refers to adeno-associated viral vectors (AAV) that allow the delivery of polynucleotides of interest to specific types of adipose cells and their expression. The use of the adipose tissue-specific regulatory elements of the invention restricts the expression of the polynucleotides of interest to either white adipose tissue or brown adipose tissue. Moreover, the vectors of the invention have been proven useful for the treatment of adipose tissue associated diseases such as, for example, type 2 diabetes. The inventive aspects of the present invention are disclosed in the claims.

Deposit of Microorganisms

The plasmids pAAV-mini/aP2-null and pAAV-mini/UCP1-null were deposited on Jun. 8, 2012 at the DSMZ (Deutsche Sammlung von Mikroorganismen and Zellkulturen GmbH), InhoffenstraBe 7 B, D-38124 Braunschweig, Federal Republic of Germany, under accession numbers DSM 26057 and DSM 26058, respectively.

DETAILED DESCRIPTION OF THE INVENTION

Figure 1:
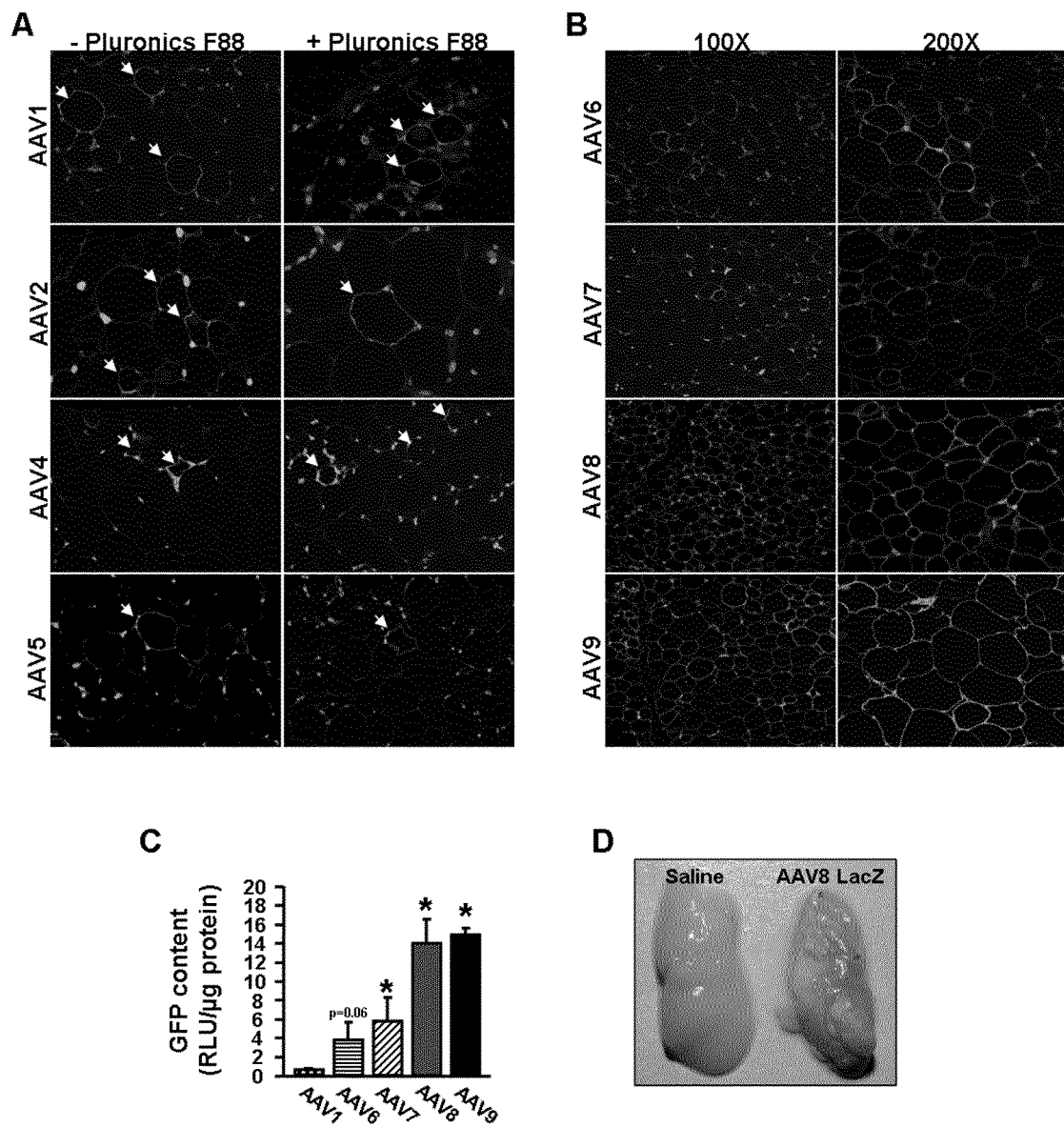
FIG. 1. Transduction of white adipocytes by intra-eWAT administration of AAV. A-B. Immunostaining against green fluorescent protein (GFP, in green) in sections of eWAT treated with AAV-CAG-GFP of serotypes 1, 2, 4, and 5 with or without Pluronics F88 (A) and AAV-CAG-GFP of serotypes 6, 7, 8, and 9 (B). Blue, nuclei. Arrows indicate transduced adipocytes. Original magnification 100× (B, left panel) and 200× (A; B, right panel). C. GFP content in eWAT treated with AAV-CAG-GFP of serotypes 1, 6, 7, 8, or 9 (n=5 per group). Values shown are means±SEM. RLU, relative light units. D. In toto X-gal staining of eWAT receiving AAV8-CMV-LacZ. X-gal staining was distributed throughout the transduced eWAT. In contrast, no X-gal staining was detected in eWAT from animals treated with saline solution. E. Relative mHKII expression levels in isolated adipocytes obtained from eWAT of animals treated with AAV9-CMV-mHKII or AAV9-CMV-null vectors. F. Basal and insulin-stimulated 2-[1-$^3$H]deoxy-D-glucose uptake by isolated adipocytes from mice injected with AAV9-CMV-null and AAV9-CMV-mHKII. Adipocytes were obtained from at least 5 mice/group. G. Immunostaining against GFP (brown) in sections of inguinal white adipose tissue (iWAT) two weeks after the intra-iWAT administration of $2\times10^{11}$ vg of AAV8 or AAV9-CAG-GFP vectors. Original magnification ×100. H: GFP expression levels in iWAT two weeks post-injection of $2\times10^{11}$ vg of AAV8 or AAV9-CAG-GFP (n=6). Values shown are means±SEM. *$p<0.05$, $p<0.01$ and *$p<0.001$; #$p<0.05$ vs AAV9-CMV-null at the same insulin concentration. All analyses were performed two weeks after intra-eWAT administration of $2\times10^{11}$ vg/eWAT.
Figure 1:
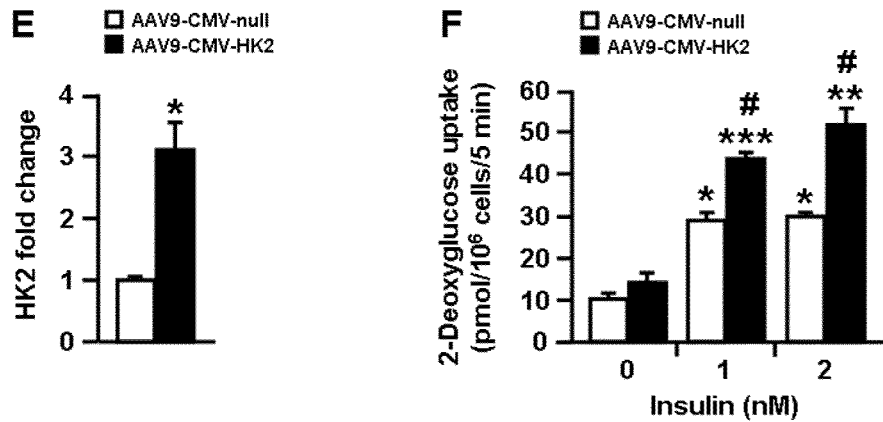
Figure 1:
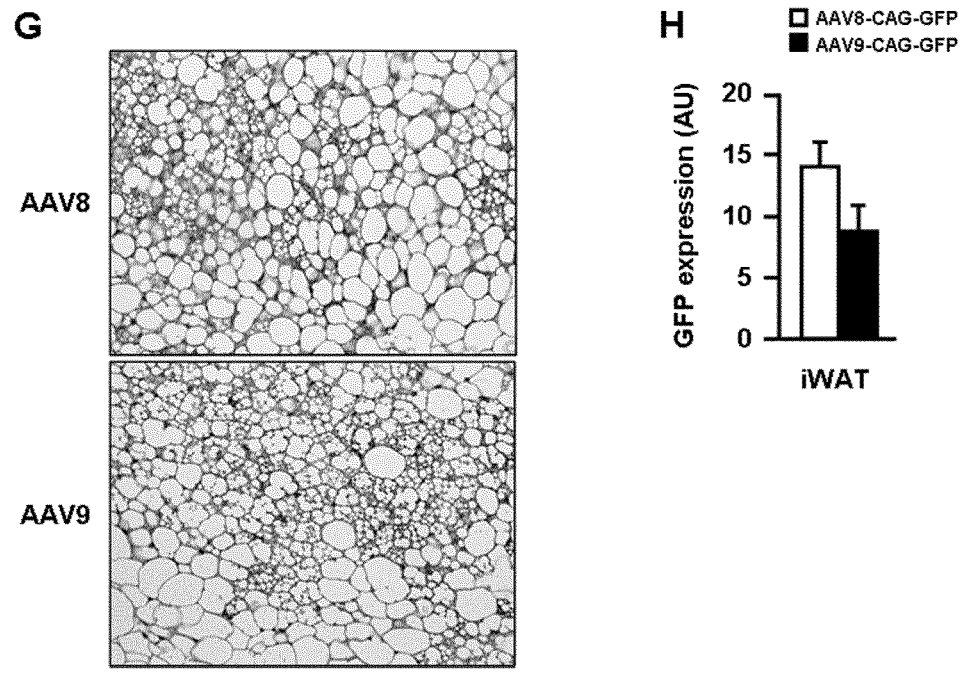
Figure 2:
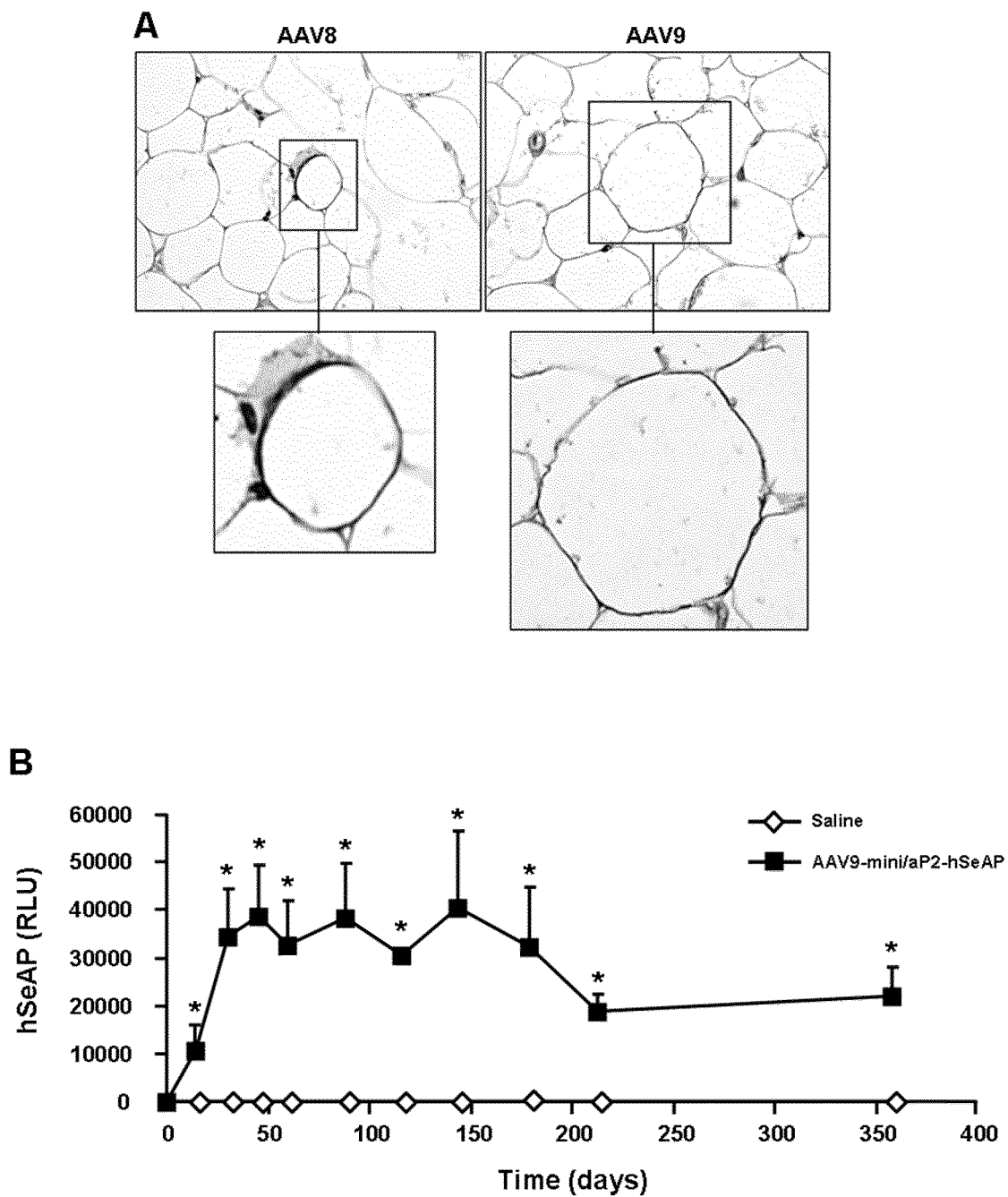
FIG. 2. Specific transduction of white adipocytes after intra-eWAT administration of AAV by means of the mini/aP2 regulatory region. A. Immunostaining against GFP (in brown) in eWAT receiving $10^{12}$ vg/eWAT of AAV8 and AAV9-mini/aP2-GFP vectors. Analysis was performed two weeks post-injection. Original magnification ×400. B. Circulating hSeAP levels. A dose of $4\times10^{12}$ vg/mouse of AAV9-mini/aP2-hSeAP vectors was injected bilaterally into eWAT and measurement of circulating hSeAP levels was performed at several time points post-injection. RLU, relative light units. Values shown are means±SEM. n=3 (saline) and n=4 (AAV9-mini/aP2-SeAP). C. Relative hSeAP expression levels in liver and eWAT one year after intra-eWAT administration of $4\times10^{12}$ vg/mouse of AAV9-mini/aP2-hSeAP. D. In vivo 2-[1-$^3$H]deoxy-D-glucose uptake by eWAT, iBAT, and heart was evaluated two weeks after intra-eWAT administration of AAV9-mini/aP2-null and AAV9-mini/aP2-mHKII vectors ($1.4.\times10^{12}$ vg/mouse). Values shown are means±SEM. n=7 mice per group. *$p<0.05$.
Figure 2:
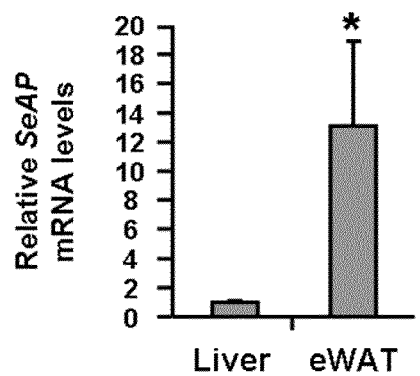
Figure 2:
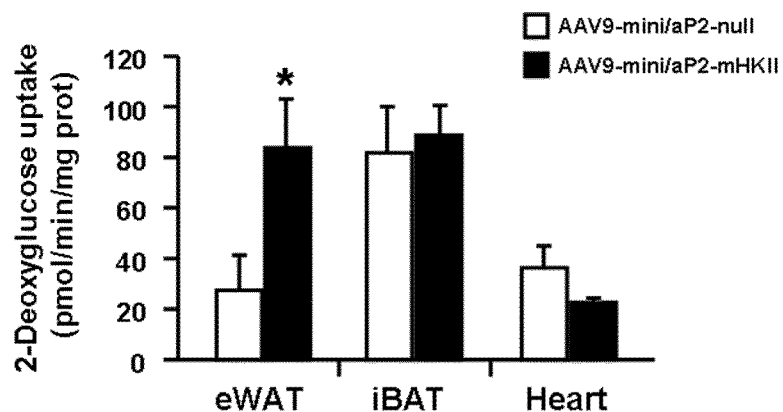
Figure 3:
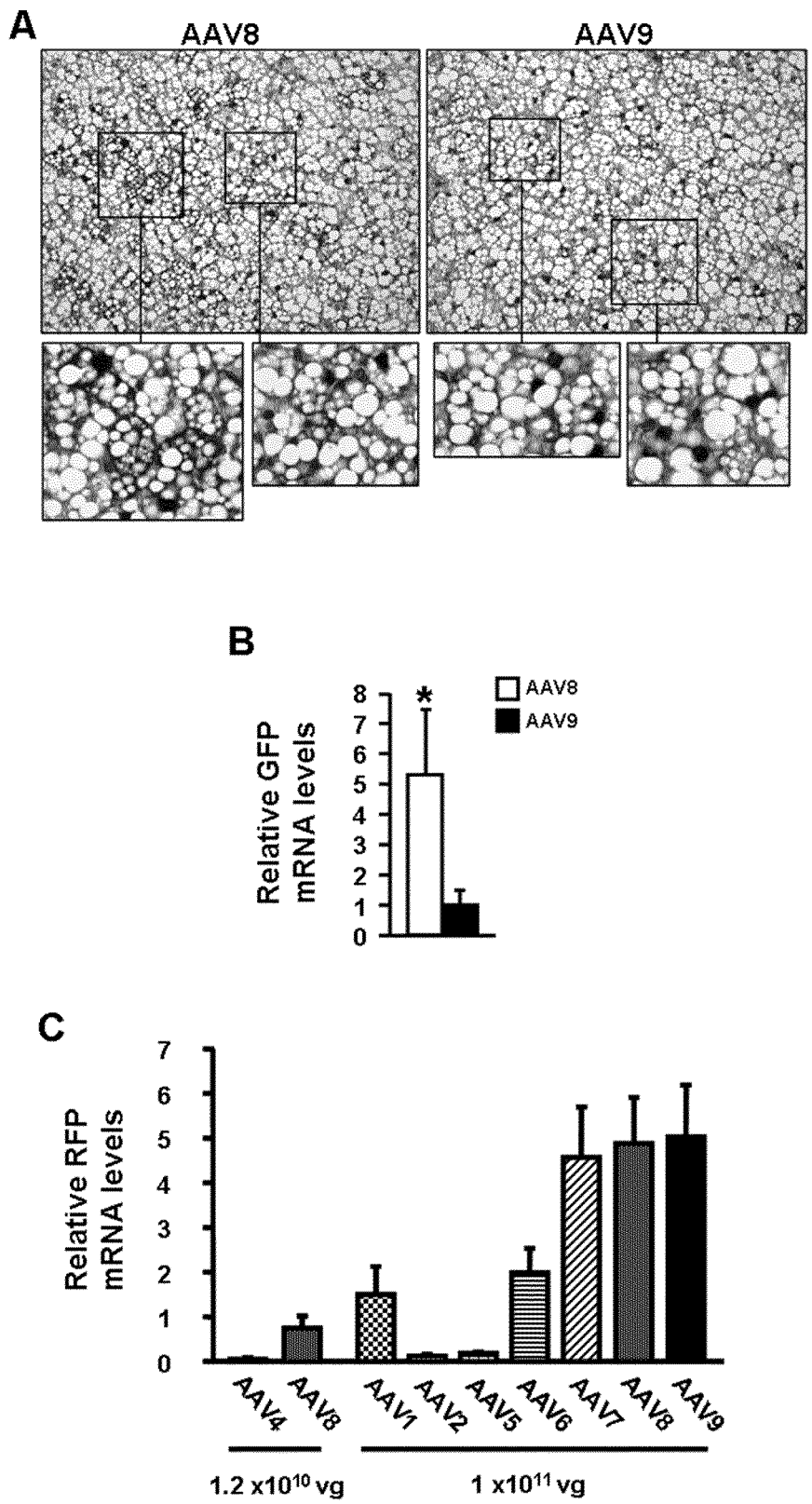
FIG. 3. Transduction of brown adipocytes by intra-iBAT administration of AAV. A. Immunostaining against GFP (in brown) in sections of iBAT treated with $2\times10^9$ vg/mouse of AAV8 or AAV9-CAG-GFP. Original magnification ×200 and ×400 (insets). B. Relative GFP expression levels in iBAT receiving $2\times10^9$ vg/mouse of AAV8 or AAV9-CAG-GFP. Values shown are means±SEM. n=5 mice per group. *$p<0.05$. C. Relative red fluorescent protein (RFP) expression levels in iBAT receiving $2\times10^{10}$ vg/mouse of AAV4 or AAV8-CMV-RFP or $2\times10^{10}$ vg/mouse of AAV1, AAV2, AAV5, AAV6, AAV7, AAV8, or AAV9-CMV-RFP. The transduction patterns are similar to eWAT. See FIG. 1. AAV6, AAV7, AAV8, and AAV9 are the most efficient serotypes for transducing iBAT. D. Immunostaining against RFP (in brown) in sections of iBAT treated with $10^{11}$ vg/mouse of AAV9-CMV-RFP. Original magnification ×200 and ×400 (insets). Analyses were performed two weeks post administration of AAV.
Figure 3:
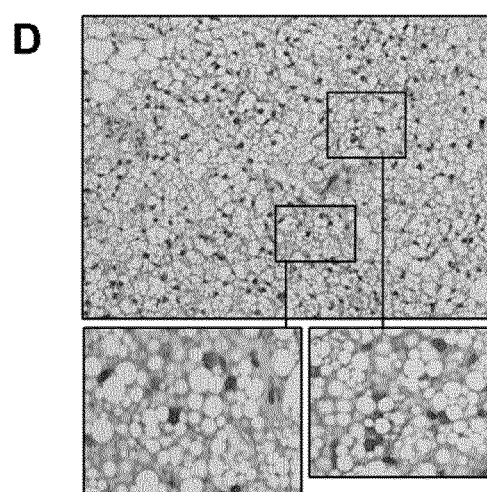
Figure 4:
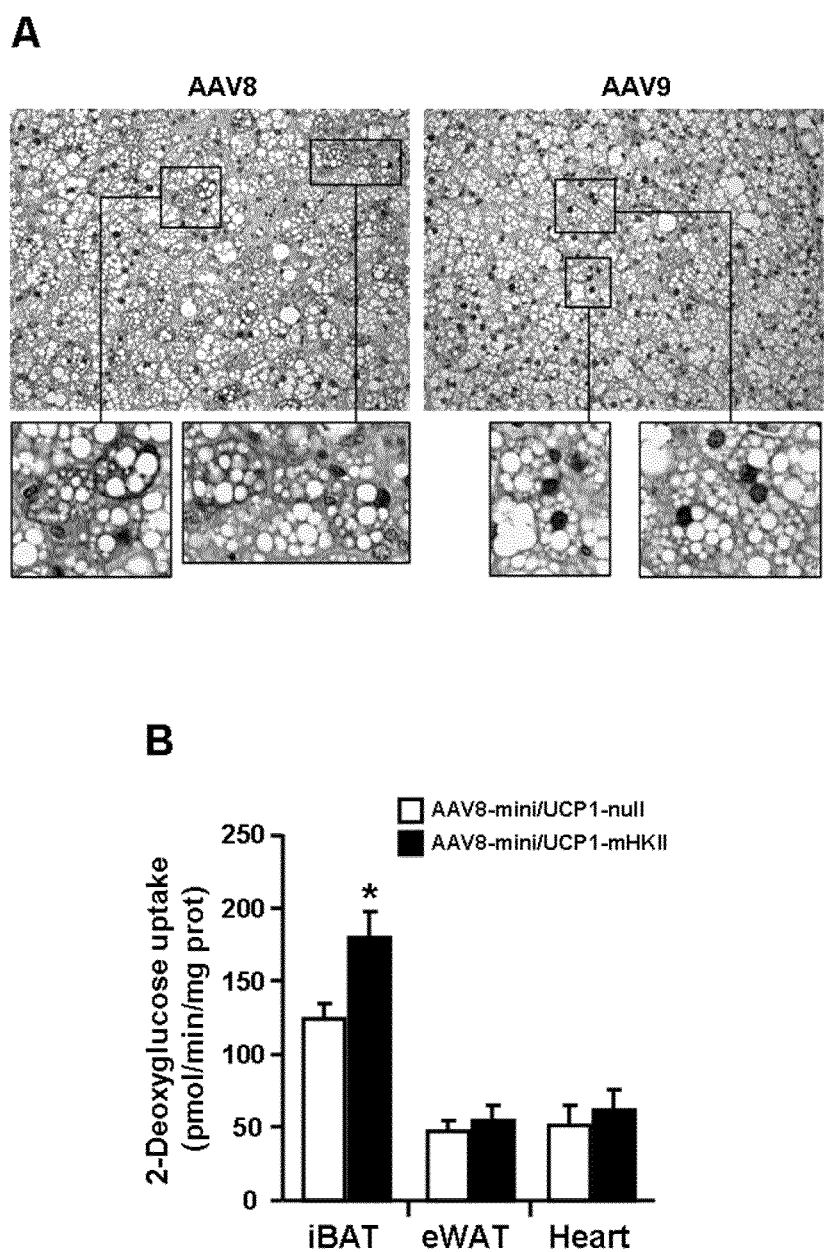
FIG. 4. Specific transduction of brown adipocytes after intra-iBAT administration of AAV by means of the mini/UCP1 regulatory region. A. Transduction of brown adipocytes was evaluated by immunostaining against GFP (in brown) two weeks post-injection of $2\times10^{11}$ vg/mouse of AAV8 or AAV9-mini/UCP1-GFP vectors. Original magnification ×200 and ×400 (insets). B. In vivo 2-[1-$^3$H]deoxy-D-glucose uptake by iBAT, eWAT and heart at two weeks after administration of AAV8-mini/UCP1-null and AAV8-mini/UCP1-mHKII vectors ($7\times10^{10}$ vg/mouse). n=6 (AAV8-mini/UCP1-mHKII) and n=10 (AAV8-mini/UCP1-null) mice per group. C-E. Relative mVEGF$_{164}$ (C), total mVEGF (D), and mPECAM1 (E) expression levels in iBAT two weeks after the delivery of $2\times10^{11}$ vg/mouse of AAV9-mini/UCP1-mVEGF$_{164}$ or AAV9-mini/UCP1-null vectors. n=5 mice per group. F. Immunostaining against α-SMA (in brown) in iBAT two weeks post-injection of $2\times10^{11}$ vg/mouse of AAV9-mini/UCP1-mVEGF$_{164}$ or AAV9-mini/UCP1-null vectors. Original magnification ×400. Values shown are means±SEM. *$p<0.05$. Red arrowheads indicate capillary structures.
Figure 4:
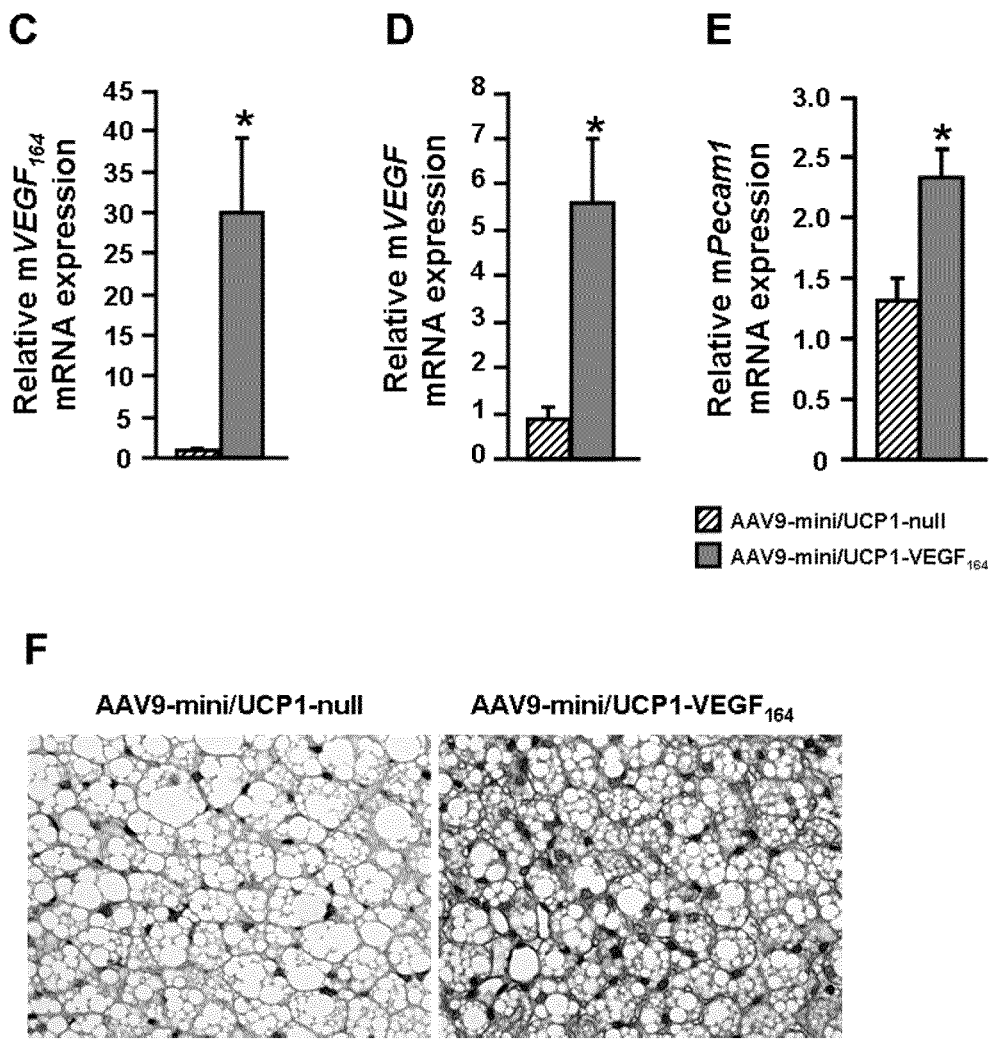
Figure 5:
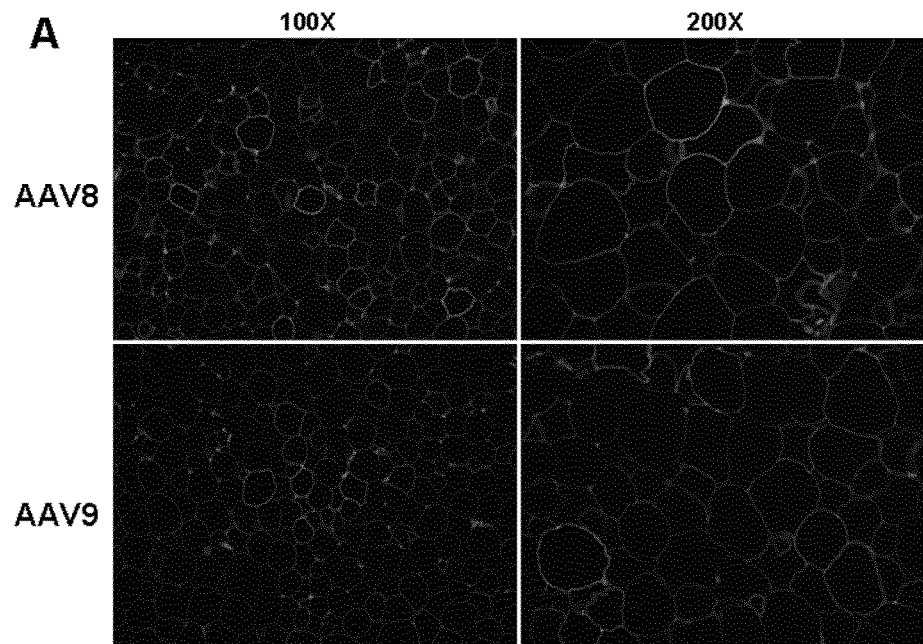
FIG. 5. Transduction of white and brown adipocytes by systemic delivery of AAV vectors to lean mice. A. Immunostaining against GFP (in green) in eWAT sections. Blue, nuclei. Original magnification ×100 (left panel) and ×200 (right panel). B. Relative GFP expression levels in eWAT. C. GFP content in eWAT. D. Immunostaining against GFP (in brown) in iBAT sections. Original magnification ×200 and ×400 (insets). E. Relative GFP expression levels in iBAT. F. GFP content in iBAT. G-H. Relative GFP expression levels in inguinal (iWAT), retroperitoneal (rWAT), mesenteric (mWAT), eWAT and iBAT following iv administration of vectors to ICR mice (G) and C57B16 mice (H) (ICR: n=3 for AAV8 and n=5 for AAV9; C57B16: n=4). All analyses were performed two weeks after the tail vein administration of $5\times10^{12}$ vg/mouse of AAV8 or AAV9-CAG-GFP vectors. AU, arbitrary units. RLU, relative light units.
Figure 5:
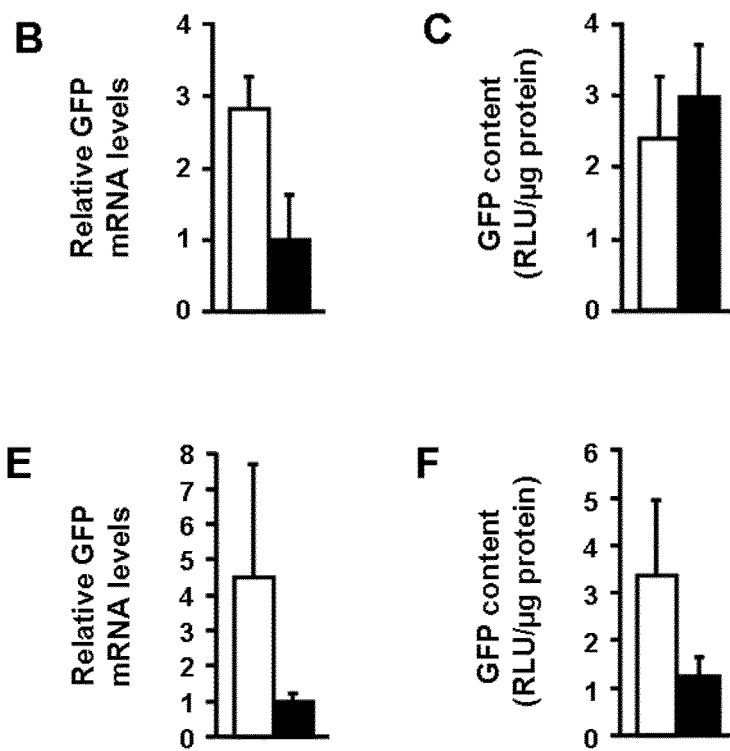
Figure 5:
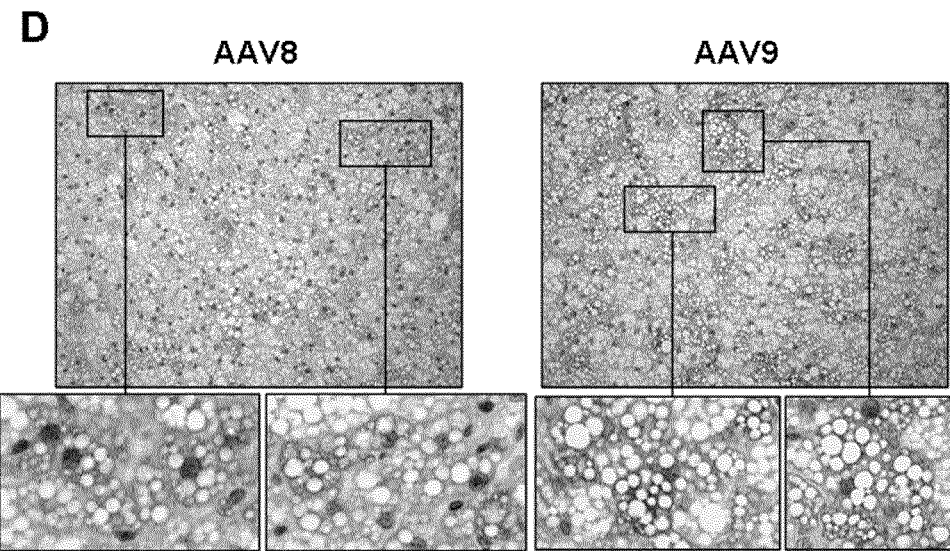
Figure 5:
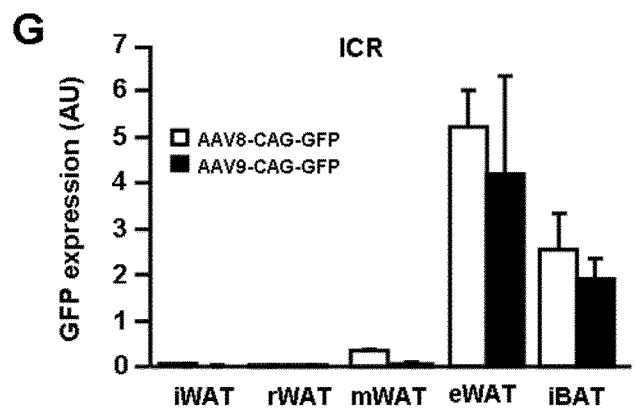
Figure 5:
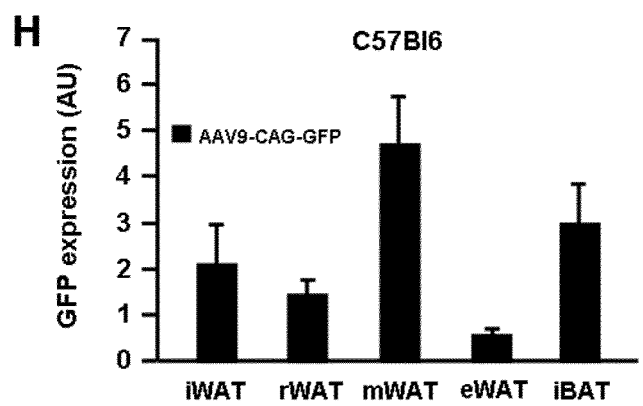
Figure 9:
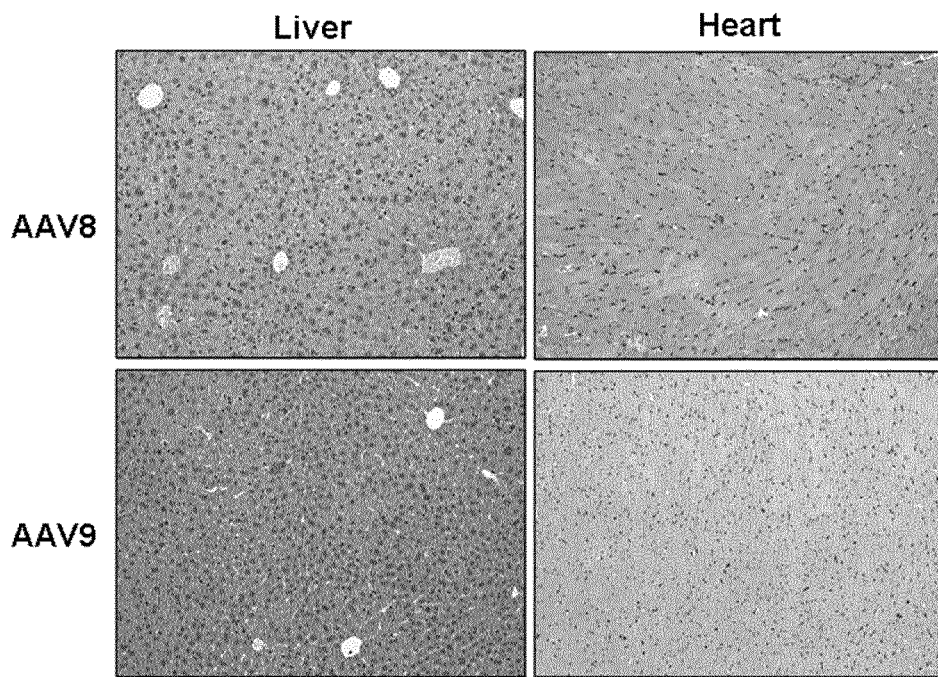
FIG. 9. Adipose tissue restricted AAV-mediated transgene expression by means of the mini/aP2 regulatory region. No GFP expression was detected by immunostaining against GFP in the liver and heart two weeks after the local intra-eWAT administration of $10^{12}$ vg of AAV8 and AAV9-mini/aP2-GFP vectors. Original magnification ×100.
Figure 11:
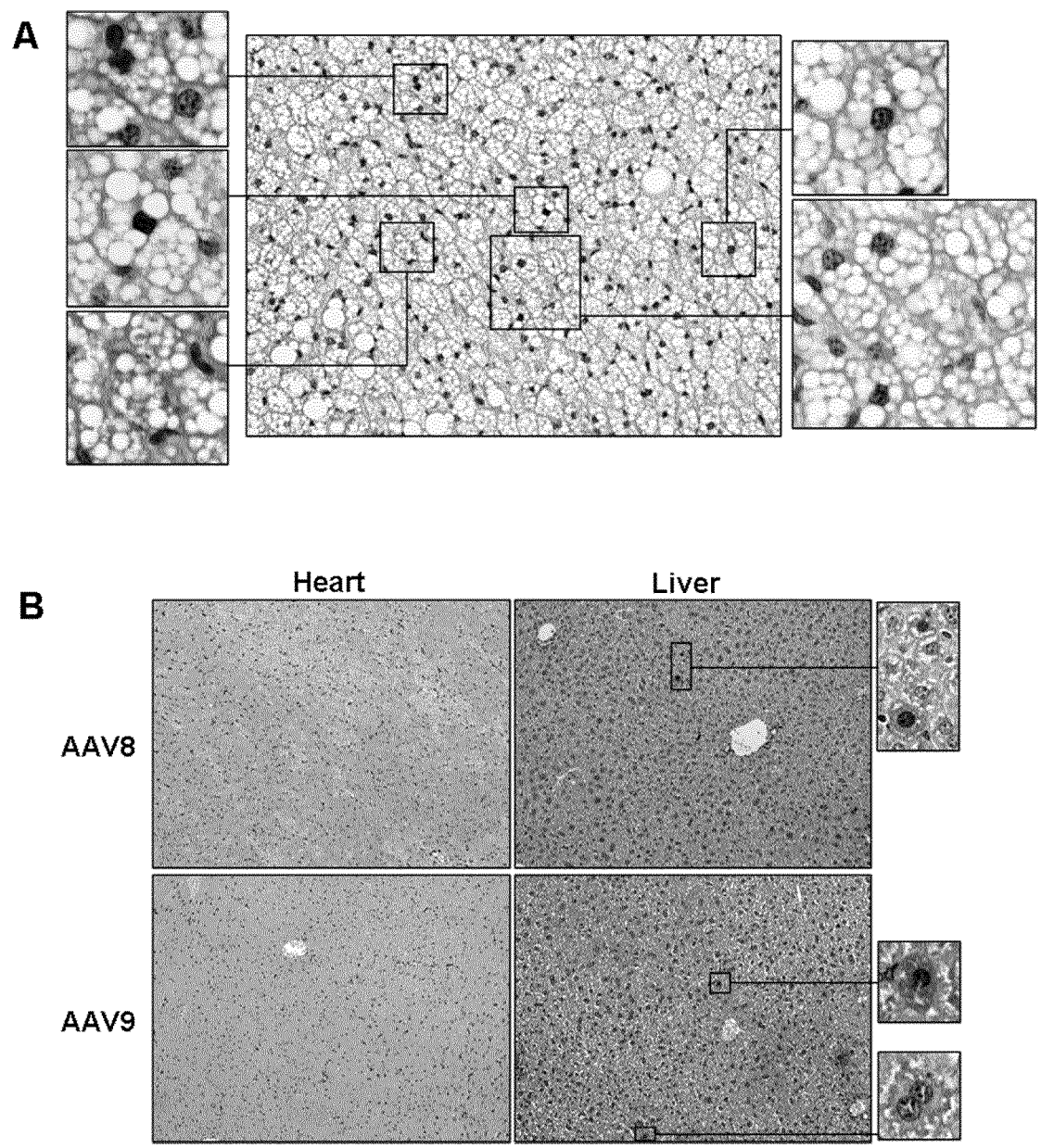
FIG. 11. Transduction of brown adipocytes by means of the mini/aP2 regulatory region and adipose-restricted transgene expression after intra-iBAT administration of AAV. A. Transduction of brown adipocytes was evaluated by immunostaining against GFP (in brown) two weeks after intra-iBAT delivery of $2×10^{11}$ vg/mouse of AAV9-mini/aP2-GFP vectors. Original magnification ×200 and ×400 (insets). B. Transduction of non-adipose organs was evaluated by immunostaining against GFP (in brown) two weeks post-injection of AAV8 or AAV9-mini/UCP1-GFP vectors ($2×10^{11}$ vg/mouse) locally into iBAT. GFP expression was marginal in liver. Original magnification ×100 and ×400 (insets).

The present invention discloses vectors based on the AAV6, AAV7, AAV8, and AAV9 serotypes of the adeno-associated virus capable of mediating efficiently gene transfer to WAT or BAT when administered locally. See FIGS. 1B and 1C and 3A-3D. The systemic administration of these vectors also leads to an efficient gene delivery in both WAT and BAT. See FIGS. 5A and 5D. Although gene delivery mediated by AAV8 and AAV9 vectors is efficient, it is not restricted to adipose tissue. The present invention discloses that the combination of AAV8 and AAV9 vectors with adipose-tissue specific promoter regions allows the specific expression of polynucleotides of interest in adipose tissue. In particular, the local administration of AAV8 or AAV9 vectors comprising an expression cassette wherein an heterologous gene (e.g. GFP) is under the control of the mini/aP2 regulatory region leads to its expression in WAT with no expression in the liver and heart. See FIGS. 2A and 9. In addition, the local administration of AAV8 or AAV9 vectors comprising an expression cassette wherein an heterologous gene (e.g. GFP) is under the control of the mini/UCP1 regulatory region leads to its expression in BAT with no heart expression and only marginal liver expression. See FIGS. 4A and 11B. Thus, the local administration of the combinations formed by the vectors and promoters of the invention provides a safe mechanism for treating many diseases based on the transduction of adipose cells in vivo.

Figure 6:
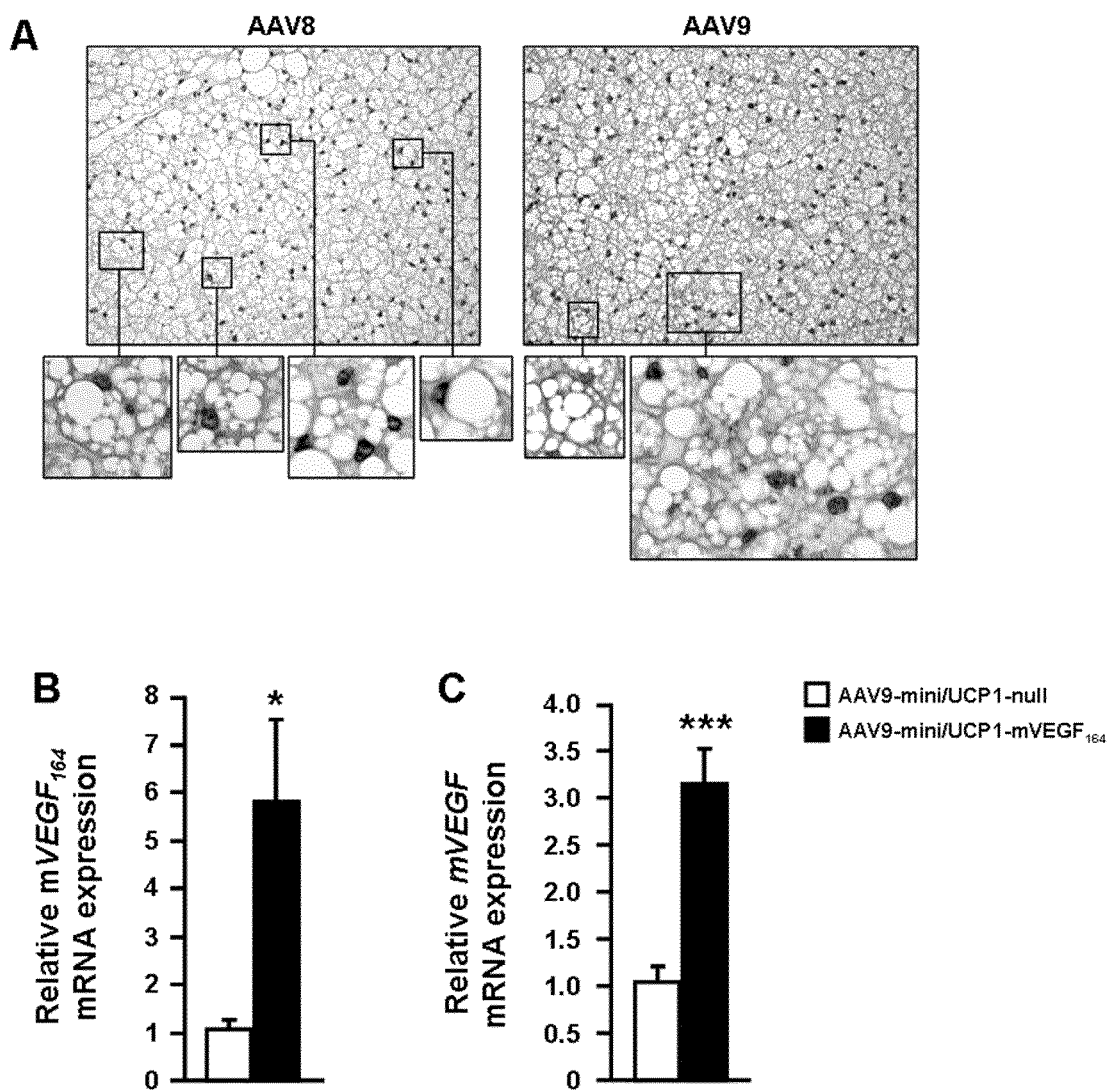
FIG. 6. Specific transduction of brown adipocytes after systemic administration of AAV by means of the mini/UCP1 regulatory region. A. Immunostaining against GFP (in brown) in iBAT receiving AAV8 or AAV9-mini/UCP1-GFP vectors. Original magnification ×200 and ×400 (insets). B-C. Relative mVEGF$_{164}$ (B) and total mVEGF (C) expression levels in iBAT treated with $2\times10^{12}$ vg/mouse AAV9-mini/UCP1-mVEGF$_{164}$ or AAV9-mini/UCP1-null vectors two months post-injection. D-E. VEGF164 (B) and PECAM1 (C) expression levels in iBAT one month after the iv administration of $8\times10^{12}$ vg of AAV9-mini/UCP1-VEGF164 or AAV9-mini/UCP1-null vectors (n=5). F-G. Immunostaining against CD105 (brown) (D) and α-SMA (brown) (E) in the same cohorts as in B-C. Red arrowheads indicate vessels. Original magnification ×400 and FIG. 7. Transduction of adipocytes by means of the mini/aP2 regulatory region and adipose-restricted transgene expression after systemic administration of AAV. A. Transduction of brown adipocytes was evaluated by immunostaining against GFP (in brown) in iBAT sections from animals receiving AAV8 or AAV9-mini/aP2-GFP vectors. Original magnification ×200 and ×400 (insets). B-C. Transduction of non-adipose tissues was evaluated by immunostaining against GFP (in brown) two weeks post-injection. GFP expression was minimal in the liver and absent in the heart of animals treated with AAV8 or AAV9-mini/aP2-GFP (B) and AAV8 or AAV9-mini/UCP1-GFP (C). Original magnification ×100 and ×400 (insets). All analyses were performed two weeks post systemic injection of $2\times10^{12}$ vg/mouse.
Figure 6:
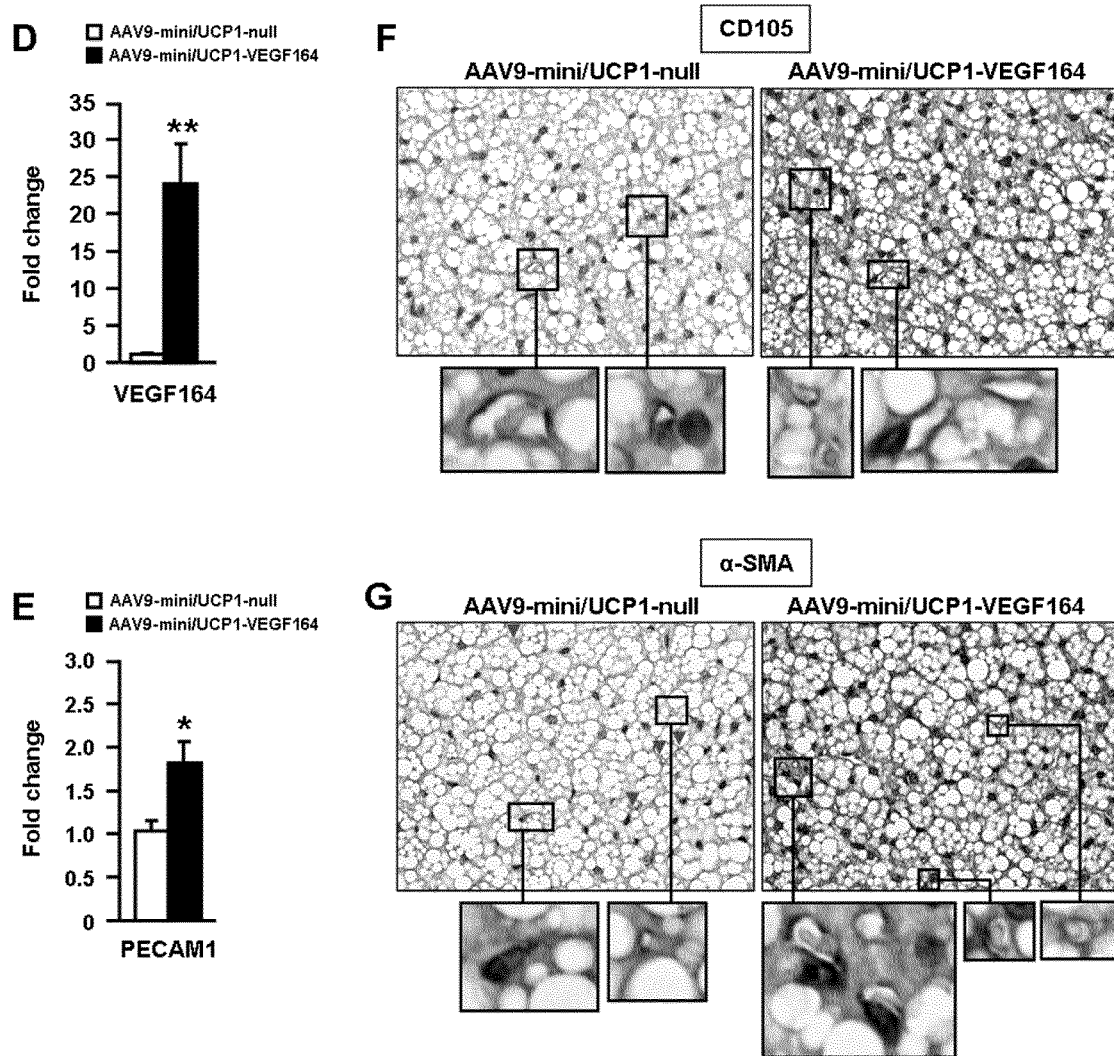
Figure 7:
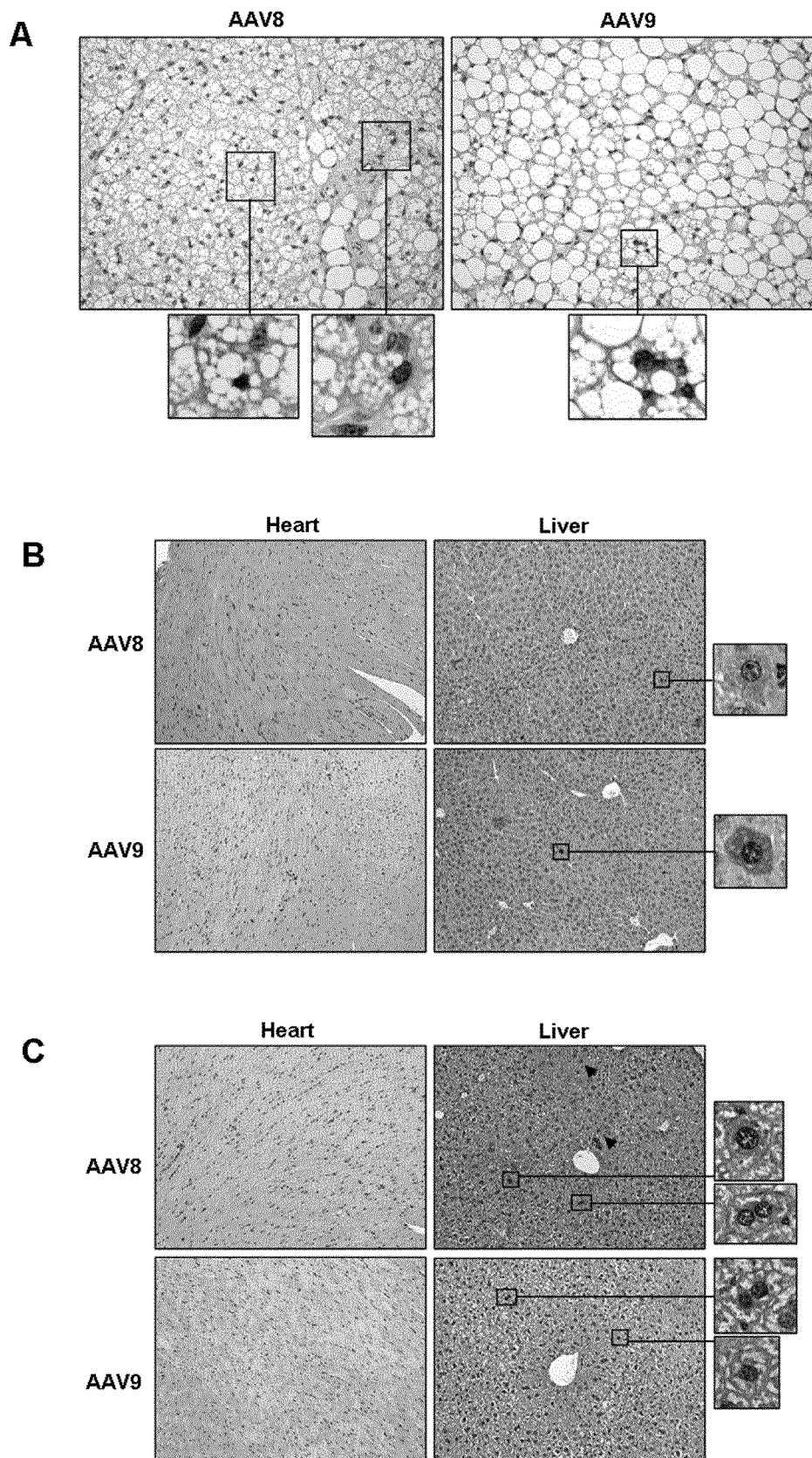

Moreover, the systemic administration of the combinations of the invention constitutes an alternative approach for the transduction of adipose cells. In this regard, the present invention discloses that the systemic administration of AAV8 or AAV9-mini/UCP1 and the AAV8 or AAV9-mini/aP2 combinations is effective for transducing BAT and WAT, respectively. See FIGS. 6A and 7A. Regardless of which of the two regulatory regions is used, the systemic administration of the combinations of the invention leads to highly restricted expression of the polynucleotides of interest in adipose tissue, with no expression in heart and merely marginal expression in the liver. See FIGS. 7B and 7C.

1. Definition of General Terms and Expressions

The terms "adeno-associated virus", "AAV virus", "AAV virion", "AAV viral particle", and "AAV particle", as used interchangeably herein, refer to a viral particle composed of at least one AAV capsid protein (preferably by all of the capsid proteins of a particular AAV serotype) and an encapsidated polynucleotide AAV genome. If the particle comprises a heterologous polynucleotide (i.e. a polynucleotide other than a wild-type AAV genome such as a transgene to be delivered to a mammalian cell) flanked by the AAV inverted terminal repeats, it is typically referred to as an "AAV vector particle" or "AAV vector". AAV refers to viruses belonging to the genus Dependovirus of the Parvoviridae family. The AAV genome is approximately 4.7 kilobases long and is composed of single-stranded deoxyribonucleic acid (ssDNA) which may be either positive- or negative-sensed. The genome comprises inverted terminal repeats (ITRs) at both ends of the DNA strand, and two open reading frames (ORFs): rep and cap. The rep frame is made of four overlapping genes encoding Rep proteins required for the AAV life cycle. The cap frame contains overlapping nucleotide sequences of capsid proteins: VP1, VP2 and VP3, which interact together to form a capsid of an icosahedral symmetry. See Carter B, Adeno-associated virus and adeno-associated virus vectors for gene delivery, Lassic D, et al., Eds., "Gene Therapy: Therapeutic Mechanisms and Strategies" (Marcel Dekker, Inc., New York, N.Y., US, 2000) and Gao G, et al., J. Virol. 2004; 78(12):6381-6388.

The term "adeno-associated virus ITRs" or "AAV ITRs", as used herein, refers to the inverted terminal repeats present at both ends of the DNA strand of the genome of an adeno-associated virus. The ITR sequences are required for efficient multiplication of the AAV genome. Another property of these sequences is their ability to form a hairpin. This characteristic contributes to its self-priming which allows the primase-independent synthesis of the second DNA strand. The ITRs were also shown to be required for both integration of the wild-type AAV DNA into the host cell genome (i.e. 19$^{th}$ chromosome in humans) and rescue from it, as well as for efficient encapsidation of the AAV DNA combined with generation of a fully assembled, deoxyribonuclease-resistant AAV particles.

The term "AAV2", as used herein, refers to a serotype of adeno-associated virus with a genome sequence as defined in the GenBank accession number NC001401.

The term "AAV vector", as used herein, further refers to a vector comprising one or more polynucleotides of interest (or transgenes) that are flanked by AAV terminal repeat sequences (ITRs). Such AAV vectors can be replicated and packaged into infectious viral particles when present in a host cell that has been transfected with a vector encoding and expressing rep and cap gene products (i.e. AAV Rep and Cap proteins), and wherein the host cell has been transfected with a vector which encodes and expresses a protein from the adenovirus open reading frame E4orf6. When an AAV vector is incorporated into a larger polynucleotide (e.g. in a chromosome or in another vector such as a plasmid used for cloning or transfection), then the AAV vector is typically referred to as a "pro-vector". The pro-vector can be "rescued" by replication and encapsidation in the presence of AAV packaging functions and necessary helper functions provided by E4orf6.

The term "adipose tissue", as used herein, refers to tissue composed of mature adipocytes (i.e. fat cells) and a combination of small blood vessels, nerve tissue, lymph nodes and the stromal vascular fraction (SVF). The SVF is composed of endothelial cells, fibroblasts, adipocyte precursor cells (i.e. preadipocytes), and immune cells such as macrophages and T cells. In mammals, two different types of adipose tissues are (BAT). Adipose tissue functions primarily to store energy in the form of fat, to generate heat via non-shivering thermogenesis, and to secrete adipokines.

The term "adipose tissue cell" or "adipocyte", as used herein, refers to the cell types that compose adipose tissue and that are specialized in storing energy as fat or generating heat via non-shivering thermogenesis and secreting adipokines. Adipose tissue cells include white adipocytes and brown adipocytes.

The term "adipose tissue-specific transcriptional regulatory region", as used herein, refers to a nucleic acid sequence that serves as a promoter (i.e. regulates expression of a selected nucleic acid sequence operably linked to the promoter), and which affects the expression of a selected nucleic acid sequence in specific tissue cells, such as adipocytes. The adipose tissue-specific transcriptional regulatory region can be constitutive or inducible.

The term "alkaline phosphatase" or "AP", as used herein, refers to an enzyme (EC 3.1.3.1) which catalyzes the hydrolysis of phosphate groups from many types of molecules, including nucleotides, proteins, and alkaloids.

The term "angiogenesis", as used herein, refers to the process of formation of new blood vessels from other pre-existing ones, and includes the processes of vasculogenesis and arteriogenesis.

The term "arteriogenesis", as used herein, refers to the formation, growth or development of blood vessels with a smooth muscle media layer.

The term "brown adipose tissue cell" or "brown adipocyte", as used herein, refers to the type of adipocyte that is polygonal and characterized by the accumulation of lipids into multiple smaller "multilocular" droplets and by their high content of large mitochondria packed with laminar cristae within the cytoplasm. Unlike white adipocytes, these cells have considerable cytoplasm. The nucleus is round, and, although eccentrically located, it is not in the periphery of the cell. The numerous mitochondria of the brown adipocytes and the rich vascularity of the brown adipose depots are the main reasons for the brown color of BAT. Brown adipocytes are located in classical BAT depots and are responsible for heat generation via non-shivering thermogenesis. See Enerback S, N. Engl. J. Med. 2009; 360:2021-2023.

The term "CAG regulatory region", as used herein, refers to the combination formed by the cytomegalovirus early enhancer element and the chicken β-actin promoter. See Alexopoulou A, et al., BMC Cell Biology 2008; 9(2):1-11.

The term "cap gene" or "AAV cap gene", as used herein, refers to a gene that encodes a Cap protein. The term "Cap protein", as used herein, refers to a polypeptide having at least one functional activity of a native AAV Cap protein (e.g. VP1, VP2, VP3). Examples of functional activities of Cap proteins (e.g. VP1, VP2, VP3) include the ability to induce formation of a capsid, facilitate accumulation of single-stranded DNA, facilitate AAV DNA packaging into capsids (i.e. encapsidation), bind to cellular receptors, and facilitate entry of the virion into host.

The term "capsid", as used herein, refers to the structure in which the viral genome is packaged. A capsid consists of several oligomeric structural subunits made of proteins. For instance, AAV have an icosahedral capsid formed by the interaction of three capsid proteins: VP1, VP2 and VP3.

The term "cell composition", as used herein, refers to a material composite comprising the adipocytes of the invention and at least another component. The composition may be formulated as a single formulation or may be presented as separate formulations of each of the components, which may be combined for joint use as a combined preparation. The composition may be a kit-of-parts wherein each of the components is individually formulated and packaged.

The term "constitutive promoter", as used herein, refers to a promoter whose activity is maintained at a relatively constant level in all cells of an organism, or during most developmental stages, with little or no regard to cell environmental conditions.

The term "enhancer", as used herein, refers to a DNA sequence element to which transcription factors bind to increase gene transcription.

The term "expression cassette", as used herein, refers to a nucleic acid construct, generated recombinantly or synthetically, with a series of specified nucleic acid elements, which permit transcription of a particular nucleic acid in a target cell.

The term "genes providing helper functions", as used herein, refers to genes encoding polypeptides which perform functions upon which AAV is dependent for replication (i.e. "helper functions"). The helper functions include those functions required for AAV replication including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpesvirus (other than herpes simplex virus type-1), and vaccinia virus. Helper functions include, without limitation, adenovirus E1, E2a, VA, and E4 or herpesvirus UL5, UL8, UL52, and UL29, and herpesvirus polymerase.

The term "hexokinase" or "HK", as used herein, refers to an enzyme that catalyzes the phosphorylation of hexoses to form hexose phosphate. In most organisms, glucose is the main substrate of HK, and glucose-6-phosphate is the most important product.

The term "high blood pressure" or "arterial hypertension", as used herein, refers to a medical condition in which the blood pressure of the arteries is elevated. Blood pressure involves two measurements, systolic and diastolic, which depend on whether the heart muscle is contracting (systole) or relaxed between beats (diastole). Normal blood pressure at rest is within the range of 100-140 mmHg systolic (top reading) and 60-90 mmHg diastolic (bottom reading). High blood pressure is said to be present if it is persistently at or above 140/90 mmHg. Hypertension is classified as either primary (essential) hypertension or secondary hypertension; about 90-95% of cases are categorized as "primary hypertension" which means high blood pressure with no obvious underlying medical cause. The remaining 5-10% of cases (i.e. secondary hypertension) is caused by other conditions that affect the kidneys, arteries, heart or endocrine system. Insulin resistance, which is common in obesity, is also thought to contribute to hypertension. Hypertension is a major risk factor for stroke, myocardial infarction (i.e. heart attack), heart failure, aneurysms of the arteries (e.g. aortic aneurysm), peripheral arterial disease and is a cause of chronic kidney disease. Even moderate elevation of arterial blood pressure is associated with a shortened life expectancy.

The term "hyperglycemia", as used herein, refers to a state where abnormally high blood glucose levels appear in relation to the fasting baseline levels. In particular, hyperglycaemia is understood to take place when fasting blood glucose levels are consistently higher than 126 mg/dL, the postprandial glucose levels are higher than 140 mg/dL, or the glucose levels in venous plasma 2 hours after administration of a dose of glucose of 1.75 grams for each kilogram of body weight is over 200 mg/dL.

The term "insulin resistance", as used herein, refers to a disorder wherein cells do not respond correctly to insulin. As a result, the body produces more insulin in response to high blood glucose levels. Patients with insulin resistance frequently display high glucose levels and high circulating insulin levels. Insulin resistance is frequently linked to obesity, hypertension, and hyperlipidemia. Additionally, insulin resistance frequently appears in patients with type 2 diabetes.

The term "locally administered", as used herein, means that the polynucleotides, vectors, polypeptides, or pharmaceutical compositions of the invention are administered to the subject at or near a specific site.

The term "obesity", as used in the present invention, relates to the definition of obesity provided by the WHO based on the body mass index (BMI), which consists of the ratio between the weight of a person (in kg) and the square of their height in meters. According to this criteria, a BMI lower than 18.5 kg/m² is considered as insufficient weight or thinness, a BMI of 18.5-24.9 kg/m² is considered a normal weight, a BMI of 25.0-29.9 kg/m² is considered grade 1 of overweight, a BMI of 30.0-39.0 kg/m² is considered a grade 2 of overweight and a BMI greater than or equal to 40.0 kg/m² is considered morbid obesity. Alternatively, there are other methods for defining the degree of obesity of a subject, such as the diameter of the waist measured at the midpoint between the lower limit of the ribs and the upper limit of the pelvis (in cm), the thickness of skin folds, and bioimpedance, based on the principle that a lean mass transmits electricity better than a fatty mass.

The term "operably linked", as used herein, refers to the functional relation and location of a promoter sequence with respect to a polynucleotide of interest (e.g. a promoter or enhancer is operably linked to a coding sequence if it affects the transcription of the sequence). Generally, a promoter operably linked is contiguous to the sequence of interest. However, an enhancer does not have to be contiguous to the sequence of interest to control its expression.

The terms "pharmaceutically acceptable carrier," "pharmaceutically acceptable diluent," "pharmaceutically acceptable excipient", or "pharmaceutically acceptable vehicle", used interchangeably herein, refer to a non-toxic solid, semisolid, or liquid filler, diluent, encapsulating material, or formulation auxiliary of any conventional type. A pharmaceutically acceptable carrier is essentially non-toxic to recipients at the employed dosages and concentrations and is compatible with other ingredients of the formulation. The number and the nature of the pharmaceutically acceptable carriers depend on the desired administration form. The pharmaceutically acceptable carriers are known and may be prepared by methods well known in the art. See Faulí i Trillo C, "Tratado de Farmacia Galenica" (Ed. Luzán 5, S.A., Madrid, ES, 1993) and Gennaro A, Ed., "Remington: The Science and Practice of Pharmacy" 20th ed. (Lippincott Williams & Wilkins, Philadelphia, Pa., US, 2003).

The term "promoter", as used herein, refers to a nucleic acid fragment that functions to control the transcription of one or more polynucleotides, located upstream the polynucleotide sequence(s), and which is structurally identified by the presence of a binding site for DNA-dependent RNA polymerase, transcription initiation sites, and any other DNA sequences including, but not limited to, transcription factor binding sites, repressor, and activator protein binding sites, and any other sequences of nucleotides known in the art to act directly or indirectly to regulate the amount of transcription from the promoter. A "tissue-specific" promoter is only active in specific types of differentiated cells or tissues.

The term "polynucleotide", as used herein, refers to a nucleic acid molecule, either DNA or RNA, containing deoxyribonucleotides or ribonucleotides. The nucleic acid may be double stranded, single stranded, or contain portions of both double stranded or single stranded sequence. The term "polynucleotide" includes, but is not limited to, nucleic acid sequences with the capacity to encode a polypeptide and nucleic acid sequences partially or totally complementary to an endogenous polynucleotide of the cell or subject treated therewith so that following the transcription thereof, it generates an RNA molecule (e.g. microRNA, shRNA, siRNA) capable of hybridizing and inhibiting the expression of the endogenous polynucleotide.

The term "post-transcriptional regulatory region", as used herein, refers to any polynucleotide that facilitates the expression, stabilization, or localization of the sequences contained in the cassette or the resulting gene product.

The terms "prevent," "preventing," and "prevention", as used herein, refer to inhibiting the inception or decreasing the occurrence of a disease in a subject. Prevention may be complete (e.g. the total absence of pathological cells in a subject) or partial. Prevention also refers to a reduced susceptibility to a clinical condition.

The term "recombinant viral genome", as used herein, refers to an AAV genome in which at least one extraneous expression cassette polynucleotide is inserted into the naturally occurring AAV genome.

The term "rep gene" or "AAV rep gene", as used herein, refers to a gene that encodes a Rep protein. The term "Rep protein", as used herein, refers to a polypeptide having at least one functional activity of a native AAV Rep protein (e.g. Rep 40, 52, 68, 78). A "functional activity" of a Rep protein (e.g. Rep 40, 52, 68, 78) is any activity associated with the physiological function of the protein, including facilitating replication of DNA through recognition, binding and nicking of the AAV origin of DNA replication as well as DNA helicase activity. Additional functions include modulation of transcription from AAV (or other heterologous) promoters and site-specific integration of AAV DNA into a host chromosome.

The term "subject", as used herein, refers to an individual, plant, or animal, such as a human beings, a non-human primate (e.g. chimpanzees and other apes and monkey species), a farm animal (e.g. birds, fish, cattle, sheep, pigs, goats, and horses), a domestic mammal (e.g. dogs and cats), or a laboratory animal (e.g. rodents, such as mice, rats and guinea pigs). The term does not denote a particular age or sex. The term "subject" encompasses an embryo and a fetus.

The term "systemically administered" and "systemic administration", as used herein, means that the polynucleotides, vectors, polypeptides, or pharmaceutical compositions of the invention are administered to a subject in a non-localized manner. The systemic administration of the polynucleotides, vectors, polypeptides, or pharmaceutical compositions of the invention may reach several organs or tissues throughout the body of the subject or may reach specific organs or tissues of the subject. For example, the intravenous administration of a pharmaceutical composition of the invention may result in the transduction of more than one tissue or organ in a subject.

The term "transcriptional regulatory region", as used herein, refers to a nucleic acid fragment capable of regulating the expression of one of more genes. The regulatory regions of the polynucleotides of the invention include a promoter and an enhancer.

The term "transduce" or "transduction", as used herein, refers to the process whereby a foreign nucleotide sequence is introduced into a cell via a viral vector.

The term "transfection", as used herein, refers to the introduction of DNA into a recipient eukaryotic cell.

The term "treat" or "treatment", as used herein, refers to the administration of a compound or composition of the invention to control the progression of a disease after its clinical signs have appeared. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state, and remission (both partial and total). The control of progression of the disease also involves an extension of survival, compared with the expected survival if treatment is not applied.

The term "type 2 diabetes", as used herein, refers to a disease characterized by an inappropriate increase in blood glucose levels. The chronic hyperglycemia of diabetes is associated with long-term damage, dysfunction, and failure of different organs leading to a variety of complications such as retinopathy, nephropathy, and peripheral neuropathy. Type 2 diabetes is caused by insulin resistance in peripheral tissues (principally skeletal muscle, adipose tissue, and liver) and inappropriate compensatory insulin secretion response, due to the combination of decreased β-cell mass and function. In addition to increasing glucose concentration, faulty insulin action frequently translates into an increase in cholesterol or triglyceride levels.

The term "vasculogenesis", as used herein, refers to the formation, growth, development, or proliferation of blood vessels derived from undifferentiated or underdifferentiated cells.

The term "vector", as used herein, refers to a construct capable of delivering, and optionally expressing, one or more polynucleotides of interest into a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. The vectors can be stable and can be self-replicating. There are no limitations regarding the type of vector that can be used. The vector can be a cloning vector, suitable for propagation and for obtaining polynucleotides, gene constructs or expression vectors incorporated to several heterologous organisms. Suitable vectors include prokaryotic expression vectors (e.g. pUC18, pUC19, Bluescript and their derivatives), mp18, mp19, pBR322, pMB9, ColE1, pCR1, RP4, phages and shuttle vectors (e.g. pSA3 and pAT28), and eukaryotic expression vectors based on viral vectors (e.g. adenoviruses, adeno-associated viruses as well as retroviruses and lentiviruses), as well as non-viral vectors such as pSilencer 4.1-CMV (Ambion®, Life Technologies Corp., Carslbad, Calif., US), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1.

The term "VEGF", as used herein, means vascular endothelial growth factor. "VEGF" includes, but is not limited to, the VEGF variants A, B, C, D, E, and F. See Hamawy A, et al., Curr. Opin. Cardiol. 1999; 14:515-522, Neufeld G, et al., Prog. Growth Factor Res. 1994; 5:89-97, Olofsson B, et al., Proc. Natl. Acad. Sci. USA 1996; 93:2576-2581, Chilov D, et al., J. Biol. Chem. 1997; 272: 25176-25183, and Olofsson B, et al., Curr. Opin. Biotechnol. 1999; 10:528-535. The VEGF A variant includes, but is not limited to, isoforms $VEGF_{164}$, $VEGF_{121}$, $VEGF_{145}$, $VEGF_{167}$, $VEGF_{165}$, $VEGF_{189}$, and $VEGF_{206}$. See Tischer E, et al., J. Biol. Chem. 1991; 266:11947-11954 and Poltorak Z, et al., J. Biol. Chem. 1997; 272:7151-7158. The term "VEGF" also includes the vascular permeability factor or vasculotropin (VPF). See Keck P, et al., Science 1989; 246:1309-1312 and Senger D, et al., Science 1983; 219: 983-985. VPF is currently known in the art as VEGF A. Other members of the VEGF family can also be used, including placental growth factors PIGF I and II. The sequences of suitable VEGFs are readily available via National Center for Biotechnology Information, http://www.ncbi.nlm.nih.gov/ June 2012). For example, the loci for human VEGF family members include: VEGF-A-P15692 and NP003367; VEGF-B-NP003368, P49765, AAL79001, AAL79000, AAC50721, AAB06274, and AAH08818; VEGF-C-NP005420, P49767, S69207, AAB36425, and CAA63907; VEGF-D-NP004460, AAH27948, O43915, CAA03942, and BAA24264; VEGF-E-AAQ88857; VEGF-F-2VPFF; PIGF-1-NP002623, AAH07789, AAH07255, AAH01422, P49763, CAA38698, and CAA70463; synthetic constructs of Chain A-1FZVA and Chain B-1FZVB of PIGF-1; and PIGF-2-AAB25832 and AAB30462. Preferably, VEGF is of human origin. However, VEGF from other species, such as mouse, may also be used according to the invention.

The term "white adipose tissue cell" or "white adipocyte", as used herein, refers to the type of adipocyte that is polyhedral to spherical and that contains a large "unilocular" lipid droplet surrounded by a thin layer of cytoplasm. The nucleus of said cells is flattened and located on the periphery. The diameter of white adipocytes is variable, ranging between 30 and 70 μm according to depot site. The fat stored is in a semi-liquid state, and is composed primarily of triglycerides and cholesteryl ester. White adipocytes secrete many peptides and proteins collectively known as adipokines, such as resistin, adiponectin, and leptin.

The term "Woodchuck hepatitis virus posttranscriptional regulatory element" or "WPRE", as used herein, refers to a DNA sequence that, when transcribed, creates a tertiary structure capable of enhancing the expression of a gene. See Lee Y, et al., Exp. Physiol. 2005; 90(1):33-37 and Donello J, et al., J. Virol. 1998; 72(6):5085-5092.

The term "microRNAs" or "miRNAs", as used herein, are small (~22-nt), evolutionarily conserved, regulatory RNAs involved in RNA-mediated gene silencing at the post-transcriptional level. See Bartel DP. Cell 2004; 116: 281-297. Through base pairing with complementary regions (most often in the 3' untranslated region (3'UTR) of cellular messenger RNA (mRNA)), miRNAs can act to suppress mRNA translation or, upon high-sequence homology, cause the catalytic degradation of mRNA. Because of the highly differential tissue expression of many miRNAs, cellular miRNAs can be exploited to mediate tissue-specific targeting of gene therapy vectors. By engineering tandem copies of target elements perfectly complementary to tissue-specific miRNAs (miRT) within viral vectors, transgene expression in undesired tissues can be efficiently inhibited.

2. Adeno-Associated Viral Vectors which Provide Adipose-Tissue Specific Expression In a first aspect, the invention relates to an adeno-associated viral (AAV) vector comprising a recombinant viral genome wherein said recombinant viral genome comprises an expression cassette comprising an adipose tissue-specific transcriptional regulatory region operatively linked to a polynucleotide of interest.

AAV according to the present invention include any serotype of the 42 serotypes of AAV known. In general, serotypes of AAV have genomic sequences with a significant homology at the level of amino acids and nucleic acids, provide an identical series of genetic functions, produce virions that are essentially equivalent in physical and functional terms, and replicate and assemble through practically identical mechanisms. In particular, the AAV of the present invention may belong to the serotype 1 of AAV (AAV1), AAV2, AAV3 (including types 3A and 3B), AAV4, AAV5, AAV6, AAV7, AAV8, AAV9, AAV10, AAV11, avian AAV, bovine AAV, canine AAV, equine AAV, ovine AAV, and any other AAV. Examples of the sequences of the different AAV serotypes may be found in the literature or in public databases such as GenBank. See GenBank accession numbers AF028704.1 (AAV6), NC006260 (AAV7), NC006261 (AAV8), and AX753250.1 (AAV9). In a preferred embodiment, the adeno-associated viral vector of the invention is of a serotype selected from the group consisting of the AAV6, AAV7, AAV8, and AAV9 serotypes.

The genome of the AAV according to the invention typically comprises the cis-acting 5' and 3' inverted terminal repeat sequences and an expression cassette. See Tijsser P, Ed., "Handbook of Parvoviruses" (CRC Press, Boca Raton, Fla., US, 1990, pp. 155-168). The ITR sequences are about 145 bp in length. Preferably, substantially the entire sequences encoding the ITRs are used in the molecule, although some degree of minor modification of these sequences is permissible. Procedures for modifying these ITR sequences are known in the art. See Brown T, "Gene Cloning" (Chapman & Hall, London, GB, 1995), Watson R, et al., "Recombinant DNA", 2nd Ed. (Scientific American Books, New York, N.Y., US, 1992), Alberts B, et al., "Molecular Biology of the Cell" (Garland Publishing Inc., New York, N.Y., US, 2008), Innis M, et al., Eds., "PCR Protocols. A Guide to Methods and Applications" (Academic Press Inc., San Diego, Calif., US, 1990), Erlich H, Ed., "PCR Technology. Principles and Applications for DNA Amplification" (Stockton Press, New York, N.Y., US, 1989), Sambrook J, et al., "Molecular Cloning. A Laboratory Manual" (Cold Spring Harbor Laboratory Press, Cold Spring Harbor, N.Y., US, 1989), Bishop T, et al., "Nucleic Acid and Protein Sequence. A Practical Approach" (IRL Press, Oxford, GB, 1987), Reznikoff W, Ed., "Maximizing Gene Expression" (Butterworths Publishers, Stoneham, Mass., US, 1987), Davis L, et al., "Basic Methods in Molecular Biology" (Elsevier Science Publishing Co., New York, N.Y., US, 1986), and Schleef M, Ed., "Plasmid for Therapy and Vaccination" (Wiley-VCH Verlag GmbH, Weinheim, DE, 2001). In a preferred embodiment, the AAV recombinant genome comprises the 5' and 3' AAV ITRs. In another embodiment, the 5' and 3' AAV ITRs derive from AAV2. In a still more preferred embodiment, the AAV recombinant genome lacks the rep open reading frame or the cap open reading frame. In one embodiment, the AAV2 ITRs are selected to generate a pseudotyped AAV (i.e. an AAV having a capsid and ITRs derived from different serotypes).

The polynucleotide of the invention can comprise ITRs derived from any one of the AAV serotypes. In a preferred embodiment, the ITRs are derived from the AAV2 serotype.

The AAV of the invention comprises a capsid from any serotype. In particular embodiment, the capsid is derived from the AAV of the group consisting on AAV1, AAV2, AAV4, AAV5, AAV6, AAV7, AAV8 and AAV9. In a preferred embodiment, the AAV of the invention comprises a capsid derived from the AAV8 or AAV9 serotypes. In a further preferred embodiment, the VP1 sequence of the AAV capsid has SEQ ID NO. 18. See GenBank accession number AY530579.

In some embodiments, an AAV Cap for use in the method of the invention can be generated by mutagenesis (i.e. by insertions, deletions, or substitutions) of one of the aforementioned AAV Caps or its encoding nucleic acid. In some embodiments, the AAV Cap is at least 70%, 75%, 80%, 85%, 90%, 95%, 98%, or 99% or more similar to one or more of the aforementioned AAV Caps.

In some embodiments, the AAV Cap is chimeric, comprising domains from two, three, four, or more of the aforementioned AAV Caps. In some embodiments, the AAV Cap is a mosaic of VP1, VP2, and VP3 monomers originating from two or three different AAV or a recombinant AAV. In some embodiments, a rAAV composition comprises more than one of the aforementioned Caps.

In some embodiments, an AAV Cap for use in a rAAV composition is engineered to contain a heterologous sequence or other modification. For example, a peptide or protein sequence that confers selective targeting or immune evasion may be engineered into a Cap protein. Alternatively or in addition, the Cap may be chemically modified so that the surface of the rAAV is polyethylene glycolated (i.e. pegylated), which may facilitate immune evasion. The Cap protein may also be mutagenized (e.g. to remove its natural receptor binding, or to mask an immunogenic epitope).

In another particular embodiment, the AAV vector is a pseudotyped AAV vector (i.e. the vector comprises sequences or components originating from at least two distinct AAV serotypes). In a particular embodiment, the pseudotyped AAV vector comprises an AAV genome derived from one AAV serotype (e.g. AAV2), and a capsid derived at least in part from a distinct AAV serotype. Specific examples of such pseudotyped AAV vectors include, without limitation, vectors comprising a genome derived from any AAV serotype (e.g. from AAV1 to AAV11), in an AAV6, AAV7, AAV8, or AAV9-derived capsid.

In one embodiment the AAV vector contains one promoter with the addition of at least one target sequence of at least one miRNA which can be selected from the following list: miR122 (miRBase database accession number MI0000442), miR152 (MI0000462), miR199 (MI0000242), miR215 (MI0000291), miR192 (MI0000234), miR148a (MI0000253), miR194 (MI0000488), miR1 (MI0000651), miRT133 (MI0000450), miR206 (MI0000490), miR208 (MI0000251), miR124 (MI0000443), miR125 (MI0000469), miR216 (MI0000292), miR130 (MI0000448). Sequence references have been obtained from the miRBase (http://www.mirbase.org/, according to version as of Jul. 31, 2013).

In one embodiment the AAV vector contains one promoter with the addition of at least one miRNA target sequence which can be selected from the following list:

---
List 1

```
miRT122a  (5'CAAACACCATTGTCACACTCCA3'), miRT152   (5'AGTCACGTACTGTCTTGAACC3'), miR199a-5p (5'GGGTCACAAGTCTGATGGACAAG3'), miR99a-3p  (5'TGTCATCAGACGTGTAACCAAT3'), miRT215   (5'TACTGGATACTTAACTGTCTG3'), miRT192   (5'GGCTGTCAATTCATAGGTCAG3'), miRT194   (5'ACATTGTCGTTGAGGTACACCT3'), miRT1     (5'TTACATACTTCTTTACATTCCA3'), mirT148   (5'AGTCACGTGATGTCTTGAAACA3'), miRT133a  (5'AAACCAGGGGAAGTTGGTCGAC3'), miRT206   (5'ACCTTACATTCCTTCACACACC3'), miRT124   (5'ATTCCGTGCGCCACTTACGG3'), miRT125   (5'AGGGACTCTGGGAAATTGGACACT3'), miRT216   (5'ATTAGAGTCGACCGTTGACACT3'), miRT130   (5'GTCACGTTACAATTTTCCCGTA3').
```
---

In one embodiment the AAV vector contains one promoter with the addition of at least one miRNA target sequence having an homology of 85% with a miRNA target sequence selected from the above-mentioned List 1.

In one embodiment the AAV vector contains one promoter with the addition of at least one miRNA target sequence which is a functional equivalent with a miRNA target sequence selected from the above-mentioned List 1. In this case, the term functional equivalent means any nucleotide sequence capable to bind the same miRNAs that bind the original sequence. For example, a functional equivalent of miRT122a is any sequence that hybridizes with the same number of miRNAs that would hybridize with miRT122a. The nucleotide sequence of the functional equivalent retains the relevant biological activity of a reference mirT sequence. That means that a functional equivalent of a mirT would have the ability to inhibit the transgene expression in undesired tissues, in the same way that the reference mirT sequence does.

In another particular embodiment, the miRNA target sequence can be selected from mirT122a (5'CAAACAC-CATTGTCACACTCCA3') referred as SEQ ID NO: 19 or mirT1 (5'TTACATACTTCTTTACATTCCA3') referred as SEQ ID NO: 20.

The transcriptional regulatory region may comprise a promoter and, optionally, an enhancer region. Preferably, the promoter is specific for adipose tissue. The enhancer need not be specific for adipose tissue. Alternatively, the transcriptional regulatory region may comprise an adipose tissue-specific promoter and an adipose tissue-specific enhancer.

In one embodiment, the tissue-specific promoter is an adipocyte-specific promoter such as, for example, the adipocyte protein 2 (aP2, also known as fatty acid binding protein 4 (FABP4)), the PPARy promoter, the adiponectin promoter, the phosphoenolpyruvate carboxykinase (PEPCK) promoter, the promoter derived from human aromatase cytochrome p450 (p450arom), or the Foxa-2 promoter. See Graves R, et al., Genes Dev. 1991; 5:428-437, Ross S, et al., Proc. Natl. Acad. Sci. USA 1990; 87:9590-9594, Simpson E, et al., U.S. Pat. No. 5,446,143, Mahendroo M, et al., J. Biol. Chem. 1993; 268:19463-19470, Simpson E, et al., Clin. Chem. 1993; 39:317-324, and Sasaki H, et al., Cell 1994; 76: 103-115. In a preferred embodiment, the enhancer region is selected from the group consisting of the adipose-specific aP2 enhancer and the adipose-specific UCP1 enhancer.

In a preferred embodiment, the adipose-tissue specific regulatory region of the AAV according to the invention comprises the adipose-specific aP2 enhancer and the basal aP2 promoter. See Rival Y, et al., J. Pharmacol. Exp. Ther. 2004: 311(2):467-475. The region comprising the adipose-specific aP2 enhancer and the basal aP2 promoter is also known as "mini/aP2 regulatory region" and is formed by the basal promoter of the aP2 gene and the adipose-specific enhancer of said aP2 gene. Preferably, the aP2 promoter is murine. See Graves R, et al., Mol. Cell Biol. 1992; 12(3): 1202-1208 and Ross S, et al., Proc. Natl. Acad. Sci. USA 1990; 87:9590-9594. In a particular embodiment, the mini/aP2 regulatory region has the sequence SEQ ID NO: 2.

In another preferred embodiment, the adipose-tissue specific regulatory region of the AAV according to the invention comprises the adipose-specific UCP1 enhancer and the basal UCP1 promoter. See del Mar Gonzalez-Barroso M, et al., J. Biol. Chem. 2000; 275(41): 31722-31732 and Rim J, et al., J. Biol. Chem. 2002; 277(37):34589-34600. The region comprising the adipose-specific UCP1 enhancer and the basal UCP1 promoter is also known as "mini/UCP regulatory region" and refers to a combination of the basal promoter of the UCP1 gene and the adipose-specific enhancer of said UCP1 gene. Preferably, a rat UCP1 promoter is used. See Larose M, et al., J. Biol. Chem. 1996; 271(49):31533-31542 and Cassard-Doulcier A, et al., Biochem. J. 1998; 333:243-246. In a particular embodiment, the mini/UCP1 regulatory region has the sequence SEQ ID NO: 3.

In another embodiment, the expression cassette which forms part of the AAV of the invention further comprises expression control sequences including, but not limited to, appropriate transcription sequences (i.e. initiation, termination, promoter, and enhancer), efficient RNA processing signals (e.g. splicing and polyadenylation (polyA) signals), sequences that stabilize cytoplasmic mRNA, sequences that enhance translation efficiency (i.e. Kozak consensus sequence), sequences that enhance protein stability, and when desired, sequences that enhance secretion of the encoded product. A great number of expression control sequences, including promoters which are native, constitutive, inducible, or tissue-specific are known in the art and may be utilized according to the present invention.

In another embodiment, the expression cassette which forms part of the AAV of the invention further comprises a post-transcriptional regulatory region. In a preferred embodiment, the post-transcriptional regulatory region is the Woodchuck Hepatitis Virus post-transcriptional region (WPRE) or functional variants and fragments thereof and the PPT-CTS or functional variants and fragments thereof. See Zufferey R, et al., J. Virol. 1999; 73:2886-2892 and Kappes J, et al., WO 2001/044481. In a particular embodiment, the post-transcriptional regulatory region is WPRE.

The expression cassette which forms part of the AAV according to the invention comprises a "polynucleotide of interest". In a preferred embodiment, the polynucleotide of interest encodes a protein which acts systemically. In another embodiment, the polynucleotide of interest encodes a protein which acts upon or in the vicinity of an adipocyte. In a preferred embodiment, the protein which acts upon or in the vicinity of said adipocyte is hexokinase (HK), including any of the four mammalian HK isozymes (EC 2.7.1.1) that vary in subcellular locations and kinetics with respect to different susbtrates. By way of an example, HK includes HK1 (GenBank accession numbers NP000179, NP277031, NP277032, NP277033, NP277035), HK2 (GenBank accession number NP000180), HK3 (GenBank accession number NP002106) and HK4 or glucokinase (GenBank accession numbers NP000153, NP277042, NP277043). In another preferred embodiment, the HK is glucokinase, which is used herein interchangeably with hexokinase 4 or HK4, and refers to an isoform of hexokinase with a Km for glucose a 100 times higher than HK1, HK2, or HK3.

In an embodiment, the protein which acts upon or in the vicinity of said adipocyte is an alkaline phosphatase (AP), including but not limited to, the intestinal-type or IAP (GenBank accession number NP001622), the placental type or PLAP (GenBank accession number NP001623), and the tissue-nonspecific isozyme or ALPL (GenBank accession numbers NP000469, NP001120973.2. and NP001170991.1). In another embodiment, the protein which acts upon or in the vicinity of said adipocyte is VEGF including, but not limited to, the VEGF variants A, B, C, D, E, and F.

In another embodiment, the polynucleotide of interest encodes a polypeptide which is normally produced and secreted by the adipocytes. In another embodiment, the polypeptide which is produced and secreted by adipocytes is an adipsin (e.g. especially an adipsin that is a serine protease homolog), adiponectin, leptin, resistin, or a protein product of the ob gene.

Still other useful polynucleotides of interest include those coding hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-1 and TGF-II), any one of the transforming growth factor a superfam y, including TGFa, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog, and tyrosine hydroxylase.

Other useful polynucleotides of interest include those coding proteins that regulate the immune system including, without limitation, cytokines and lymphokines such as thrombopoietin (TPO), interleukins (IL) IL-1 through IL-25 (e.g. IL-2, IL-4, IL-12, and IL-18), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC and HLA molecules, as well as engineered immunoglobulins and MHC and HLA molecules. Useful gene products also include complement regulatory proteins such as complement regulatory proteins, membrane cofactor protein (MCP), decay accelerating factor (DAF), CR1, CF2, and CD59.

Still other useful polynucleotides of interest include those coding any one of the receptors for the hormones, growth factors, cytokines, lymphokines, regulatory proteins and immune system proteins. The invention encompasses receptors for cholesterol regulation or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, vitamin D receptors, and other nuclear receptors. In addition, useful gene products include transcription factors such as jun, fos, max, mad, serum response factor (SRF), AP1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins (e.g. GATA-3), and the forkhead family of winged helix proteins.

Other useful polynucleotides of interest include those coding enzymes such as carbamoyl synthetase I, ornithine transcarbamylase, arginosuccinate synthetase, arginosuccinate lyase, arginase, fumarylacetacetate hydrolase, phenylalanine hydroxylase, α-1 antitrypsin, glucose-6-phosphatase, porphobilinogen deaminase, cystathione β-synthase, branched chain ketoacid decarboxylase, albumin, isovaleryl-coA dehydrogenase, propionyl CoA carboxylase, methyl malonyl CoA mutase, glutaryl CoA dehydrogenase, insulin, β-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product (e.g. a mini- or micro-dystrophin). Still other useful gene products include enzymes useful in replacement therapy such as, for example, enzymes that contain mannose-6-phosphate for the treatment of lysosomal storage diseases (e.g. a suitable gene encoding β-glucuronidase (GUSB)).

The packaging size limit of AAV vectors is limited to the size of the parent wild-type AAV genome, which ranges in size based on the AAV serotype (i.e. from 4,087 to 4,767). See Wu Z, et al., Mol. Ther. 2010; 7(1):80-86. For example, wild-type AAV-2 has a genome size of 4,679 and wild-type AAV-6 has a genome size of 4,683. In some embodiments, the cloning capacity of the recombinant RNA vector may be limited and a desired coding sequence may involve the complete replacement of the virus's 4.8 kilobase genome. Large genes may, therefore, not be suitable for use in a standard recombinant AAV vector, in some cases. The skilled artisan will appreciate that options are available in the art for overcoming a limited coding capacity. For example, the AAV ITRs of two genomes can anneal to form head to tail concatamers, almost doubling the capacity of the vector. Insertion of splice sites allows for the removal of the ITRs from the transcript. Other options for overcoming a limited cloning capacity will be apparent to the skilled artisan.

3. Therapeutic Methods Based on the Tropism of AAV6, AAV7, AAV8 and AAV9 for the Adipose Tissue In a second aspect, the present invention discloses adeno-associated viral vectors of the AAV6, AAV7, AAV8, and AAV9 serotypes capable of transducing adipose tissue cells efficiently. This feature makes possible the development of methods for the treatment of diseases which require or may benefit from the expression of a polynucleotide of interest in adipocytes. In particular, this finding facilitates the delivery of polypeptides of interest to a subject in need thereof by administering the AAV vectors of the invention to the patient, thus generating adipocytes capable of expressing the polynucleotide of interest and its encoded polypeptide in vivo. If the encoded polypeptide is a secreted polypeptide, it can be secreted by adipocytes, allowing the systemic delivery of the polypeptide in such a way.

Thus, in another embodiment, the invention provides an adeno-associated viral vector comprising a recombinant viral genome wherein said recombinant viral genome comprises an expression cassette comprising a transcriptional regulatory region operatively linked to a polynucleotide of interest wherein the serotype of the AAV is selected from the group consisting of AAV6, AAV7, AAV8, and AAV9 for use in the treatment or prevention of a disease that requires the expression of the polynucleotide of interest.

In another embodiment, the invention provides an adeno-associated viral vector comprising a recombinant viral genome wherein said recombinant viral genome comprises an expression cassette comprising an adipose tissue-specific transcriptional regulatory region operatively linked to a polynucleotide of interest for use in the treatment or prevention of a disease which requires the expression of said polynucleotide of interest.

In another embodiment, the invention provides a method for the treatment or prevention of a disease that requires the expression of the polynucleotide of interest in a subject which comprises the administration to said subject of an adeno-associated viral vector comprising a recombinant viral genome wherein said recombinant viral genome comprises an expression cassette comprising transcriptional regulatory region operatively linked to a polynucleotide of interest wherein the serotype of the AAV is selected from the group consisting of AAV6, AAV7, AAV8, and AAV9.

In another embodiment, the invention provides a method for the treatment or prevention of a disease that requires the expression of a polynucleotide of interest in a subject which comprises the administration to said subject of an adeno-associated viral vector comprising a recombinant viral genome wherein said recombinant viral genome comprises an expression cassette comprising an adipose tissue-specific transcriptional regulatory region operatively linked to a polynucleotide of interest.

The AAV for use in the therapeutic method of the invention comprise an expression cassette which comprises a polynucleotide of interest and a transcriptional regulatory region. The transcriptional regulatory region may comprise a promoter and, optionally, an enhancer region.

In one embodiment, the transcriptional regulatory region allows constitutive expression of the polynucleotide of interest. Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1a promoter. See Boshart M, et al., Cell 1985; 41:521-530.

In another embodiment, the transcriptional regulatory region comprises the β-actin promoter. The β-actin promoter may be derived from any mammal, including human and rodent, or bird, including chicken. Preferably, a chicken β-actin is used.

In yet another embodiment, the transcriptional regulatory region further comprises an enhancer region. Preferably, the enhancer region is the CMV enhancer region.

In a particular embodiment, the regulatory region is a CAG regulatory region. In a preferred embodiment, the CAG regulatory region has the sequence SEQ ID NO: 1.

In another embodiment, the transcriptional regulatory region is an adipose-tissue specific transcriptional regulatory region.

If the promoter is specific for adipose tissue, then the enhancer need not be specific for adipose tissue as well. Alternatively, the transcriptional regulatory region may comprise an adipose tissue-specific promoter and an adipose tissue-specific enhancer.

In one embodiment, the tissue-specific promoter is an adipocyte-specific promoter such as, for example, the adipocyte protein 2 (aP2, also known as fatty acid binding protein 4 (FABP4)) promoter, the PPARγ promoter, the adiponectin promoter, the phosphoenolpyruvate carboxykinase (PEPCK) promoter, the promoter derived from human aromatase cytochrome p450 (p450arom), and the Foxa-2 promoter. See Graves (1991), Ross (1990), Simpson (U.S. Pat. No. 5,446,143), Mahendroo (1993), Simpson (1993), and Sasaki (1994), supra.

In one embodiment, the enhancer region is selected from the group consisting of the adipose-specific aP2 enhancer and the adipose-specific UCP1 enhancer.

In a preferred embodiment, the adipose-tissue specific regulatory region of the AAV according to the invention comprises the adipose-specific aP2 enhancer and the basal murine aP2 promoter. In a particular embodiment, the mini/aP2 regulatory region has the sequence SEQ ID NO: 2.

In another preferred embodiment, the adipose-tissue specific regulatory region of the AAV according to the invention comprises the adipose-specific UCP1 enhancer and the basal rat UCP1 promoter. In a particular embodiment, the mini/UCP1 regulatory region has the sequence SEQ ID NO: 3.

In another embodiment, the expression cassette further comprises a post-transcriptional regulatory region. In a preferred embodiment, the post-transcriptional regulatory region is WPRE or functional variants and fragments thereof and the PPT-CTS or functional variants and fragments thereof.

Other suitable polynucleotides of interest can be vectorized with the AAV of the invention and used for the treatment or prevention of diseases. See Table 1.

TABLE 1

Polynucleotides of interest

| Disease | Gene | Administration | Reference |
|---|---|---|---|
| Arthritis | IL-1 receptor antagonist, TNFR: Fc fusion protein (etanercept), TGFβ1, | Systemically | Evans C, et al., Arthritis Res. Ther. 2008, 10(110): 515-526 |
| Type 1 diabetes | IL-2 | Locally | Goudy K, et al., J. Immunol. 2011; 186(6): 3779-3786 |
| Type 2 diabetes | Leptin, CNTF, LIF | Locally or systemically | Zolotukhin S, et al., WO 2001/094605 |
| Type 2 diabetes | Angiotensin converting enzyme 2 (ACE) | Systemically | Acton L, et al., WO 2000/018899 |
| Type 2 diabetes | Glucokinase regulatory protein (GKRP) | Systemically | Caplan S, et al., US 20020065239 |
| High blood pressure | Atrial natriuretic peptide (ANP) | Systemically | Therrien J, et al., Proc. Natl. Acad. Sci. USA 2010; 107(3): 1178-1183 |
| High blood pressure | Angiotensin type 1 receptor antisense Angiotensin converting enzyme antisense β1-adrenergic receptor antisense | Systemically | Lu D, et al., Hypertension 1997; 30: 363-370 Phillips M, et al., Braz. J. Med. Biol. Res. 2000; 33(6): 715-721 |
| Obesity | Anti-angiogenic compounds (endostatin, angiostatin, VEGFR blockade, PLGF blockade), | Locally | Cao D, Nature Rev. 2010; 9: 107-115 |
| Type 2 diabetes | Insulin | Locally | Mudaliar S, et al., Endocrinol. Metab. Clin. North Am. 2001; 30(4): 935-982 |
| Obesity | BDNF | Systemically | During M, et al., WO 2009/120978 |
| Obesity | BMP7 | Locally or systemically | Tseng Y, et al., Nature 2008; 54(7207): 1000-1004 |
| Obesity | FGF21 | Locally or systemically | Xu J, et al., Diabetes 2009; 58(1): 250-259 |
| Obesity | Cardiac natriuretic peptides (NPs) | Locally or systemically | Bordicchia M, et al., J. Clin. Invest. 2012; 122(3): 1022-1036 |
| Obesity/Type 2 diabetes | Hexokinase or glucokinase | Locally | Otaegui P, et al., FASEB J. 2003; 17(14): 2097-2099 |
| Obesity/Type 2 diabetes | Hexokinase or glucokinase | Locally | Muñoz S, et al., Diabetologia 2010; 53(11): 2417-2430 |
| Obesity/Type 2 diabetes | GLP-1 | Locally | Di Pasquale G, et al., PLoS One 2012; 7(7): e40074 |
| Obesity/Type 2 diabetes | PRDM16 | Locally | Seale P, et al., J. Clin. Invest. 2011; 121(1): 96-105 |

The term "disease that requires the expression of a polynucleotide of interest", as used herein, refers to any disease in which the expression of the polynucleotide of interest is desirable. The polynucleotide of interest, as described herein, can be a gene which encodes a polypeptide of interest or, alternatively, a nucleic acid sequence that, when transcribed, generates a molecule capable of modulating the expression of an endogenous polynucleotide in a cell. Thus, the disease that requires the expression of the polynucleotide of interest can be a disease wherein it is desirable to increase or decrease the expression levels of a gene.

Moreover, the polynucleotide of interest may encode a protein which is secreted and acts systemically, or a protein which acts upon or in the vicinity of said adipocyte. In a particular embodiment, the disease that requires the expression of a polynucleotide of interest is a disease that requires the expression of a polynucleotide of interest in adipose tissue, more preferably, in white adipose tissue or brown adipose tissue.

Examples of diseases that require the expression of a polynucleotide of interest include, but are not limited to, obesity, hyperglycemia, insulin resistance, type 2 diabetes, high blood pressure, cancer, heart diseases, immune diseases, arthritis, diseases of the central nervous system, and aging related diseases.

The AAV of the invention have been proven useful for the gene therapy of adipose tissue-associated diseases, such as the delivery of hexokinase mediated by the AAV of the invention in both WAT and BAT to increase basal glucose uptake. See FIGS. 2D and 4B. Thus, in a particular embodiment, the disease that requires the regulation of the expression of a polynucleotide of interest is a disease selected from the group consisting of obesity, hyperglycemia, insulin resistance, type 2 diabetes, and high blood pressure.

Exemplary genes and associated disease states include, but are not limited to, insulin for the treatment of diabetes, CFTR for the treatment of cystic fibrosis, factor IX for the treatment of hemophilia B, factor VIII for the treatment of hemophilia A, glucose-6-phosphatase, associated with glycogen storage deficiency type 1A; phosphoenolpyruvate-carboxykinase, associated with Pepck deficiency; galactose-1 phosphate uridyl transferase, associated with galactosemia; phenylalanine hydroxylase, associated with phenylketonuria; branched chain α-ketoacid dehydrogenase, associated with maple syrup urine disease; fumarylacetoacetate hydrolase, associated with tyrosinemia type 1; methylmalonyl-CoA mutase, associated with methylmalonic acidemia; medium chain acyl CoA dehydrogenase, associated with medium chain acetyl CoA deficiency; ornithine transcarbamylase, associated with ornithine transcarbamylase deficiency; argininosuccinic acid synthetase, associated with citrullinemia; low density lipoprotein receptor protein, associated with familial hypercholesterolemia; UDP-glucouronosyltransferase, associated with Crigler-Najjar disease; adenosine deaminase, associated with severe combined immunodeficiency disease; hypoxanthine guanine phosphoribosyl transferase, associated with Gout and Lesch-Nyan syndrome; biotimidase, associated with biotimidase deficiency; β-glucocerebrosidase, associated with Gaucher disease; β-glucuronidase, associated with Sly syndrome; peroxisome membrane protein 70 kDa, associated with Zellweger syndrome; porphobilinogen deaminase, associated with acute intermittent porphyria; alpha-1 antitrypsin for treatment of alpha-1 antitrypsin deficiency (emphysema); erythropoietin for treatment of anemia due to thalassemia or to renal failure; vascular endothelial growth factor, angiopoietin-1, and fibroblast growth factor for the treatment of ischemic diseases; thrombomodulin and tissue factor pathway inhibitor for the treatment of occluded blood vessels as seen in, for example, atherosclerosis, thrombosis, or embolisms; aromatic amino acid decarboxylase (AADC), and tyrosine hydroxylase (TH) for the treatment of Parkinson's disease; the β-adrenergic receptor, anti-sense to, or a mutant form of, phospholamban, the sarco(endo)plasmic reticulum adenosine triphosphatase-2 (SERCA2), and the cardiac adenylyl cyclase for the treatment of congestive heart failure; a tumor suppressor gene such as p53 for the treatment of various cancers; a cytokine such as one of the various interleukins for the treatment of inflammatory and immune disorders and cancers; dystrophin or minidystrophin and utrophin or miniutrophin for the treatment of muscular dystrophies; adenosine deaminase (ADA) for the treatment of adenosine deaminase (ADA) deficiency; huntingin (HTT) for treating Huntington's disease; low-density lipoprotein receptor (LDLR) or apolipoprotein B (APOB) for treating familial hypercholesterolemia; phenylalanine hydroxylase (PAH) for treating phenylketonuria; polycystic kidney disease 1 (PKD1) and polycystic kidney disease 2 (PKD2) for treating polycystic kidney disease; TNFR:Fc for the treatment of arthritis; AAT for the treatment of hereditary emphysema; Sarcoglycan for the treatment of muscular dystrophy; GAD65 or GAD67 for the treatment of Parkinson's disease, AAC for the treatment of Canavan's disease, CLN2 for the treatment of Batten's disease, NGF for the treatment of Alzheimer's disease; a VEGF antagonist for the treatment of macular degeneration; IGF/HGF for the treatment of congestive heart failure, NGF for the treatment diseases of the central nervous system disorder; and a neutralizing antibody against HIV for treating HIV, HIV infection, or AIDS.

Examples of polynucleotides of interest which can be delivered by the AAV of the invention includes, but are not limited to, hexokinase, glucokinase, UCP2, UCP3, PPAR-α, leptin, leptin receptor OB-Rb, and GLP-1. In a particular embodiment, the gene of interest is selected from the group consisting of hexokinase (HK), glucokinase (GK), alkaline phosphatase (AP), and the vascular endothelial growth factor (VEGF). In one further embodiment, the AAV of the invention comprising polynucleotides expressing hexokinase or glucokinase are administered to a subject in need thereof for the treatment or prevention of type 2 diabetes. In another further embodiment, the AAV of the invention comprising polynucleotides expressing the vascular endothelial growth factor are administered to a subject in need thereof for the treatment or prevention of obesity.

Illustrative but non-limiting examples of diseases that can be treated with the method of the invention include obesity, hyperglycemia, insulin resistance, type 2 diabetes, high blood pressure, and arterial hypertension. Preferably, type 2 diabetes can be treated by expressing leptin either in the vicinity of adipocytes, or systemically, so that it reaches hypothalamus.

Additionally, the AAV of the invention have been proven useful for the genetic engineering of BAT, as the intra iBAT administration of $VEGF_{164}$ by AAV9-mini/UCP1 leads to an increment in the expression levels of total VEGF and to an increased number of vessels in iBAT. See FIGS. 4C-4F. Therefore, in a particular embodiment, the invention relates to an AAV or a pharmaceutical composition of the invention for use in the treatment or prevention of a disease that requires the expression of VEGF such as, for example, a disease whose management can benefit from inducing angiogenesis, arteriogenesis, or vasculogenesis. Examples of diseases that require the expression of VEGF include, but are not limited to, acute surgical and traumatic wounds, burns, scalds, venous ulcers, arterial ulcers, pressure sores (aka decubitus ulcers), diabetic ulcers, post-radiation wounds, skin grafts, ulcers of mixed aetiology, and other chronic or necrotic wounds.

Additionally, the intra eWAT administration of the hSeAP gene (i.e. human placental-derived secreted alkaline phosphase) with the AAV9-mini/aP2 viral vector leads to a sustained increment in the circulating levels of hSeAP. Therefore, in a particular embodiment, the invention relates to an AAV or a pharmaceutical composition of the invention for use in the treatment or prevention of a disease that requires the expression of AP such as, for example, a LPS (i.e. lipopolysaccharide) mediated or exacerbated disease. Examples of diseases to that require the expression of AP include, but are not limited to, inflammatory bowel disease, sepsis or septic shock, systemic inflammatory response syndrome (SIRS), meningococcemia, traumatic hemorrhagic shock, hum injuries, cardiovascular surgery or cardiopulmonary bypass, liver surgery or transplant, liver disease, pancreatitis, necrotizing enterocolitis, periodontal disease, pneumonia, cystic fibrosis, asthma, coronary heart disease, congestive heart failure, renal disease, hemolytic uremic syndrome, kidney dialysis, cancer, Alzheimer's diseases, and autoimmune diseases such as rheumatoid arthritis, and systemic lupus erythematosus.

4. Methods for Transducing Cells In Vitro

In a third aspect, the invention relates to a method for transducing cells in vitro by using the AAV vectors of the invention. Thus, the present invention relates also to a method for transducing cells in vitro which comprises contacting said cells with an AAV comprising a recombinant viral genome wherein said recombinant viral genome comprises an expression cassette comprising an adipose tissue-specific transcriptional regulatory region operatively linked to a polynucleotide of interest.

In a preferred embodiment, the adeno-associated viral vector used in the method for transducing cells in vitro has a serotype selected from the group consisting of AAV6, AAV7, AAV8, and AAV9. In another embodiment, the adeno-associated virus ITRs are AAV2 ITRs.

In another embodiment, the adeno-associated viral vector comprises an adipose tissue-specific transcriptional regulatory region. In yet another embodiment, the adipose tissue-specific transcriptional regulatory region comprises a promoter region selected from the group consisting of the basal murine aP2 promoter and the basal rat UCP1 promoter. In yet another embodiment, the adipose tissue-specific transcriptional regulatory region further comprises an enhancer region operatively linked to the promoter region. In yet another embodiment, the enhancer region is selected from the group consisting of the adipose-specific aP2 enhancer and the adipose-specific UCP1 enhancer. In a still more preferred embodiment, the adipose tissue-specific transcriptional regulatory region is selected from the group consisting of:
  i) a polynucleotide comprising the adipose-specific aP2 enhancer and the basal murine aP2 promoter and
  ii) a polynucleotide comprising the adipose-specific UCP1 enhancer and the basal rat UCP1 promoter.

In another embodiment, the expression cassette further comprises a post-transcriptional regulatory region. In yet another embodiment, the post-transcriptional regulatory region is WPRE.

In another embodiment, the polynucleotide of interest encodes a protein which is selected from the group consisting of a secreted protein which acts systemically and a protein which acts upon or in the vicinity of said adipocyte. In a still more preferred embodiment, the polynucleotide of interest encodes a protein selected from the group consisting on hexokinase, glucokinase, alkaline phosphatase, and vascular endothelial growth factor.

In another embodiment, the invention relates to a method for transducing cells in vitro with AAV which comprises a recombinant viral genome wherein said recombinant viral genome comprises an expression cassette comprising transcriptional regulatory region operatively linked to a polynucleotide of interest wherein the serotype of the AAV is selected from the group consisting of AAV6, AAV7, AAV8, and AAV9.

In one embodiment, the adeno-associated virus ITRs are AAV2 ITRs.

In another embodiment, the adeno-associated viral vector comprises a recombinant genome which contains a transcriptional regulatory region. In one embodiment, the transcriptional regulatory region is a constitutive promoter. In a preferred embodiment, the constitutive transcriptional regulatory region comprises the actin promoter. In yet another embodiment, the constitutive transcriptional regulatory region further comprises an enhancer region operatively linked to the promoter region. In a still more preferred embodiment, the enhancer region is the cytomegalovirus enhancer.

In one embodiment, the transcriptional regulatory region is an adipose tissue-specific transcriptional regulatory region. In yet another embodiment, the adipose tissue-specific transcriptional regulatory region comprises a promoter region selected from the group consisting of the basal murine aP2 promoter and the basal rat UCP1 promoter. In yet another embodiment, the adipose tissue-specific transcriptional regulatory region further comprises an enhancer region operatively linked to the promoter region. In yet another embodiment, the enhancer region is selected from the group consisting of the adipose-specific aP2 enhancer and the adipose-specific UCP1 enhancer. In a still more preferred embodiment, the adipose tissue-specific transcriptional regulatory region is selected from the group consisting of:
  i) a polynucleotide comprising the adipose-specific aP2 enhancer and the basal murine aP2 promoter and
  ii) a polynucleotide comprising the adipose-specific UCP1 enhancer and the basal rat UCP1 promoter.

In another embodiment, the expression cassette further comprises a post-transcriptional regulatory region. In yet another embodiment, the post-transcriptional regulatory region is WPRE.

In another embodiment, the polynucleotide of interest encodes a protein which is selected from the group consisting of a secreted protein which acts systemically and a protein which acts upon or in the vicinity of said adipocyte. In a still more preferred embodiment, the polynucleotide of interest encodes a protein selected from the group consisting on hexokinase, glucokinase, alkaline phosphatase, and vascular endothelial growth factor.

Any cells can be transduced using the in vitro method of the invention. In a particular embodiment, the AAV are used to transduce an adipose tissue cell. In a still more preferred embodiment, the adipose tissue cell is a brown adipocyte or a white adipocyte.

When the in vitro methods for transducing cells according to the invention are carried out to transduce a white adipocyte, then the transcriptional regulatory region within the AAV comprises preferably a mini/aP2 regulatory region. In another embodiment, when the in vitro methods for transducing a cell according to the invention are carried out to transduce a brown adipocyte, then the transcriptional regulatory region within the AAV comprises preferably an expression cassette comprising a mini/UCP1 regulatory region.

In another aspect of the invention, to improve the transgene expression attained by the mini/aP2 and mini/UCP1 promoters, CAG promoter are used in conjunction with tissue-specific miRNA target sequences in an attempt to obtain high expression levels in adipose tissue and de-target transgene expression from off-target organs. This results in a further strengthen of the potential of AAV vectors to genetically modify adipose tissue when administered locally or systemically.

In an additional embodiment, the invention relates to a method for isolating the cells transduced in vivo by using the AAV vectors of the invention and culturing them in vitro. In another embodiment, the invention relates to the said isolated transduced cells and the cell and pharmaceutical compositions comprising them.

5. Transduced Adipocytes and Adipocyte Cell Compositions, Ex-Vivo Therapeutic Method In a fourth aspect, the invention relates to the adipocytes obtained by the in vitro method of the invention. In another embodiment, the invention relates to a cell composition which comprises adipocytes obtained according to the method of the invention. Moreover, the invention also relates to adipocytes or adipocyte cell compositions comprising the genome of an AAV according to the invention. Preferably, at least 50% of the cell composition is comprised by adipocytes according to the invention. More preferably, at least 60%, 70%, 80%, 90%, 95%, and 100% of the cell composition is comprised by adipocytes according to the invention.

As mentioned above, the AAV of the invention can be used to transduce cells in vitro in order to introduce a polynucleotide of interest to said cells. Subsequently, the transduced cells can be implanted in the human or animal body to obtain the desired therapeutic effect.

Thus, in another embodiment, the invention relates to adipocytes or to a cell composition comprising adipocytes obtained according to the method of the invention for use in medicine.

In another embodiment, the invention relates to adipocytes or to a cell composition comprising adipocytes obtained according to the method of the invention for use in the treatment of a disease which requires the expression of the polynucleotide of interest.

In another embodiment, the invention relates to a method for the treatment or prevention of a disease which comprises administering to subject in need thereof the adipocytes or cell compositions obtained according to the method of the invention. Examples of diseases that can be addressed with this approach have been defined above in the context of the AAV of the invention.

6. Polynucleotides, Vectors, and Plasmids

In a fifth aspect, the invention relates to polynucleotides which are useful for producing the AAV according to the invention. Thus, in another embodiment, the invention relates to a polynucleotide ("polynucleotide of the invention") comprising an expression cassette flanked by adeno-associated virus ITRs wherein said expression cassette comprises an adipose tissue-specific regulatory region operatively linked to a polynucleotide of interest.

In a preferred embodiment, the adipose tissue-specific regulatory region comprises a promoter region selected from the group consisting of the basal murine aP2 promoter and the basal rat UCP1 promoter.

In another embodiment, the adipose tissue-specific regulatory region further comprises an enhancer region operatively linked to the promoter region. In a still more preferred embodiment, the enhancer region is selected from the group consisting of the adipose-specific aP2 enhancer and the adipose-specific UCP1 enhancer.

In another embodiment, the regulatory region is selected from the group consisting of:
i) a polynucleotide comprising the adipose-specific aP2 enhancer and the basal murine aP2 promoter and
ii) a polynucleotide comprising the adipose-specific UCP1 enhancer and the basal rat UCP1 promoter.

In another embodiment, the expression cassette of the polynucleotide of the invention further comprises a post-transcriptional regulatory element. In yet another embodiment, the post-transcriptional regulatory region is WPRE.

In another embodiment, the polynucleotide of interest comprised in the polynucleotide of the invention encodes a protein selected from the group consisting on hexokinase, glucokinase, alkaline phosphatase, and vascular endothelial growth factor.

The polynucleotide of the invention could be incorporated into a vector such as, for example, a plasmid. Thus, in an additional embodiment, the invention relates to a vector or plasmid comprising the polynucleotide of the invention. According to the present invention, the terms "vector" and "plasmid" are interchangeable.

In a particular embodiment, the polynucleotide of the invention is incorporated into an adeno-associated viral vector or plasmid. Preferably, all other structural and non-structural coding sequences necessary for the production of adeno-associated virus are not present in the viral vector since they can be provided in trans by another vector, such as a plasmid, or by stably integrating the sequences into a packaging cell line.

The polynucleotides of the invention can be obtained using molecular biology techniques well known in the art. See Brown (1995), Watson (1992), Alberts (2008), Innis (1990), Erlich (1989), Sambrook (1989), Bishop (1987), Reznikoff (1987), Davis (1986), and Schleef (2001), supra. In another embodiment, the invention relates to an AAV vector wherein the genome comprises a polynucleotide of the invention.

7. Methods for Obtaining AAV

In a sixth aspect, the invention relates to a method for obtaining the AAV of the invention. Said AAV can be obtained by introducing the polynucleotides of the invention into cells that express the rep and cap constitutively. Thus, in another embodiment, the invention relates to a method for obtaining an adeno-associated viral vector comprising the steps of:
i) providing a cell comprising a polynucleotide of the invention flanked by the AAV ITRs, AAV cap proteins, AAV rep proteins and viral or cellular proteins upon which AAV is dependent for replication,
ii) maintaining the cell under conditions adequate for assembly of the AAV, and
iii) purifying the adeno-associated viral vectors produced by the cell.

In a preferred embodiment, the adipose tissue-specific regulatory region forming part of the polynucleotide of the invention comprises a promoter region selected from the group consisting of the basal murine aP2 promoter and the basal rat UCP1 promoter.

In another embodiment, the adipose tissue-specific regulatory region further comprises an enhancer region operatively linked with the promoter region. In a still more preferred embodiment, the enhancer region is selected from the group consisting of the adipose-specific aP2 enhancer and the adipose-specific UCP1 enhancer.

In another embodiment, the regulatory region is selected from the group consisting of:
i) a polynucleotide comprising the adipose-specific aP2 enhancer and the basal murine aP2 promoter and
ii) a polynucleotide comprising the adipose-specific UCP1 enhancer and the basal rat UCP1 promoter.

In another embodiment, the expression cassette of the polynucleotide of the invention further comprises a post-transcriptional regulatory element. In yet another embodiment, the post-transcriptional regulatory region is WPRE.

In another embodiment, the polynucleotide of interest comprised in the polynucleotide of the invention encodes a protein selected from the group consisting on hexokinase, glucokinase, alkaline phosphatase, and vascular endothelial growth factor.

The production of recombinant AAV (rAAV) for vectorizing transgenes have been described previously. See Ayuso E, et al., Curr. Gene Ther. 2010; 10:423-436, Okada T, et al., Hum. Gene Ther. 2009; 20:1013-1021, Zhang H, et al., Hum. Gene Ther. 2009; 20:922-929, and Virag T, et al., Hum. Gene Ther. 2009; 20:807-817. These protocols can be used or adapted to generate the AAV of the invention. In one embodiment, the producer cell line is transfected transiently with the polynucleotide of the invention (comprising the expression cassette flanked by ITRs) and with construct(s) that encodes rep and cap proteins and provides helper functions. In another embodiment, the cell line supplies stably the helper functions and is transfected transiently with the polynucleotide of the invention (comprising the expression cassette flanked by ITRs) and with construct(s) that encodes rep and cap proteins. In another embodiment, the cell line supplies stably the rep and cap proteins and the helper functions and is transiently transfected with the polynucleotide of the invention. In another embodiment, the cell line supplies stably the rep and cap proteins and is transfected transiently with the polynucleotide of the invention and a polynucleotide encoding the helper functions. In yet another embodiment, the cell line supplies stably the polynucleotide of the invention, the rep and cap proteins and the helper functions. Methods of making and using these and other AAV production systems have been described in the art. See Muzyczka N, et al., U.S. Pat. No. 5,139,941, Zhou X, et al., U.S. Pat. No. 5,741,683, Samulski R, et al., U.S. Pat. No. 6,057,152, Samulski R, et al., U.S. Pat. No. 6,204,059, Samulski R, et al., U.S. Pat. No. 6,268,213, Rabinowitz J, et al., U.S. Pat. No. 6,491,907, Zolotukhin S, et al., U.S. Pat. No. 6,660,514, Shenk T, et al., U.S. Pat. No. 6,951,753, Snyder R, et al., U.S. Pat. No. 7,094,604, Rabinowitz J, et al., U.S. Pat. No. 7,172,893, Monahan P, et al., U.S. Pat. No. 7,201,898, Samulski R, et al., U.S. Pat. No. 7,229,823, and Ferrari F, et al., U.S. Pat. No. 7,439,065.

In another embodiment, the transgene delivery capacity of AAV can be increased by providing AAV ITRs of two genomes that can anneal to form head to tail concatamers. Generally, upon entry of the AAV into the host cell, the single-stranded DNA containing the transgene is converted by the host cell DNA polymerase complexes into double-stranded DNA, after which the ITRs aid in concatamer formation in the nucleus. As an alternative, the AAV may be engineered to be a self-complementary (sc) AAV, which enables the viral vector to bypass the step of second-strand synthesis upon entry into a target cell, providing an scAAV viral vector with faster and, potentially, higher (e.g. up to 100-fold) transgene expression. For example, the AAV may be engineered to have a genome comprising two connected single-stranded DNAs that encode, respectively, a transgene unit and its complement, which can snap together following delivery into a target cell, yielding a double-stranded DNA encoding the transgene unit of interest. Self-complementary AAV have been described in the art. See Carter B, U.S. Pat. No. 6,596,535, Carter B, U.S. Pat. No. 7,125,717, and Takano H, et al., U.S. Pat. No. 7,456,683.

Cap proteins have been reported to have effects on host tropism, cell, tissue, or organ specificity, receptor usage, infection efficiency, and immunogenicity of AAV viruses. Accordingly, an AAV Cap for use in an rAAV may be selected taking into consideration, for example, the subject's species (e.g. human or non-human), the subject's immunological state, the subject's suitability for long or short-term treatment, or a particular therapeutic application (e.g. treatment of a particular disease or disorder, or delivery to particular cells, tissues, or organs). In another embodiment, the rAAV Cap is based on Caps from two or three or more AAV serotypes. In a particular embodiment, AAV cap genes derive from the serotypes AAV1, AAV2, AAV4, AAV5, AAV6, AAV7, AAV8, or AAV9. In a preferred embodiment, the AAV cap genes are derived from the serotypes AAV6, AAV7, AAV8, and AAV9.

In some embodiments, an AAV Cap for use in the method of the invention can be generated by mutagenesis (i.e. by insertions, deletions, or substitutions) of one of the aforementioned AAV Caps or its encoding nucleic acid. In some embodiments, the AAV Cap is at least 70%, 75%, 80%, 85%, 90%, 95%, 98%, or 99% or more similar to one or more of the aforementioned AAV Caps.

In some embodiments, the AAV Cap is chimeric, comprising domains from at least two of the aforementioned AAV Caps. In some embodiments, the AAV Cap is a mosaic of VP1, VP2, and VP3 monomers from two or three different AAV or recombinant AAV. In some embodiments, a rAAV composition comprises more than one of the aforementioned Caps.

In some embodiments, an AAV Cap for use in a rAAV composition is engineered to contain an heterologous sequence or other modification. For example, a peptide or protein sequence that confers selective targeting or immune evasion may be engineered into a Cap protein. Alternatively or in addition, the Cap may be chemically modified so that the surface of the rAAV is polyethylene glycolated (i.e pegylated), which may facilitate immune evasion. The Cap protein may also be mutagenized (e.g. to remove its natural receptor binding, or to mask an immunogenic epitope).

In a particular embodiment, AAV rep genes derived from the serotypes AAV1, AAV2, AAV4, AAV5, AAV6, AAV7, AAV8, or AAV9. In a preferred embodiment, the AAV rep and cap genes are derived from the serotypes AAV6, AAV7, AAV8, and AAV9.

The genes AAV rep, AAV cap and genes providing helper functions can be introduced into the cell by incorporating said genes into a vector such as, for example, a plasmid, and introducing said vector into the cell. The genes can be incorporated into the same plasmid or into different plasmids. In a preferred embodiment, the AAV rep and cap genes are incorporated into one plasmid and the genes providing helper functions are incorporated into another plasmid. Examples of plasmids comprising the AAV rep and cap genes suitable for use with the methods of the invention include the pHLP19 and pRep6cap6 vectors. See Colisi P, U.S. Pat. No. 6,001,650 and Russell D, et al., U.S. Pat. No. 6,156,303. In a preferred embodiment, the genes providing helper functions derive from adenovirus.

The polynucleotide of the invention and the polynucleotides comprising AAV rep and cap genes or genes providing helper functions can be introduced into the cell by using any suitable method well known in the art. See Ausubel F, et al., Eds., "Short Protocols in Molecular Biology", 4th Ed. (John Wiley and Sons, Inc., New York, N.Y., US, 1997), Brown (1995), Watson (1992), Alberts (2008), Innis (1990), Erlich (1989), Sambrook (1989), Bishop (1987), Reznikoff (1987), Davis (1986), and Schleef (2001), supra. Examples of transfection methods include, but are not limited to, co-precipitation with calcium phosphate, DEAE-dextran, polybrene, electroporation, microinjection, liposome-mediated fusion, lipofection, retrovirus infection and biolistic transfection. In a particular embodiment, the transfection is carried out by means of co-precipitation with calcium phosphate. When the cell lacks the expression of any of the AAV rep and cap genes and genes providing adenoviral helper functions, said genes can be introduced into the cell simultaneously with the polynucleotide of the first aspect of the invention. Alternatively, said genes can be introduced in the cell before or after the introduction of the polynucleotide of the first aspect of the invention. In a particular embodiment, the cells are transfected simultaneously with three plasmids:

1) a plasmid comprising the polynucleotide of the invention
2) a plasmid comprising the AAV rep and cap genes
3) a plasmid comprising the genes providing the helper functions Methods of culturing packaging cells and exemplary conditions which promote the release of AAV vector particles, such as the producing of a cell lysate, may be carried out as described in examples herein. Producer cells are grown for a suitable period of time in order to promote release of viral vectors into the media. Generally, cells may be grown for about 24 hours, about 36 hours, about 48 hours, about 72 hours, about 4 days, about 5 days, about 6 days, about 7 days, about 8 days, about 9 days, up to about 10 days. After about 10 days (or sooner, depending on the culture conditions and the particular producer cell used), the level of production generally decreases significantly. Generally, time of culture is measured from the point of viral production. For example, in the case of AAV, viral production generally begins upon supplying helper virus function in an appropriate producer cell as described herein. Generally, cells are harvested about 48 to about 100, preferably about 48 to about 96, preferably about 72 to about 96, preferably about 68 to about 72 hours after helper virus infection (or after viral production begins).

The AAV of the invention can be obtained from both: i) the cells transfected with the polynucleotides of the invention and ii) the culture medium of said cells after a period of time post-transfection, preferably 72 hours. Any method for the purification of the AAV from said cells or said culture medium can be used for obtaining the AAV of the invention. In a particular embodiment, the AAV of the invention are purified following an optimized method based on a polyethylene glycol precipitation step and two consecutive cesium chloride (CsCl) gradients. See Ayuso, 2010, supra. Purified AAV of the invention can be dialyzed against PBS, filtered and stored at −80° C. Titers of viral genomes can be determined by quantitative PCR following the protocol described for the AAV2 reference standard material using linearized plasmid DNA as standard curve. See Lock M, et al., Hum. Gene Ther. 2010; 21:1273-1285.

In some embodiments, the methods further comprise purification steps, such as treatment of the cell lysate with benzonase, purification of the cell lysate over a CsCl gradient, or purification of the cell lysate with the use of heparin sulphate chromatography. See Halbert C, et al., Methods Mol. Biol. 2004; 246:201-212.

Various naturally occurring and recombinant AAV, their encoding nucleic acids, AAV Cap and Rep proteins and their sequences, as well as methods for isolating or generating, propagating, and purifying such AAV, and in particular, their capsids, suitable for use in producing AAV are known in the art. See Gao, 2004, supra, Russell D, et al., U.S. Pat. No. 6,156,303, Hildinger M, et al., U.S. Pat. No. 7,056,502, Gao G, et al., U.S. Pat. No. 7,198,951, Zolotukhin S, U.S. Pat. No. 7,220,577, Gao G, et al., U.S. Pat. No. 7,235,393, Gao G, et al., U.S. Pat. No. 7,282,199, Wilson J, et al., U.S. Pat. No. 7,319,002, Gao G, et al., U.S. Pat. No. 7,790,449, Gao G, et al., US 20030138772, Gao G, et al., US 20080075740, Hildinger M, et al., WO 2001/083692, Wilson J, et al., WO 2003/014367, Gao G, et al., WO 2003/042397, Gao G, et al., WO 2003/052052, Wilson J, et al., WO 2005/033321, Vandenberghe L, et al., WO 2006/110689, Vandenberghe L, et al., WO 2007/127264, and Vandenberghe L, et al., WO 2008/027084.

8. Pharmaceutical Compositions

The AAV of the invention can be administered to the human or animal body by conventional methods, which require the formulation of said vectors in a pharmaceutical composition. Thus, in a seventh aspect, the invention relates to a pharmaceutical composition (hereinafter referred to as "pharmaceutical composition of the invention") comprising an AAV, wherein said AAV comprises a recombinant viral genome wherein said recombinant viral genome comprises an expression cassette comprising an adipose tissue-specific transcriptional regulatory region operatively linked to a polynucleotide of interest. Alternatively, the pharmaceutical composition of the invention may comprise the polynucleotides or polypeptides of the invention.

Said pharmaceutical composition may include a therapeutically effective quantity of the AAV of the invention and a pharmaceutically acceptable carrier.

Compositions of the invention may be formulated for delivery to animals for veterinary purposes (e.g. livestock (cattle, pigs, others)), and other non-human mammalian subjects, as well as to human subjects. The AAV can be formulated with a physiologically acceptable carrier for use in gene transfer and gene therapy applications. The dosage of the formulation can be measured or calculated as viral particles or as genome copies ("GC")/viral genomes ("vg").

Any method known in the art can be used to determine the genome copy (GC) number of the viral compositions of the invention. One method for performing AAV GC number titration is as follows: purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome.

Also, the viral compositions can be formulated in dosage units to contain an amount of viral vectors that is in the range of about $1.0 \times 10^9$ GC to about $1.0 \times 10^{15}$ GC (to treat an average subject of 70 kg in body weight), and preferably $1.0 \times 10^{12}$ GC to $1.0 \times 10^{14}$ GC for a human patient. Preferably, the dose of virus in the formulation is $1.0 \times 10^9$ GC, $5.0 \times 10^9$ GC, $1.0 \times 10^{10}$ GC, $5.0 \times 10^{10}$ GC, $1.0 \times 10^{11}$ GC, $5.0 \times 10^{11}$ GC, $1.0 \times 10^{12}$ GC, $5.0 \times 10^{12}$ GC, or $1.0 \times 10^{13}$ GC, $5.0 \times 10^{13}$ GC, $1.0 \times 10^{14}$ GC, $5.0 \times 10^{14}$ GC, or $1.0 \times 10^{15}$ GC.

The viral vectors can be formulated in a conventional manner using one or more physiologically acceptable carriers or excipients. The AAV may be formulated for parenteral administration by injection (e.g. by bolus injection or continuous infusion). Formulations for injection may be presented in unit dosage form (e.g. in ampoules or in multi-dose containers) with an added preservative. The viral compositions may take such forms as suspensions, solutions, or emulsions in oily or aqueous vehicles, and may contain formulatory agents such as suspending, stabilizing, or dispersing agents. Liquid preparations of the AAV formulations may be prepared by conventional means with pharmaceutically acceptable additives such as suspending agents (e.g. sorbitol syrup, cellulose derivatives or hydrogenated edible fats), emulsifying agents (e.g. lecithin or acacia), non-aqueous vehicles (e.g. almond oil, oily esters, ethyl alcohol or fractionated vegetable oils), and preservatives (e.g. methyl or propyl-p-hydroxybenzoates or sorbic acid). The preparations may also contain buffer salts. Alternatively, the compositions may be in powder form for constitution with a suitable vehicle (e.g. sterile pyrogen-free water) before use.

Also encompassed is the use of adjuvants in combination with or in admixture with the AAV of the invention. Adjuvants contemplated include, but are not limited, to mineral salt adjuvants or mineral salt gel adjuvants, particulate adjuvants, microparticulate adjuvants, mucosal adjuvants, and immunostimulatory adjuvants.

Adjuvants can be administered to a subject as a mixture with AAV of the invention, or used in combination AAV.

The pharmaceutical composition of the invention may be administered locally or systemically. In a preferred embodiment, the pharmaceutical composition is administered near the tissue or organ whose cells are to be transduced. In a particular embodiment, the pharmaceutical composition of the invention is administered locally in the white adipose tissue (WAT) or in the brown adipose tissue (BAT) by intra-WAT or intra-BAT injection. In another preferred embodiment, the pharmaceutical composition of the invention is administered systemically.

The pharmaceutical composition can be formulated in accordance with routine procedures as a pharmaceutical composition adapted for intravenous, subcutaneous, or intramuscular administration to human beings. Injectables can be prepared in conventional forms, either as liquid solutions or suspensions, solid forms suitable for solution or suspension in liquid prior to injection, or as emulsions. When necessary, the composition may also include a local anaesthetic such as lidocaine to relieve pain at the injection site. When the composition is going to be administered by infiltration, it can be dispensed with an infiltration bottle which contains water or saline solution of pharmaceutical quality. When the composition is administered by injection, a water vial can be provided for injection or sterile saline solution, so that the ingredients can be mixed before administration.

The term "therapeutically effective quantity" refers to the quantity of the polynucleotides, vectors, polypeptides, or pharmaceutical compositions of the invention calculated to produce the desired effect and will generally be determined, among other reasons, by the own features of the polynucleotides, vectors, polypeptides, and pharmaceutical compositions of the invention and the therapeutic effect to be obtained. The quantity of the polynucleotides, vectors, polypeptides or pharmaceutical compositions of the invention that will be effective in the treatment of a disease can be determined by standard clinical techniques described herein or otherwise known in the art. Furthermore, in vitro tests can also be optionally used to help identify optimum dosage ranges. The precise dose to use in the formulation will depend on the administration route, and the severity of the condition, and it should be decided at the doctor's judgement and depending on each patient's circumstances. The effective doses can be extrapolated from a pair of response curves to doses derived from model in vitro assay systems or in animals. For systemic administration, a therapeutically effective dose can be initially estimated from in vitro assays. For example, a dose can be formulated in animal models to achieve a circulating concentration range which includes the IC50 which has been determined in cell culture. Said information can be used to precisely determine useful doses in humans. The initial doses can also be estimated from in vivo data (e.g. animal models) using techniques well known in the state of the art. Someone with normal experience in the state of the art can easily optimize administration to humans based on the data in animals.

Such systemic administration includes, without limitation, any administration route which does not imply direct injection into the adipose tissue. More particularly, the systemic administration includes a systemic injection of the polynucleotides, vectors, polypeptides, and pharmaceutical compositions of the invention, such as intramuscular (im), intravascular (ie), intraarterial (ia), intravenous (iv), intraperitoneal (ip), subcutaneous or transdermic injections. Peripheral administration also includes oral administration of the polynucleotides, vectors, polypeptides, and pharmaceutical compositions of the invention, delivery using implants, or administration by instillation through the respiratory system (e.g. intranasal) using sprays, aerosols or any other appropriate formulations. Preferably, the systemic administration is via im, ip, ia or iv injection. Most preferably, the polynucleotides, vectors, polypeptides, and pharmaceutical compositions of the invention are administered via iv injection. See During M, WO 1996/040954 and Monahan P, et al., WO 2001/091803.

The pharmaceutical compositions of the invention may be administered in a simple dose or, in particular embodiments of the invention, multiples doses (e.g. two, three, four, or more administrations) may be employed to achieve a therapeutic effect. Preferably, the AAV comprised in the pharmaceutical composition of the invention are from different serotypes when multiple doses are required.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

General Procedures

1. Subject Characteristics

Male ICR mice 8-12 weeks old, C57Bl/6J mice 9-13 weeks old, and B6.V-Lep$^{ob}$/OlaHsd (ob/ob) and BKS.Cg-+Lepr$^{db}$/+Lepr$^{db}$/OlaHsd (db/db) mice 8 weeks old were used. Mice were fed ad libitum with a standard diet (Teklad Global Diets®, Harlan Labs., Inc., Madison, Wis., US) and kept under a light-dark cycle of 12 h (lights on at 8:00 a.m.). For tissue sampling, mice were anaesthetized by means of inhalational anaesthetics isoflurane (IsoFlo®, Abbott Laboratories, Abbott Park, Ill., US) and decapitated. Tissues of interest were excised and kept at −80° C. or with formalin, until analysis.

2. Recombinant AAV Vectors

Vectors were generated by triple transfection of HEK293 cells according to standard methods. See Ayuso, 2010, supra. Cells were cultured in 10 roller bottles (850 cm$^2$, flat; Corning™, Sigma-Aldrich Co., Saint Louis, Mo., US) in DMEM 10% FBS to 80% confluence and co-transfected by calcium phosphate method with a plasmid carrying the expression cassette flanked by the AAV2 ITRs, a helper plasmid carrying the AAV2 rep gene and the AAV of serotypes 1, 2, 4, 5, 6, 7, 8 or 9 cap gene, and a plasmid carrying the adenovirus helper functions. Transgenes used were: a) eGFP driven by: a1) the hybrid cytomegalovirus enhancer/chicken β-actin constitutive promoter (CAG) and the WPRE regulatory element, a2) the mouse mini/aP2 regulatory region or a3) the rat mini/UCP1 regulatory region; b) murine hexokinase II (mHkII) cDNA driven by: b1) the CMV ubiquitous promoter and WPRE, b2) the mouse mini/aP2 regulatory region or b3) the rat mini/UCP1 regulatory region, c) human placental-derived secreted alkaline phosphatase (hSeAP) driven by the mouse mini/aP2 regulatory region and WPRE, d) murine VEGF164 driven by the rat mini/UCP1 regulatory region, and e) RFP driven by the CMV ubiquitous promoter. See Ross, 1990, Graves, 1992, and Cassard-Doulcier, 1998, supra. A non-coding plasmid carrying the CMV promoter (pAAV-MCS, Stratagene™, Agilent Technologies, Inc., Santa Clara, Calif., US), the mini/aP2 regulatory region or the mini/UCP1 regulatory region and a multicloning site were used to produce null particles. AAV were purified with an optimized method based on a polyethylene glycol precipitation step and two consecutive cesium chloride (CsCl) gradients. This second-generation CsCl-based protocol reduced empty AAV capsids and DNA and protein impurities dramatically. See Ayuso, 2010, supra. Purified AAV vectors were dialyzed against PBS, filtered and stored at −80° C. Titers of viral genomes were determined by quantitative PCR following the protocol described for the AAV2 reference standard material using linearized plasmid DNA as standard curve. See Lock M, et al., Hum. Gene Ther. 2010; 21:1273-1285. The vectors were constructed according to molecular biology techniques well known in the art. See Brown (1995), Watson (1992), Alberts (2008), Innis (1990), Erlich (1989), Sambrook (1989), Bishop (1987), Reznikoff (1987), Davis (1986), and Schleef (2001), supra.

3. In Vivo Intra-eWAT Administration of AAV Vectors

Mice were anesthetized with an intraperitoneal injection of ketamine (100 mg/kg) and xylazine (10 mg/kg). A laparotomy was performed in order to expose the epididymal white adipose tissue. AAV vectors were resuspended in saline solution with or without 2% Pluronics F88 (BASF Corp., Florham Park, N.J., US) and injected directly into the epididymal fat pad. Each epididymal fat pad was injected twice with 50 μL of the AAV solution (one injection close to the testicle and the other one in the middle of the fat pad). The abdomen was rinsed with sterile saline solution and closed with a two-layer approach.

4. In Vivo Intra-iBAT and Intra-iWAT Administration of AAV Vectors

Mice were anesthetized with an intraperitoneal injection of ketamine (100 mg/kg) and xylazine (10 mg/kg). A longitudinal 1.5-2 cm long incision at the interscapular or inguinal area was performed in order to expose iBAT or iWAT, respectively. To distribute the vector in the whole depot, each iBAT or iWAT received 4 injections of 10 μl of AAV solution using a Hamilton syringe. Skin was closed using a one-layer approach.

5. Systemic Administration of AAV Vectors

The appropriate amount of the AAV solution was diluted in 200 μL of saline solution and was manually injected into the lateral tail vein without exerting pressure at the moment of delivery. Before the injection, the animals were put under a 250 W infrared heat lamp (Philips NV, Amsterdam, NL) for a few minutes to dilate the blood vessels and facilitate viewing and easier access to the tail vein. A plastic restrainer (Harvard Apparatus, Holliston, Mass., US) was used to secure the animal for injection. No anesthesia was used since an appropriate restraining device was employed. A 30-gauge needle was utilized to inject the animals.

6. Immunohistochemistry

For detection of GFP, RFP, and α-SMA, tissues were fixed for 12 to 24 hours in 10% formalin, embedded in paraffin, and sectioned. Sections were incubated overnight at 4° C. with a goat anti-GFP antibody (Abcam plc, Cambridge, Mass., US) diluted 1:300, with a rabbit anti-RFP antibody (Abcam plc, Cambridge, Mass., US) diluted 1/400 or with a mouse anti-α-SMA antibody (Sigma-Aldrich Co., Saint Louis, Mo., US) diluted 1/300. A biotinylated donkey anti-goat antibody (Santa Cruz Biotechnology, Inc., Santa Cruz, Calif., US) diluted 1:300, or a biotinylated goat anti-rabbit antibody (Pierce Antibodies, Thermo Fisher Scientific Inc., Rockford, Ill., US) diluted 1/300 or a biotinylated horse anti-mouse antibody (Vector Laboratories, Burlingame, Calif., US) diluted 1/300 were used as secondary antibody. Streptavidine Alexa Fluor 488 (Molecular Probes®, Life Technologies Corp., Carslbad, Calif., US) diluted 1:300 was used as fluorochrome and Hoescht bisbenzimide (Sigma-Aldrich Co., Saint Louis, Mo., US) was used for nuclear counterstaining. Alternatively, ABC peroxidase kit (Pierce Biotechnology, Inc., Rockford, Ill., US) diluted 1:50 was used and sections were counterstained in Mayer's hematoxylin.

7. Analysis of β-galactosidase Expression in eWAT Samples

To detect the presence of β-galactosidase in eWAT in toto, tissue samples were fixed for 1 h in 4% paraformaldehyde, washed twice in PBS solution, and then incubated in X-Gal (5-bromo-4-chloro-3-β-D-galactopyranoside) in 5 mM $K_3Fe(CN)_5$, 5 mM $K_4Fe(CN)_6$, and 1 mM $MgCl_2$ in PBS for 6-8 h in the dark at 37° C.

8. GFP Content

For determining GFP content, tissues were mechanically disrupted in 1 mL of lysis buffer (50 mM/L Tris, 1% Nonidet P40, 0.25% sodium deoxycholate, 150 mM/L NaCl, 1 mM/L EDTA, in PBS, pH 7.4, sterile filtered) with a Polytron® type tissue homogenizer and incubated for 10 minutes at RT. After incubation, samples were centrifuged at 14,000 rpm for 10 minutes. Supernatant was transferred to a new tube and the GFP content in 100 μL of this solution was measured with a luminescence spectrometer Flx800 (Bio-Tek Instruments, Inc, Winooski, Vt., US) with 488 nm excitation wavelength and 512 nm emission wavelength. Total GFP content values were corrected by protein contain of the sample.

9. Isolation of Adipocytes from Epididymal Fat Pad

AAV-transduced adipocytes were isolated using a modification of the Rodbell's method. See Rodbell M, J. Biol. Chem. 1964; 239:375-380. Isofluorane-anesthetized mice were killed by decapitation and epididymal WAT was minced and digested at 37° C. in Krebs-Ringer bicarbonate HEPES buffer (KRBH) containing 4% BSA (fatty acid-free), 0.5 mM/L glucose and 0.5 mg/mL collagenase type II (C6885; Sigma-Aldrich Co., Saint Louis, Mo., US) during 35-45 minutes. Fat cells were isolated by gentle centrifugation and washed three times with fresh collagenase-free KRBH without glucose. Adipocytes were resuspended in fresh KRBH without glucose and cell number was estimated as previously described. See DiGirolamo M, et al., Am. J. Physiol 1971; 221:850-858.

10. RNA Analysis

Total RNA was obtained from isolated adipocytes and adipose depots or liver by using QIAzol Lysis Reagent (Qiagen NV, Venlo, NL) or tripure isolation reagent (Roche Diagnostics Corp., Indianapolis, Ind., US), respectively, and RNeasy Lipid Tissue Minikit (Qiagen NV, Venlo, NL). In order to eliminate the residual viral genomes, total RNA was treated with DNAseI (Qiagen NV, Venlo, NL). For RT-PCR, 1 μg of RNA samples was reverse-transcribed using Superscript VILO cDNA Synthesis kit (Invitrogen™, Life Technologies Corp., Carslbad, Calif., US). Real-time quantitative PCR was performed in a SmartCyclerII® (Cepheid, Sunnyvale, USA) using EXPRESS SYBRGreen qPCR supermix (Invitrogen™, Life Technologies Corp., Carslbad, Calif., US). The sequences of the sense and antisense oligonucleotide primers are:

| Primer | Sequence | SEQ ID NO: |
|---|---|---|
| RFP sense | GCGGCCACTACACCTGCGAC | 4 |
| RFP antisense | TCGGCGTGCTCGTACTGCTC | 5 |
| mHkII sense | GAAGGGGCTAGGAGCTACCA | 6 |
| mHkII antisense | CTCGGAGCACACGGAAGTT | 7 |
| hSEAP sense | CGGCTGTTGGGCACTGA | 8 |
| hSEAP antisense | GGAAGGTCCGCTGGATTGA | 9 |
| mVEGF164 sense | AGACAGAACAAAGCCAGAAATCAC | 10 |
| mVEGF164 antisense | CACGTCTGCGGATCTTGGAC | 11 |
| total mVEGF sense | AAAAACGAAAGCGCAAGAAA | 12 |
| total mVEGF antisense | TTTCTCCGCTCTGAACAAGG | 13 |
| mPECAM1 sense | CTGGTGCTCTATGCAAGCCTC | 14 |
| mPECAM1 antisense | CGGTGCTGAGACCTGCTTT | 15 |
| GFP sense | AAGTTCATCTGCACCACCG | 16 |
| GFP antisense | TCCTTGAAGAAGATGGTGCGC | 17 |

Data was normalized with 36B4 values and analyzed as previously described. See Pfaffl M, Nucleic Acids Res. 2001; 29(9):e45.

11. Glucose Uptake Ex Vivo in Isolated Adipocytes

For isolated adipocytes from mice, 2-[1-$^3$H]deoxy-D-glucose (2-DG; Amersham Pharmacia Biotech Inc., Piscataway, N.J., US) uptake was measured at different insulin concentrations as previously described. See Traxinger R, et al., J. Biol. Chem. 1989; 264:8156-8163. Briefly, isolated adipocytes were obtained by collagenase digestion of epididymal WAT from fed mice as described before. 250 μL adipocyte suspension were incubated with KRBH+4% BSA (fatty acid-free), 10 mM/L deoxy-glucose, 0.4 μCi 2-[1-$^3$H] deoxy-D-glucose and different insulin concentrations for 5 minutes. Finally, adipocytes and incubation medium were separated through silicon oil (Sigma-Aldrich Co., Saint Louis, Mo., US) in polypropylene tubes and radioactivity in the adipocyte samples was assessed by liquid scintillation counting. The results were expressed as pmol of 2-[$^3$H]-DG per $10^6$ cells per minute.

12. Glucose Uptake In Vivo

In vivo basal glucose utilization index was determined as previously described. See Franckhauser S, et al., Diabetes 2002; 51:624-630. Briefly, 148 GBq (4 µCi) of the non-metabolizable glucose analog deoxy-D-[1,2-$^3$H]glucose (2-DG; PerkinElmer, Inc., Waltham, Mass., US) was mixed in BSA-citrate buffer. A flash injection of radiolabeled mix was administered into jugular vein of anesthetized (ketamine+xylazine) fed-mice at time zero. The specific blood 2-DG clearance was determined as previously described with 25 µL blood samples (tail vein) obtained 1, 15, and 30 minutes after injection. See Somogyi M, J. Biol. Chem. 1945; 160:69-73. Tissue samples were removed 30 minutes after injection. The glucose utilization index was determined by measuring the accumulation of radiolabeled compounds. See Ferré P, et al., Biochem. J. 1985; 228:103-110. The amount of 2-DG-6 phosphate per milligram of protein was divided by the integral of the concentration ratio of 2-DG to unlabeled glucose measured. Because values were not corrected by a "discrimination constant" for 2-DG in glucose metabolic pathways, the results are expressed as the index of glucose utilization, in picomols per milligram of protein per minute.

13. Measurement of Blood hSeAP Levels

Circulating hSeAP levels were determined from 5 µL of serum using the Tropix® Phospha-Light™ System (Applied Biosystems™, Life Technologies Corp., Carslbad, Calif., US).

14. Statistical Analysis

All values are expressed as mean±SEM. Differences between groups were compared by Student's t-test. Differences were considered significant at $p<0.05$.

Example 1

In Vivo Transduction of White Adipocytes by Local Administration of AAV

To assess the in vivo transduction efficiency of white adipose tissue (WAT) with AAV vectors, $4\times^{11}$ viral genomes (vg)/mouse of AAV of serotypes 1, 2, 4, 5, 6, 7, 8, and 9 encoding the marker protein GFP under the control of the ubiquitous promoter CAG (AAV-CAG-GFP) were injected bilaterally into the epididymal white adipose tissue (eWAT) of mice with or without the non-ionic surfactant Pluronics F88. See Croyle M, et al., Mol. Ther. 2001; 4:22-28, Gebhart C, et al., J. Control Release 2001; 73:401-416, Mizukami H, et al., Hum. Gene Ther. 2006; 17:921-928, and Sommer J, et al., Mol. Ther. 2003; 7:122-128. The administration of AAV1, AAV2, AAV4, and AAV5 without Pluronics F88 resulted in a very low percentage of transduced white adipocytes two weeks post-injection as assessed by immunostaining against GFP in eWAT. Moreover, no improvement of the adipose transduction efficiency mediated by any of the AAV serotypes tested was achieved by means of the Pluronics F88 addition. See FIG. 1A. Therefore, the use of this non-ionic surfactant was discarded for subsequent experiments. Independently of the addition of Pluronics F88, AAV1 was more efficient than AAV2, AAV4, and AAV5 in transducing eWAT in vivo. See Mizukami, 2006, supra. In contrast with the few scattered adipocytes and little groups of adipocytes that were transduced by AAV1, animals injected with AAV6 and AAV7 presented multiple large groups of GFP$^+$ white adipocytes. Furthermore, animals treated with AAV8 and AAV9 showed much greater transduction of eWAT, and the vast majority of adipocytes per eWAT area were transduced. See FIG. 1B. Quantification by fluorometric analysis of the GFP content in eWAT two weeks post-administration further confirmed that AAV of serotypes 6, 7, 8 and 9 were more efficient than AAV1 in transducing eWAT in vivo. See FIG. 1C. Noteworthy, epididymal fat pads injected with AAV8 and AAV9 presented the highest GFP content with no significant statistical differences between them. See FIG. 1C. Staining with the LacZ substrate 5-bromo-4-chloro-3-indolyl-β-D-galactopyranoside (X-gal) revealed widespread distribution of transduced adipocytes throughout eWAT two weeks after the unilaterally intra-eWAT administration of $2\times10^{11}$ vg/mouse of AAV8 encoding the LacZ gene under the control of the ubiquitous CMV promoter (AAV8-CMV-LacZ). See FIG. 1D. Local administration of AAV8 and AAV9-CAG-GFP vectors into the inguinal WAT (iWAT) mediated extensive transduction of white and beige adipocytes in this depot. See FIGS. 1G and H. Altogether, these results indicate that AAV8 and AAV9 were the most suitable vectors to genetically engineer WAT in vivo.

Figure 8:
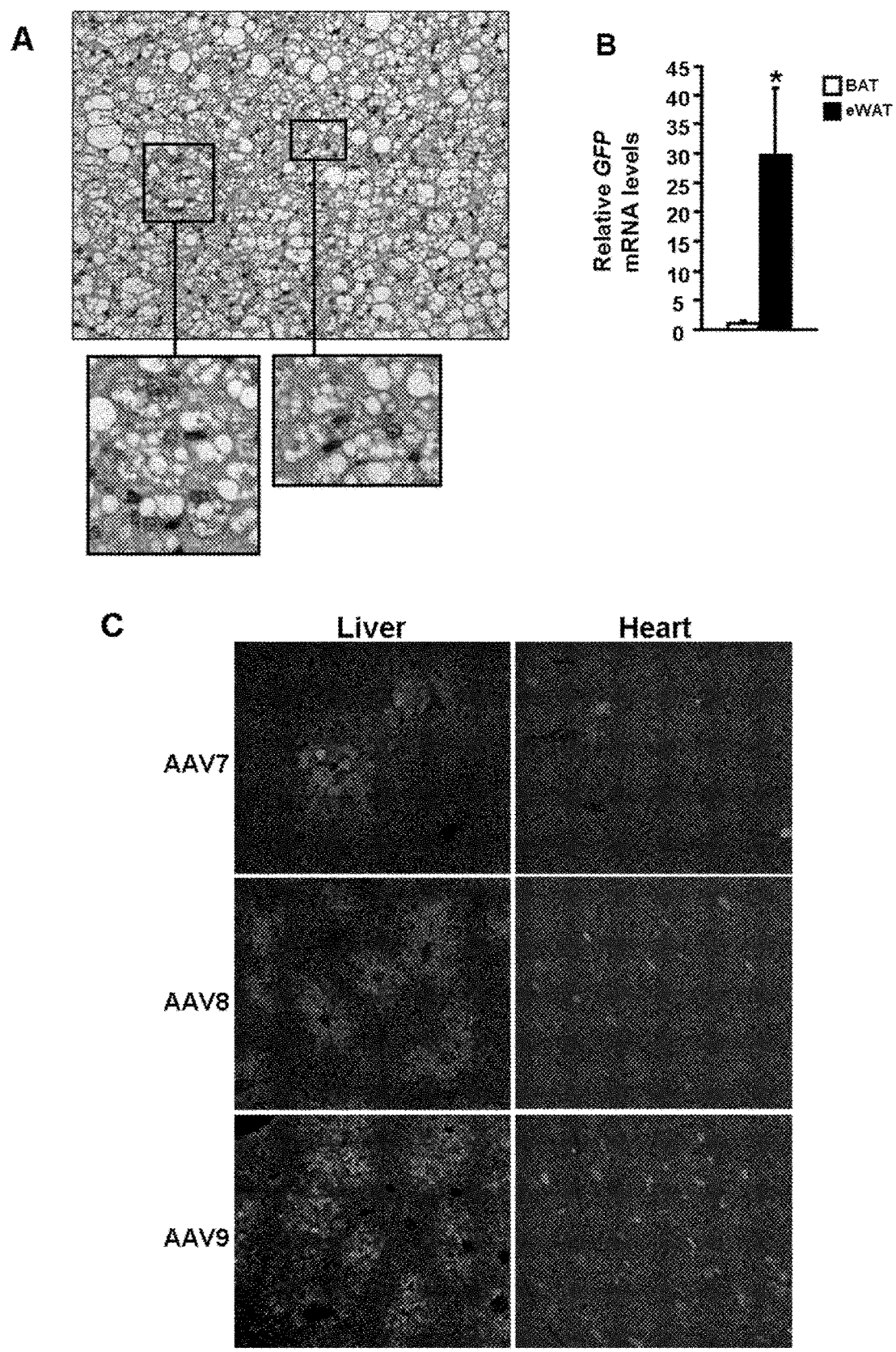
FIG. 8. Off-target transgene expression after intra-eWAT administration of AAV. A. Immunostaining against GFP (in brown) in iBAT from animals receiving AAV9-CAG-GFP. Original magnification ×200 and ×400 (insets). B. Relative GFP expression levels in iBAT and eWAT from animals treated with AAV9-CAG-GFP. Values shown are means±SEM. n=5 mice per group. *$p<0.05$. C. Transduction of non-adipose organs was evaluated by immunostaining against GFP (in green). GFP expression was apparent in the heart and liver from animals injected with AAV7, AAV8, or AAV9. Original magnification ×100. Analyses were performed two weeks post intra-eWAT administration of AAV-CAG-GFP vectors ($4\times10^{11}$ vg/mouse).

In addition, the intra-eWAT administration of AAV vectors resulted in transduction virtually restricted to eWAT. Two weeks post-injection, animals treated with AAV1, AAV6, AAV7, AAV8, or AAV9-CAG-GFP showed no transduction of the mesenteric, retroperitoneal and inguinal depots, whereas few GFP$^+$ brown adipocytes were present in iBAT of mice injected intra-eWAT with AAV9. See FIG. 8A. However, transgene expression in BAT was minimal compared to that detected in eWAT. See FIG. 8B. Regarding transduction of non-adipose tissues, the intra-eWAT administration of AAV7, AAV8, and AAV9-CAG-GFP also resulted in significant gene transfer to the liver and heart and to a marginal number of exocrine cells of the pancreas. See FIG. 8C.

As proof of concept to evaluate if AAV-transduced adipocytes in vivo may be a viable model to study adipose function, $4\times10^{11}$ vg/mouse of AAV9 vectors encoding the murine enzyme hexokinase II (mHKII) under the control of the ubiquitous promoter CMV (AAV9-CMV-mHKII) or an equal dose of AAV9-CMV-null vectors were injected bilaterally into the eWAT of healthy mice. Two weeks post-injection, isolated adipocytes from animals treated with AAV9-CMV-mHKII presented a 3-fold increase in the expression of mHKII compared with adipocytes from AAV9-CMV-null-injected mice. See FIG. 1E. To analyze the effects of AAV-mediated overexpression of mHKII in adipocytes, ex vivo basal and insulin-stimulated 2-[1-$^3$H]deoxy-D-glucose uptake into isolated adipocytes was determined. In AAV9-CMV-mHKII-transduced adipocytes basal 2-[1-$^3$H]deoxy-D-glucose uptake was slightly increased compared to AAV9-CMV-null-transduced adipocytes. In contrast, insulin stimulation led to a greater increase in the 2-[1-$^3$H]deoxy-D-glucose uptake by AAV9-CMV-mHKII-transduced adipocytes compared to adipocytes from animals treated with AAV9-CMV-null vectors. See FIG. 1F.

Example 2

In Vivo AAV-Mediated Specific Genetic Engineering of White Adipocytes

The use of a short version of the murine adipocyte protein 2 (mini/aP2) promoter composed merely of the adipocyte-specific enhancer in conjunction with the aP2 basal promoter was evaluated. See Ross, 1990 and Graves, 1992, supra. The purpose of this assay was to restrict AAV-mediated transgene expression to adipocytes. The unilateral intra-eWAT administration of $10^{12}$ vg/mouse of AAV8 and AAV9 encoding GFP under the control of the mini/aP2 regulatory region mediated confined transduction of white adipocytes, with no detectable GFP expression in the liver and heart two weeks post-injection. See FIGS. 2A and 9.

To evaluate the time-course of transgene expression mediated by the mini/aP2 regulatory region in mice, a dose of $4 \times 10^{12}$ vg/mouse of AAV9 vectors encoding the human placental-derived secreted alkaline phosphatase (hSeAP) cDNA under the control of the mini/aP2 regulatory region (AAV9-mini/aP2-SeAP) or saline solution were injected bilaterally into eWAT, and circulating hSeAP levels were measured at different time points after the AAV administration. High levels of hSeAP were detected in blood as soon as two weeks after AAV delivery and progressively increased up to day 40. Thereafter, circulating hSeAP levels persisted for the duration of the follow up, at least one year post-injection. Quantification of the hSeAP expression levels in the liver and eWAT by qPCR confirmed that eWAT was the tissue responsible for the major production of hSeAP. See FIGS. 2B-2C.

To assess whether AAV-mediated specific genetic engineering of white adipocytes may constitute a new tool to study adipocyte function, differentiation and metabolism in vivo in mice, $1.4 \times 10^{12}$ vg/mouse of AAV9 vectors encoding mHKII under the control of the mini/aP2 regulatory region (AAV9-mini/aP2-mHKII) or an equal dose of AAV9-mini/aP2-null vectors were administered to eWAT. Two weeks post-injection, in vivo basal 2-[1-$^3$H]deoxy-D-glucose uptake was determined. Animals receiving AAV9-mini/aP2-mHKII vectors showed increased basal 2-[1-$^3$H]deoxy-D-glucose uptake by eWAT compared with animals treated with AAV9-mini/aP2-null vectors. No difference in 2-[1-$^3$H]deoxy-D-glucose uptake under basal conditions was found between groups in iBAT and in tissues like the heart where the use of the mini/aP2 regulatory region impedes transgene expression. See FIG. 2D.

Example 3

In Vivo Genetic Engineering of Brown Adipocytes by Local Delivery of AAV Vectors In view that AAV8 and AAV9 were the most efficient vectors mediating genetic engineering of white adipocytes, transduction of brown adipocytes by the same serotypes was assessed. Two weeks after administration of $2 \times 10^9$ vg/mouse of AAV8 and AAV9-CAG-GFP vectors to the interscapular brown adipose tissue (iBAT) numerous GFP brown adipocytes were detected. See FIG. 3A. Assessment of GFP expression levels by qPCR revealed higher transduction efficiency of iBAT by AAV8 in comparison with AAV9 at a dose of $2 \times 10^9$ vg/mouse. See FIG. 3B. Once transduction of brown adipocytes was demonstrated using AAV8 and AAV9 vectors, we characterized the in vivo transduction efficiency of brown adipose tissue (BAT) with AAV of serotypes 1, 2, 4, 5, 6, 7, 8, and 9. To this end, a dose of $1.2 \times 10^{10}$ vg/mouse of AAV of serotypes 4 and 8 or a dose of $10^{11}$ vg/mouse of AAV of serotypes 1, 2, 5, 6, 7, 8, and 9 encoding the marker protein RFP under the control of the ubiquitous promoter CMV (AAV-CMV-RFP) were injected in the iBAT of mice. Two weeks after intra-iBAT administration, quantification of RFP expression levels by qPCR revealed higher transduction efficiency of iBAT by AAV7, AAV8, and AAV9 in comparison with AAV1, 2, 4, 5 and 6. See FIG. 3C. In agreement, widespread distribution of RFP$^+$ brown adipocytes was detected in iBAT of animals receiving AAV9 vectors. See FIG. 3D.

Figure 10:
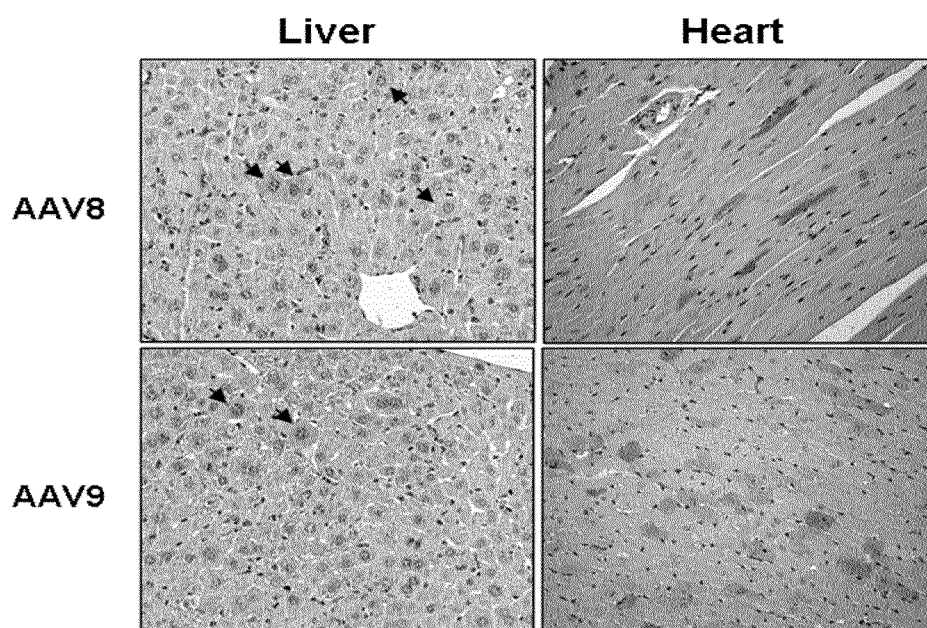
FIG. 10. Transduction of non-adipose organs by intra-iBAT administration of AAV vectors. Transduction of non-adipose organs was evaluated by immunostaining against GFP (in brown) two weeks post-injection. GFP expression was apparent in heart and liver from animals injected intra-iBAT with $2×10^9$ vg/mouse of AAV8 and AAV9-CAG-GFP vectors. Original magnification ×200.

In addition, the intra-iBAT administration of AAV resulted in restricted transduction of this depot with undetectable transgene expression in the epididymal, mesenteric, retroperitoneal and inguinal depots. Regarding transduction of non-adipose tissues, animals treated intra-iBAT with AAV7, AAV8, and AAV9 vectors showed transduction of the heart and liver, whereas GFP expression was undetectable in pancreas, intestine, spleen, lung, kidney, skeletal muscle, testis, epididymis, and brain. See FIG. 10.

Example 4

In Vivo AAV-Mediated Specific Genetic Engineering of Brown Adipocytes

A mini UCP1 (mini/UCP1) regulatory region composed of the enhancer conferring brown adipocyte-specific expression and the basal promoter of the rat UCP1 gene was utilized to mediate the expression of genes of interest in brown adipose tissue specifically. See Boyer B, et al., Mol. Cell Biol. 1991; 11:4147-4156, Kozak U, et al., Mol. Cell Biol. 1994; 14:59-67, Cassard-Doulcier, 1998, and Larose, 1996, supra. Two weeks after the intra-iBAT administration of $2 \times 10^{11}$ vg/mouse of AAV8 or AAV9-mini/UCP1-GFP vectors, efficient transduction of brown adipocytes was achieved. See FIG. 4A. Similarly, the intra-iBAT delivery of $2 \times 10^{11}$ vg/mouse of AAV8 and AAV9-mini/aP2-GFP also transduced brown adipocytes. See FIG. 11A. In addition, the mini/UCP1 regulatory region attained highly adipocyte-specific GFP expression, completely abolishing AAV-mediated transgene expression in the heart and mediating only marginal liver transduction. See FIG. 11B.

To examine whether AAV-mediated transduction of iBAT may be a new model to study brown adipocyte function, $7 \times 10$ vg/mouse of AAV8-mini/UCP1-mHKII vectors were administered to iBAT. Animals receiving AAV8-mini/UCP1-mHKII vectors showed increased basal 2-[1-$^3$H]deoxy-D-glucose uptake by iBAT compared with animals treated with AAV8-mini/UCP1-null vectors and no difference in 2-[1-$^3$H]deoxy-D-glucose uptake under basal conditions was found between groups in eWAT and heart. See FIG. 4B. Then, $2 \times 10^{11}$ vg/mouse of AAV9-mini/UCP1-VEGF$_{164}$ vectors or AAV9-mini/UCP1-null vectors were delivered intra-iBAT. Two weeks post-injection animals receiving AAV9-mini/UCP1-VEGF$_{164}$ vectors showed overexpression of VEGF$_{164}$ and increased levels of total VEGF in iBAT compared to animals treated with AAV9-mini/UCP1-null vectors. In addition, overexpression of PECAM1 (a commonly-used endothelial cell marker) was obtained in animals overexpressing VEGF$_{164}$. Animals treated with AAV9-mini/UCP1-VEGF$_{164}$ vectors showed increased number of vessels compared to animals receiving AAV9-mini/UCP1-null vectors as demonstrated by immunostaining against α-SMA in iBAT. See FIGS. 4C-4F.

Example 5

In Vivo Genetic Engineering of White and Brown Adipocytes by Systemic Administration of AAV8 and AAV9

Figure 12:
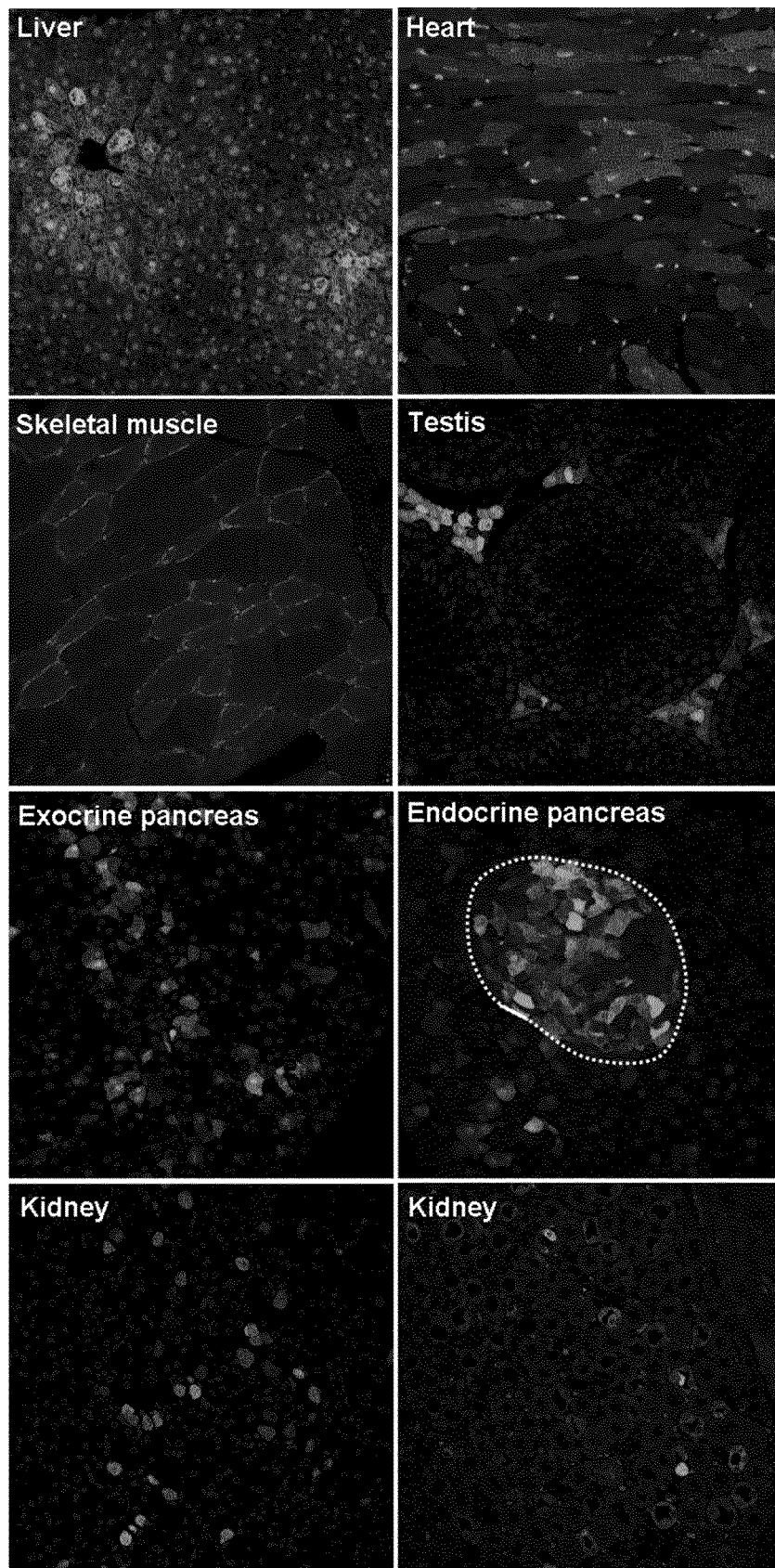
FIG. 12. Widespread transgene expression after tail vein delivery of AAV. Immunostaining against GFP (in green) two weeks post-injection of $5×10^{12}$ vg/mouse of AAV9-CAG-GFP vectors via tail vein revealed transduction of liver, heart, skeletal muscle, testis, and kidney. Blue, nuclei. Original magnification ×200.
Figure 13:
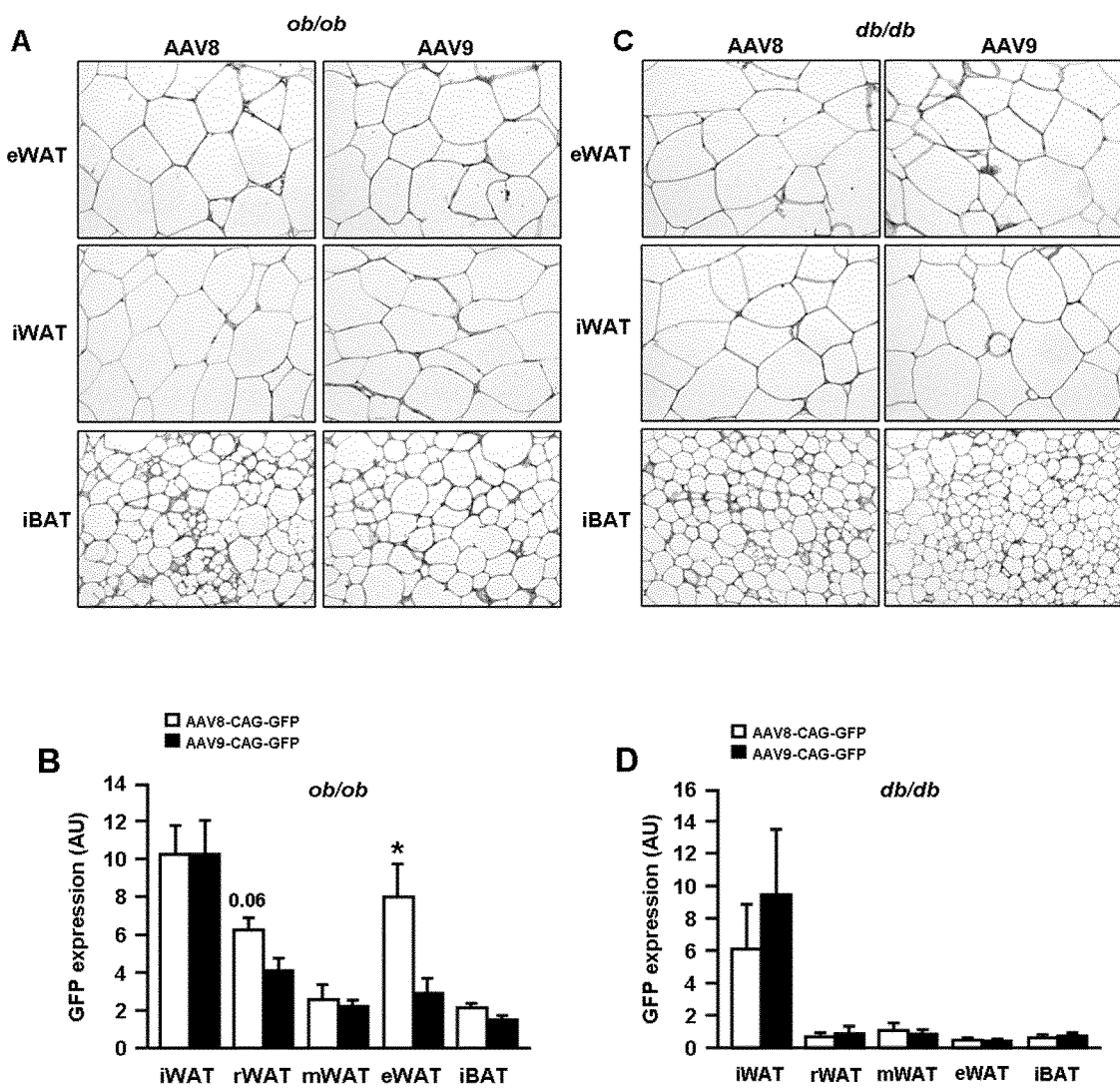
FIG. 13. Transduction of WAT and BAT after systemic administration of AAV vectors to obese-diabetic mice A-B. Immunostaining against GFP (brown) in epididymal white adipose tissue (eWAT), inguinal white adipose tissue (iWAT) and interscapular brown adipose tissue (iBAT) sections after iv administration of $3×10^{12}$ vg of AAV8 or AAV9-CAG-GFP vectors to ob/ob (A) and db/db mice (B). Original magnification ×200. (ob/ob: n=4; db/db: n=4). C-D. GFP expression in inguinal (iWAT), retroperitoneal (rWAT), mesenteric (mWAT), eWAT and iBAT depots from the same cohorts of ob/ob (C) and db/db mice (D). AU, arbitrary units. All analyses were performed two weeks after vector delivery. Values shown are means±SEM. *$p<0.05$ vs. AAV9.

A dose of $5 \times 10^{12}$ vg/mouse of AAV8 or AAV9-CAG-GFP vectors was administered via tail vein to lean mice. The transduction of the adipose depots was evaluated two weeks post-injection. Immunostaining against GFP of eWAT sections showed the AAV8- and AAV9-mediated transduction of white adipocytes. In addition, the measurement of GFP expression levels and GFP content demonstrated similar transduction efficiencies for both AAV8 and AAV9. Moreover, the systemic delivery of $5\times10^{12}$ vg/mouse of AAV8 or AAV9 vectors mediated the transduction of brown adipocytes of iBAT efficiently. The measurement of GFP expression levels by qPCR and GFP content by fluorometric analysis suggested that AAV8 presented a tendency towards displaying superior iBAT transduction efficiency than AAV9. In addition, the measurement of GFP expression levels by qPCR demonstrated gene transfer to the inguinal, retroperitoneal and mesenteric depots. However, remarkable differences in transduction efficiencies among depots were observed. See FIGS. 5A-5H. Importantly, the iv administration of AAV8 or AAV9 vectors to diabetic-obese ob/ob mice or db/db mice also resulted in the genetic engineering of WAT and BAT, with efficiencies similar to those attained in lean mice. See FIG. 13. The systemic administration of the AAV8 or AAV9-CAG-GFP vectors transduced a diversity of non-adipose tissues. See FIG. 12.

Example 6

In Vivo Specific Genetic Engineering of White and Brown Adipocytes with AAV-Mini/aP2 and AAV-Mini/UCP1 Vectors The systemic delivery of $2\times10^{12}$ vg/mouse of AAV8 or AAV9-mini/aP2-GFP resulted in transduction of white and brown adipocytes although low levels of transgene expression were afforded. See FIG. 7A. In contrast, the systemic administration of $2\times10^{12}$ vg/mouse of AAV8 or AAV9-mini/UCP1-GFP vectors mediated significant transduction of brown adipocytes. See FIG. 6A. In addition, AAV-mini/aP2-GFP and AAV-mini/UCP1-GFP vectors delivered intravenously attained highly adipocyte-specific GFP expression, with no detectable transgene expression in the heart and marginal transduction of the liver, which only presented a few scattered GFP+ hepatocytes. See FIGS. 7B-7C.

To further demonstrate the genetic engineering of adipocytes by systemic administration of AAV, $2\times10^{12}$ vg of AAV9-mini/UCP1-VEGF$_{164}$ or AAV9-mini/UCP1-null vectors were delivered via tail vein. Two months post-injection, animals receiving AAV9-mini/UCP1-VEGF$_{164}$ vectors showed increased expression of VEGF$_{164}$ and total VEGF compared to animals treated with AAV9-mini/UCP1-null vectors. See FIGS. 6B-6C. In addition, a dose of $8\times10^{12}$ vg of AAV9-mini/UCP1-VEGF$_{164}$ or AAV9-mini/UCP1-null vectors was also delivered via tail vein. One month post-injection, animals receiving $8\times10^{12}$ vg of AAV9-mini/UCP1-VEGF$_{164}$ vectors showed increased expression of VEGF$_{164}$ and PECAM1 and increased vessel density. See FIGS. 6D-6G.

Example 7

In Vivo Specific Genetic Engineering of Brown Adipocytes with AAV-Mini/aP2-GK

A dose of $2\times10^{11}$ vg/mouse of either AAV9 vectors encoding the rat glucokinase enzyme under the control of the mini/aP2 regulatory region (AAV9-mini/aP2-rGK) or an equal dose of AAV9-mini/aP2-null vectors will be administered locally to the iBAT of mice. Two weeks/one month post injection, in vivo basal and insulin-stimulated 2-[1-$^3$H] deoxy-D-glucose uptake will be determined in order to evaluate whether animals receiving AAV9-mini/aP2-rGK vectors show increased basal 2-[1-$^3$H]deoxy-D-glucose uptake specifically by iBAT compared with animals treated with AAV9-mini/aP2-null vectors.

Example 8

Figure 14:
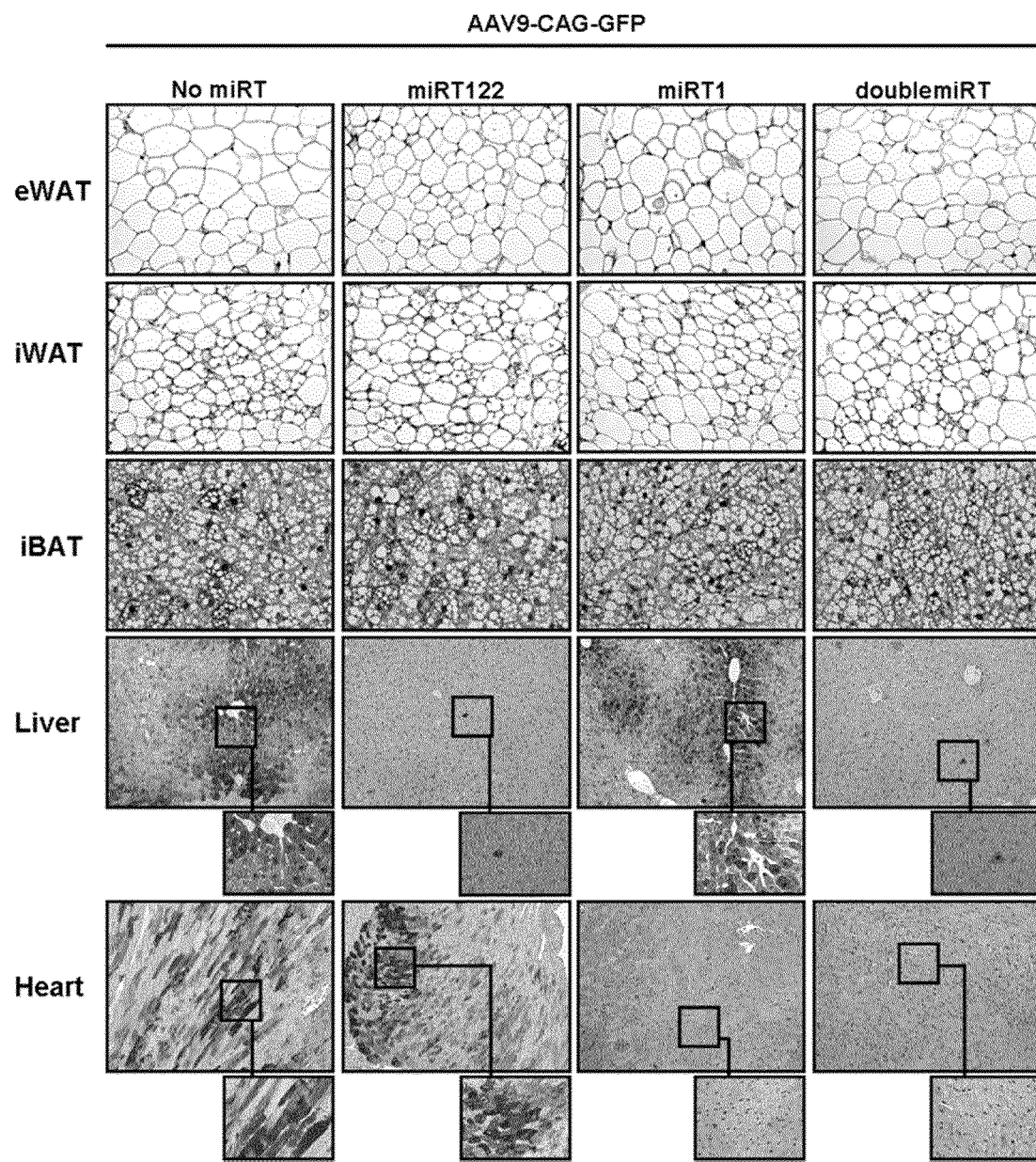
FIG. 14. Efficient adipocyte transduction and de-targeting of transgene expression from liver and heart with mirT sequences. GFP immunostaining (brown) in epididymal white adipose tissue (eWAT), inguinal white adipose tissue (iWAT), interscapular brown adipose tissue (iBAT), liver and heart two weeks after iv administration of $10^{12}$ vg of AAV9-CAG-GFP, AAV9-CAG-GFP-miRT122, AAV9-CAG-GFP-miRT1 or AAV9-CAG-GFP-doublemiRT vectors. Original magnification ×100 (liver and heart), ×200 (eWAT and iWAT) and ×400 (iBAT and insets).

Efficient Adipocyte Transduction and De-Targeting of Transgene Expression from Liver and Heart with mirT Sequences after Systemic Administration of AAV Vectors A dose of $10^{12}$ vg/mouse of AAV9 vectors encoding the GFP marker protein under the control of the ubiquitous CAG promoter (AAV9-CAG-GFP) or the CAG promoter with the addition of four tandem target sites of the liver-specific miR122a (AAV9-CAG-GFP-miRT122), the heart-specific miR1 (AAV9-CAG-GFP-miRT1) or both (AAV9-CAG-GFP-doublemiRT), cloned in the 3'UTR of the expression cassette, was administered systemically. Two weeks post-injection, high levels of GFP expression were observed in white and brown adipocytes from mice receiving AAV9-CAG-GFP, AAV9-CAG-GFP-miRT122, AAV9-CAG-GFP-miRT1 or AAV9-CAG-GFP-doublemiRT vectors. In contrast, GFP production in the liver or heart was nearly completely abolished in mice treated with AAV9-CAG-GFP-miRT122 or AAV9-CAG-GFP-miRT1 vectors, respectively. Noticeably, GFP production was greatly inhibited in both the liver and heart from AAV9-CAG-GFP-doublemiRT-treated mice. See FIG. 14.

The invention claimed is:

1. A method for treating and/or preventing a disease which requires or may benefit from the expression of a polynucleotide of interest in the adipose tissue, the method comprising administering an adeno-associated viral vector (AAV) selected from the group consisting of AAV6, AAV7, AAV8 and AAV9 comprising a recombinant viral genome wherein said recombinant viral genome comprises adeno-associated virus Inverted Terminal Repeats (ITRs) and an expression cassette, said expression cassette comprising an adipose tissue-specific transcriptional regulatory region operatively linked to a polynucleotide of interest.

2. The method of claim 1 wherein the adipose tissue-specific transcriptional regulatory region comprises a promoter region selected from the group consisting of a basal aP2 promoter and a basal UCP1 promoter.

3. The method of claim 2 wherein the adipose tissue-specific transcriptional regulatory region further comprises an enhancer region operatively linked to the promoter region.

4. The method of claim 3 wherein the enhancer region is selected from the group consisting of an adipose-specific aP2 enhancer and an adipose-specific UCP1 enhancer.

5. The method of claim 3 wherein the transcriptional regulatory region is selected from the group consisting of:
   a polynucleotide comprising an adipose-specific aP2 enhancer and a basal murine aP2 promoter; and
   a polynucleotide comprising the adipose-specific UCP1 enhancer and a basal rat UCP1 promoter.

6. The method of claim 1 wherein the expression cassette further comprises a post-transcriptional regulatory region.

7. The method of claim 6 wherein the post-transcriptional regulatory region is a Woodchuck Hepatitis Virus Posttranscriptional Regulatory Element (WPRE).

8. The method of claim 1 wherein the polynucleotide of interest encodes a protein which is selected from the group consisting of a secreted protein which acts systemically and a protein which acts upon or in a vicinity of an adipocyte.

9. The method of claim 1 wherein the polynucleotide of interest encodes a protein selected from the group consisting of: hexokinase, glucokinase, alkaline phosphatase, and vascular endothelial growth factor.

10. The method of claim 1 wherein the adeno-associated virus ITRs are AAV2 ITRs.

11. A method for treating and/or preventing a disease which requires or may benefit from the expression of a polynucleotide of interest in the adipose tissue, the method comprising administering an adeno-associated viral vector (AAV) selected from the group consisting of AAV6, AAV7, AAV8 and AAV9 comprising a recombinant viral genome wherein said recombinant viral genome comprises adeno-associated virus inverted Terminal Repeats (ITRs) and an expression cassette, said expression cassette comprising a transcriptional regulatory region operatively linked to a polynucleotide of interest, wherein said transcriptional regulatory region comprises a constitutive promoter and wherein said AAV further comprises at least one miRNA target sequence.

12. The method of claim 11 wherein the at least one miRNA target sequence is mirT122a.

13. The method of claim 11 wherein the at least one miRNA target sequence is mirT1.

14. The method of claim 11 wherein said AAV comprises at least one copy of mirT1 and one copy of mirT122a.

15. The method of claim 1, wherein the adeno-associated viral vector (AAV) is present in a pharmaceutical composition.

16. The method of claim 1 wherein the adipose tissue comprises white adipose tissue.

17. The method of claim 1 wherein the adipose tissue comprises brown adipose tissue.

18. The method of claim 1 wherein the adeno-associated viral vector is administered systemically or locally.

19. The method of claim 11, wherein the adeno-associated viral vector (AAV) is present in a pharmaceutical composition.

20. The method of claim 11, wherein the adeno-associated viral vector is administered systemically or locally.

* * * * *